US012232957B2

(12) United States Patent
Straubinger et al.

(10) Patent No.: US 12,232,957 B2
(45) Date of Patent: Feb. 25, 2025

(54) STENT FOR THE POSITIONING AND ANCHORING OF A VALVULAR PROSTHESIS IN AN IMPLANTATION SITE IN THE HEART OF A PATIENT

(71) Applicant: JenaValve Technology, Inc., Irvine, CA (US)

(72) Inventors: Helmut Straubinger, Aschheim (DE); Johannes Jung, Karlsruhe (DE)

(73) Assignee: JenaValve Technology, Inc., Irvine, CA (US)

( * ) Notice: Subject to any disclaimer, the term of this patent is extended or adjusted under 35 U.S.C. 154(b) by 30 days.

(21) Appl. No.: 18/160,993

(22) Filed: Jan. 27, 2023

(65) Prior Publication Data
US 2023/0172712 A1    Jun. 8, 2023

Related U.S. Application Data

(63) Continuation of application No. 16/741,956, filed on Jan. 14, 2020, now Pat. No. 11,564,794, which is a
(Continued)

(51) Int. Cl.
*A61F 2/24* (2006.01)
(52) U.S. Cl.
CPC .... *A61F 2/2418* (2013.01); *A61F 2220/0016* (2013.01); *A61F 2230/0023* (2013.01); *A61F 2230/0054* (2013.01)
(58) Field of Classification Search
CPC ...... A61F 2220/0016; A61F 2230/0023; A61F 2230/0054; A61F 2/2418
See application file for complete search history.

(56) References Cited

U.S. PATENT DOCUMENTS 15,192 A    6/1856 Peale
388,776 A    8/1888 Hall
(Continued)

FOREIGN PATENT DOCUMENTS

AU    757647 B2    2/2003
AU    776895 B2    9/2004
(Continued)

OTHER PUBLICATIONS

US 6,331,185 B1, 12/2001, Gambale et al. (withdrawn)
(Continued)

*Primary Examiner* — Julian W Woo
(74) *Attorney, Agent, or Firm* — Greenberg Traurig, LLP; Christopher C. Bolten; Robert D. Ward

(57) ABSTRACT

The present invention relates to a stent (10) for the positioning and anchoring of a valvular prosthesis (100) in an implantation site in the heart of a patient. Specifically, the present invention relates to an expandable stent for an endoprosthesis used in the treatment of a narrowing of a cardiac valve and/or a cardiac valve insufficiency. So as to ensure that no longitudinal displacement of a valvular prosthesis (100) fastened to a stent (10) will occur relative the stent (10) in the implanted state of the stent (10), even given the peristaltic motion of the heart, the stent (10) according to the invention comprises at least one fastening portion (11) via which the valvular prosthesis (100) is connectable to the stent (10). The stent (10) further comprises positioning arches (15) and retaining arches (16), whereby at least one positioning arch (15) is connected to at least one retaining arch (16) via a first connecting land (17). The stent (10) moreover comprises at least one auxiliary retaining arch (18) which connects the respective arms (16', 16") of the at least one retaining arch (16) connected to the at least one positioning arch (15).

20 Claims, 11 Drawing Sheets

Figure 1A:
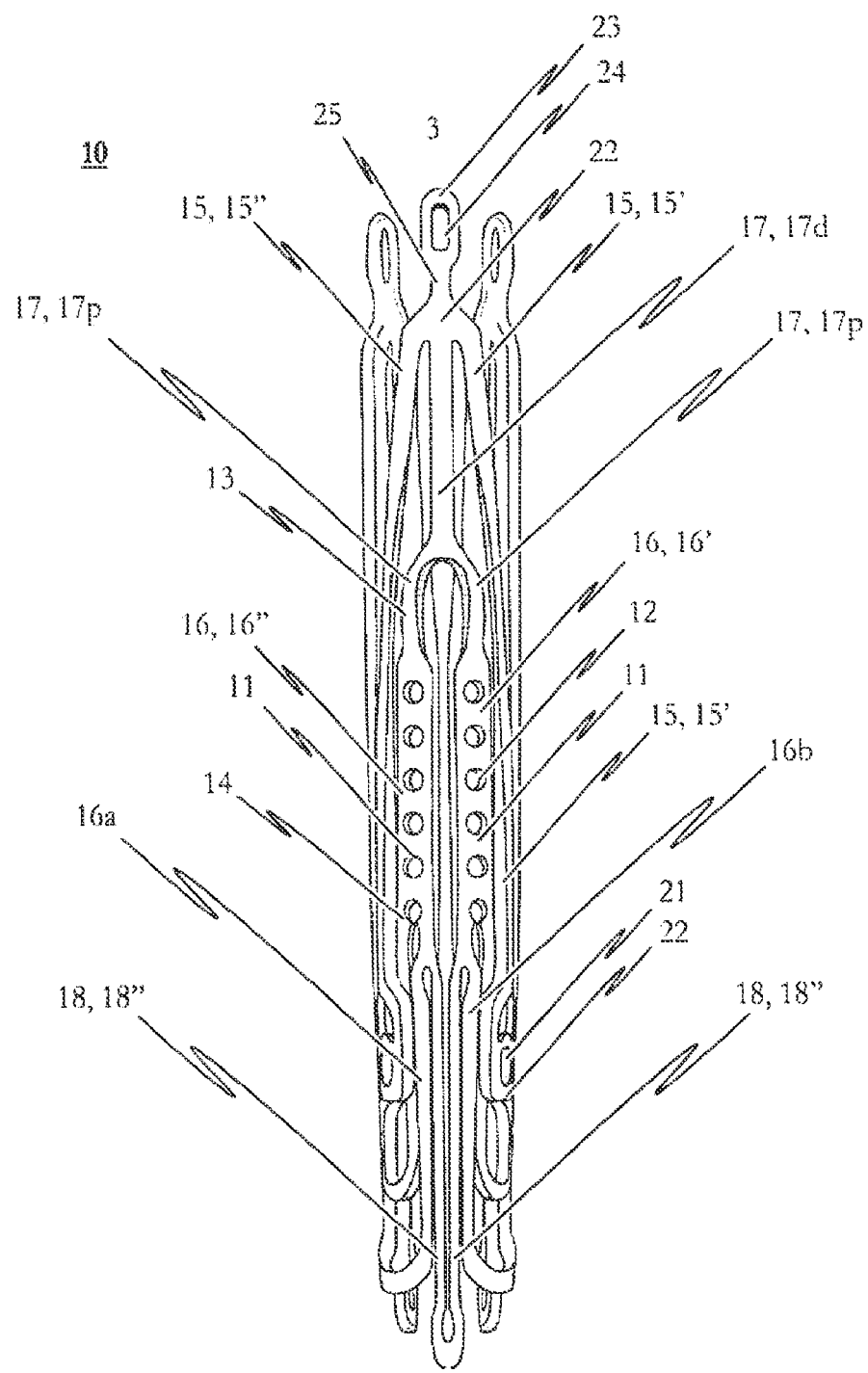

Related U.S. Application Data continuation of application No. 15/850,165, filed on Dec. 21, 2017, now Pat. No. 10,575,947, which is a continuation of application No. 14/709,909, filed on May 12, 2015, now Pat. No. 9,877,828, which is a continuation of application No. 12/071,814, filed on Feb. 26, 2008, now Pat. No. 9,044,318.

(56) References Cited

U.S. PATENT DOCUMENTS

| | | |
|---|---|---|
| 944,214 A | 12/1909 | Rydquist |
| 2,121,182 A | 6/1938 | Benjamin |
| 2,669,896 A | 2/1954 | Clough |
| 2,682,057 A | 6/1954 | Lord |
| 2,701,559 A | 2/1955 | Cooper |
| 2,832,078 A | 4/1958 | Williams |
| 3,029,819 A | 4/1962 | Edward et al. |
| 3,099,016 A | 7/1963 | Lowell et al. |
| 3,113,586 A | 12/1963 | Edmark, Jr. et al. |
| 3,130,418 A | 4/1964 | Head et al. |
| 3,143,742 A | 8/1964 | Cromie |
| 3,210,836 A | 10/1965 | Johanson et al. |
| 3,221,006 A | 11/1965 | Moore et al. |
| 3,334,629 A | 8/1967 | Cohn |
| 3,365,728 A | 1/1968 | Lowell et al. |
| 3,367,364 A | 2/1968 | Cruz, Jr. et al. |
| 3,409,013 A | 11/1968 | Henry et al. |
| 3,445,916 A | 5/1969 | Schulte et al. |
| 3,540,431 A | 11/1970 | Mobin-Uddin et al. |
| 3,548,417 A | 12/1970 | Kischer et al. |
| 3,570,014 A | 3/1971 | Hancock et al. |
| 3,574,865 A | 4/1971 | Hamaker |
| 3,587,115 A | 6/1971 | Shiley et al. |
| 3,592,184 A | 7/1971 | Watkins et al. |
| 3,628,535 A | 12/1971 | Ostrowsky et al. |
| 3,642,004 A | 2/1972 | Osthagen et al. |
| 3,657,744 A | 4/1972 | Ersek |
| 3,671,979 A | 6/1972 | Moulopoulos |
| 3,714,671 A | 2/1973 | Edwards et al. |
| 3,725,961 A | 4/1973 | Magovern et al. |
| 3,755,823 A | 9/1973 | Hancock |
| 3,795,246 A | 3/1974 | Sturgeon |
| 3,839,741 A | 10/1974 | Haller |
| 3,868,956 A | 3/1975 | Alfidi et al. |
| 3,874,388 A | 4/1975 | King et al. |
| 3,983,581 A | 10/1976 | Angell et al. |
| 3,997,923 A | 12/1976 | Possis |
| 4,035,849 A | 7/1977 | Angell et al. |
| 4,056,854 A | 11/1977 | Boretos et al. |
| 4,078,268 A | 3/1978 | Possis |
| 4,084,268 A | 4/1978 | Ionescu et al. |
| 4,106,126 A | 8/1978 | Traenkle |
| 4,106,129 A | 8/1978 | Carpentier et al. |
| 4,118,806 A | 10/1978 | Porier et al. |
| 4,164,046 A | 8/1979 | Cooley |
| 4,182,446 A | 1/1980 | Penny |
| 4,191,218 A | 3/1980 | Clark et al. |
| 4,214,587 A | 7/1980 | Sakura, Jr. |
| 4,215,871 A | 8/1980 | Hirsch et al. |
| 4,222,126 A | 9/1980 | Boretos et al. |
| 4,233,690 A | 11/1980 | Akins |
| 4,261,342 A | 4/1981 | Aranguren Duo |
| 4,263,680 A | 4/1981 | Reul et al. |
| 4,265,694 A | 5/1981 | Boretos et al. |
| 4,291,420 A | 9/1981 | Reul |
| 4,297,749 A | 11/1981 | Davis et al. |
| 4,319,831 A | 3/1982 | Matsui et al. |
| RE30,912 E | 4/1982 | Hancock |
| 4,323,358 A | 4/1982 | Lentz et al. |
| 4,326,306 A | 4/1982 | Poler |
| 4,339,831 A | 7/1982 | Johnson |
| 4,343,048 A | 8/1982 | Ross et al. |
| 4,345,340 A | 8/1982 | Rosen |
| 4,350,492 A | 9/1982 | Wright et al. |
| 4,373,216 A | 2/1983 | Klawitter |
| 4,388,735 A | 6/1983 | Ionescu et al. |
| 4,406,022 A | 9/1983 | Roy |
| 4,423,809 A | 1/1984 | Mazzocco |
| 4,425,908 A | 1/1984 | Simon |
| 4,441,215 A | 4/1984 | Kaster |
| 4,441,216 A | 4/1984 | Ionescu et al. |
| 4,470,157 A | 9/1984 | Love |
| 4,484,579 A | 11/1984 | Meno et al. |
| 4,485,816 A | 12/1984 | Krumme |
| 4,491,986 A | 1/1985 | Gabbay |
| 4,501,030 A | 2/1985 | Lane |
| 4,502,488 A | 3/1985 | Degironimo et al. |
| 4,531,943 A | 7/1985 | Van Tassel et al. |
| 4,535,483 A | 8/1985 | Klawitter et al. |
| 4,546,499 A | 10/1985 | Possis et al. |
| 4,574,803 A | 3/1986 | Storz |
| 4,580,568 A | 4/1986 | Gianturco |
| 4,592,340 A | 6/1986 | Boyles |
| 4,602,911 A | 7/1986 | Ahmadi et al. |
| 4,605,407 A | 8/1986 | Black et al. |
| 4,610,688 A | 9/1986 | Silvestrini et al. |
| 4,612,011 A | 9/1986 | Kautzky |
| 4,617,932 A | 10/1986 | Kornberg |
| 4,619,246 A | 10/1986 | Molgaard-Nielsen et al. |
| 4,643,732 A | 2/1987 | Pietsch et al. |
| 4,647,283 A | 3/1987 | Carpentier et al. |
| 4,648,881 A | 3/1987 | Carpentier et al. |
| 4,655,218 A | 4/1987 | Kulik et al. |
| 4,655,771 A | 4/1987 | Wallsten |
| 4,662,885 A | 5/1987 | DiPisa, Jr. |
| 4,665,906 A | 5/1987 | Jervis |
| 4,665,918 A | 5/1987 | Garza et al. |
| 4,680,031 A | 7/1987 | Alonso |
| 4,681,908 A | 7/1987 | Broderick et al. |
| 4,687,483 A | 8/1987 | Fisher et al. |
| 4,692,164 A | 9/1987 | Dzemeshkevich et al. |
| 4,705,516 A | 11/1987 | Barone et al. |
| 4,710,192 A | 12/1987 | Liotta et al. |
| 4,733,665 A | 3/1988 | Palmaz |
| 4,755,181 A | 7/1988 | Igoe |
| 4,759,758 A | 7/1988 | Gabbay |
| 4,769,029 A | 9/1988 | Patel |
| 4,777,951 A | 10/1988 | Cribier et al. |
| 4,787,899 A | 11/1988 | Lazarus |
| 4,787,901 A | 11/1988 | Baykut |
| 4,796,629 A | 1/1989 | Grayzel |
| 4,797,901 A | 1/1989 | Goerne et al. |
| 4,806,595 A | 2/1989 | Noishiki et al. |
| 4,819,751 A | 4/1989 | Shimada et al. |
| 4,829,990 A | 5/1989 | Thuroff et al. |
| 4,834,755 A | 5/1989 | Silvestrini et al. |
| 4,846,830 A | 7/1989 | Knoch et al. |
| 4,851,001 A | 7/1989 | Taheri |
| 4,856,516 A | 8/1989 | Hillstead |
| 4,865,600 A | 9/1989 | Carpentier et al. |
| 4,872,874 A | 10/1989 | Taheri |
| 4,873,978 A | 10/1989 | Ginsburg |
| 4,878,495 A | 11/1989 | Grayzel |
| 4,878,906 A | 11/1989 | Lindemann et al. |
| 4,883,458 A | 11/1989 | Shiber |
| 4,885,005 A | 12/1989 | Nashef et al. |
| 4,909,252 A | 3/1990 | Goldberger |
| 4,917,102 A | 4/1990 | Miller et al. |
| 4,922,905 A | 5/1990 | Strecker |
| 4,927,426 A | 5/1990 | Dretler |
| 4,950,227 A | 8/1990 | Savin et al. |
| 4,953,553 A | 9/1990 | Tremulis |
| 4,954,126 A | 9/1990 | Wallsten |
| 4,966,604 A | 10/1990 | Reiss |
| 4,969,890 A | 11/1990 | Sugita et al. |
| 4,979,939 A | 12/1990 | Shiber |
| 4,986,830 A | 1/1991 | Owens et al. |
| 4,994,077 A | 2/1991 | Dobben |
| 5,002,556 A | 3/1991 | Ishida et al. |
| 5,002,559 A | 3/1991 | Tower |
| 5,002,566 A | 3/1991 | Carpentier et al. |
| 5,007,896 A | 4/1991 | Shiber |
| 5,026,366 A | 6/1991 | Leckrone |
| 5,026,377 A | 6/1991 | Burton et al. |

(56) References Cited

U.S. PATENT DOCUMENTS

| | | |
|---|---|---|
| 5,032,128 A | 7/1991 | Alonso |
| 5,035,706 A | 7/1991 | Giantureo et al. |
| 5,037,434 A | 8/1991 | Lane |
| 5,047,041 A | 9/1991 | Samuels |
| 5,053,008 A | 10/1991 | Bajaj |
| 5,059,177 A | 10/1991 | Towne et al. |
| 5,061,273 A | 10/1991 | Yock |
| 5,061,277 A | 10/1991 | Carpentier et al. |
| 5,064,435 A | 11/1991 | Porter |
| 5,078,720 A | 1/1992 | Burton et al. |
| 5,080,668 A | 1/1992 | Bolz et al. |
| 5,085,635 A | 2/1992 | Cragg |
| 5,089,015 A | 2/1992 | Ross |
| 5,094,661 A | 3/1992 | Levy et al. |
| 5,104,399 A | 4/1992 | Lazarus |
| 5,104,407 A | 4/1992 | Lam et al. |
| 5,108,425 A | 4/1992 | Hwang |
| 5,122,154 A | 6/1992 | Rhodes |
| 5,132,473 A | 7/1992 | Furutaka et al. |
| 5,141,494 A | 8/1992 | Danforth et al. |
| 5,143,987 A | 9/1992 | Hansel et al. |
| 5,147,388 A | 9/1992 | Yamazaki |
| 5,152,771 A | 10/1992 | Sabbaghian et al. |
| 5,159,937 A | 11/1992 | Tremulis |
| 5,161,547 A | 11/1992 | Tower |
| 5,163,953 A | 11/1992 | Vince |
| 5,163,955 A | 11/1992 | Love et al. |
| 5,167,628 A | 12/1992 | Boyles |
| 5,178,632 A | 1/1993 | Hanson |
| 5,192,301 A | 3/1993 | Kamiya et al. |
| 5,193,546 A | 3/1993 | Shaknovich |
| 5,197,979 A | 3/1993 | Quintero et al. |
| 5,201,757 A | 4/1993 | Heyn et al. |
| 5,207,695 A | 5/1993 | Trout, III |
| 5,209,741 A | 5/1993 | Spaeth |
| 5,211,183 A | 5/1993 | Wilson |
| 5,215,541 A | 6/1993 | Nashef et al. |
| 5,217,481 A | 6/1993 | Barbara |
| 5,217,483 A | 6/1993 | Tower |
| 5,232,445 A | 8/1993 | Bonzel |
| 5,234,447 A | 8/1993 | Kaster et al. |
| 5,234,456 A | 8/1993 | Silvestrini |
| 5,238,004 A | 8/1993 | Sahatjian et al. |
| 5,258,008 A | 11/1993 | Wilk |
| 5,258,023 A | 11/1993 | Reger |
| 5,258,042 A | 11/1993 | Mehta |
| 5,272,909 A | 12/1993 | Nguyen et al. |
| 5,275,580 A | 1/1994 | Yamazaki |
| 5,279,612 A | 1/1994 | Eberhardt |
| 5,282,847 A | 2/1994 | Trescony et al. |
| 5,287,861 A | 2/1994 | Wilk |
| 5,295,958 A | 3/1994 | Shturman |
| 5,327,774 A | 7/1994 | Nguyen et al. |
| 5,330,486 A | 7/1994 | Wilk |
| 5,330,500 A | 7/1994 | Song |
| 5,332,402 A | 7/1994 | Teitelbaum |
| 5,336,258 A | 8/1994 | Quintero et al. |
| 5,342,348 A | 8/1994 | Kaplan |
| 5,344,426 A | 9/1994 | Lau et al. |
| 5,344,427 A | 9/1994 | Cottenceau et al. |
| 5,344,442 A | 9/1994 | Deac |
| 5,350,398 A | 9/1994 | Pavcnik et al. |
| 5,350,399 A | 9/1994 | Erlebacher et al. |
| 5,352,240 A | 10/1994 | Ross |
| 5,354,330 A | 10/1994 | Hanson et al. |
| 5,360,444 A | 11/1994 | Kusuhara |
| 5,368,608 A | 11/1994 | Levy et al. |
| 5,370,685 A | 12/1994 | Stevens |
| 5,380,054 A | 1/1995 | Galvis |
| 5,387,235 A | 2/1995 | Chuter |
| 5,389,096 A | 2/1995 | Aita et al. |
| 5,389,106 A | 2/1995 | Tower |
| 5,397,351 A | 3/1995 | Pavcnik et al. |
| 5,397,355 A | 3/1995 | Marin et al. |
| 5,409,019 A | 4/1995 | Wilk |
| 5,411,552 A | 5/1995 | Andersen et al. |
| 5,415,633 A | 5/1995 | Lazarus et al. |
| 5,425,739 A | 6/1995 | Jessen |
| 5,425,762 A | 6/1995 | Muller |
| 5,429,144 A | 7/1995 | Wilk |
| 5,431,676 A | 7/1995 | Dubrul et al. |
| 5,433,723 A | 7/1995 | Lindenberg et al. |
| 5,443,446 A | 8/1995 | Shturman |
| 5,443,449 A | 8/1995 | Buelna |
| 5,443,477 A | 8/1995 | Marin et al. |
| 5,443,495 A | 8/1995 | Buscemi et al. |
| 5,443,499 A | 8/1995 | Schmitt |
| 5,449,384 A | 9/1995 | Johnson |
| 5,456,712 A | 10/1995 | Maginot |
| 5,456,713 A | 10/1995 | Chuter |
| 5,464,449 A | 11/1995 | Ryan et al. |
| 5,469,868 A | 11/1995 | Reger |
| 5,470,320 A | 11/1995 | Tiefenbrun et al. |
| 5,476,506 A | 12/1995 | Lunn |
| 5,476,508 A | 12/1995 | Amstrup |
| 5,476,510 A | 12/1995 | Eberhardt et al. |
| 5,480,423 A | 1/1996 | Ravenscroft et al. |
| 5,480,424 A | 1/1996 | Cox |
| 5,486,193 A | 1/1996 | Bourne et al. |
| 5,487,760 A | 1/1996 | Villafana |
| 5,489,294 A | 2/1996 | McVenes et al. |
| 5,489,297 A | 2/1996 | Duran |
| 5,489,298 A | 2/1996 | Love et al. |
| 5,496,346 A | 3/1996 | Horzewski et al. |
| 5,499,995 A | 3/1996 | Teirstein |
| 5,500,014 A | 3/1996 | Quijano et al. |
| 5,500,015 A | 3/1996 | Deac |
| 5,507,767 A | 4/1996 | Maeda et al. |
| 5,509,930 A | 4/1996 | Love |
| 5,522,881 A | 6/1996 | Lentz |
| 5,527,337 A | 6/1996 | Stack et al. |
| 5,530,949 A | 6/1996 | Koda et al. |
| 5,534,007 A | 7/1996 | St. Germain et al. |
| 5,540,712 A | 7/1996 | Kleshinski et al. |
| 5,545,133 A | 8/1996 | Burns et al. |
| 5,545,209 A | 8/1996 | Roberts et al. |
| 5,545,211 A | 8/1996 | An et al. |
| 5,545,214 A | 8/1996 | Stevens |
| 5,549,665 A | 8/1996 | Vesely et al. |
| 5,549,666 A | 8/1996 | Hata et al. |
| 5,554,119 A | 9/1996 | Harrison et al. |
| 5,554,185 A | 9/1996 | Block et al. |
| 5,569,274 A | 10/1996 | Rapacki et al. |
| 5,571,167 A | 11/1996 | Maginot |
| 5,571,174 A | 11/1996 | Love et al. |
| 5,571,175 A | 11/1996 | Vanney et al. |
| 5,571,215 A | 11/1996 | Sterman et al. |
| 5,573,520 A | 11/1996 | Schwartz et al. |
| 5,575,818 A | 11/1996 | Pinchuk |
| 5,580,922 A | 12/1996 | Park et al. |
| 5,591,185 A | 1/1997 | Kilmer et al. |
| 5,591,195 A | 1/1997 | Taheri et al. |
| 5,593,434 A | 1/1997 | Williams |
| 5,595,571 A | 1/1997 | Jaffe et al. |
| 5,596,471 A | 1/1997 | Hanlin |
| 5,607,464 A | 3/1997 | Trescony et al. |
| 5,607,465 A | 3/1997 | Camilli |
| 5,609,626 A | 3/1997 | Quijano et al. |
| 5,613,982 A | 3/1997 | Goldstein |
| 5,618,299 A | 4/1997 | Khosravi et al. |
| 5,626,553 A | 5/1997 | Frassica et al. |
| 5,628,784 A | 5/1997 | Strecker |
| 5,632,778 A | 5/1997 | Goldstein |
| 5,634,942 A | 6/1997 | Chevillon et al. |
| 5,643,278 A | 7/1997 | Wijay |
| 5,645,559 A | 7/1997 | Hachtman et al. |
| 5,653,684 A | 8/1997 | Laptewicz et al. |
| 5,653,745 A | 8/1997 | Trescony et al. |
| 5,653,749 A | 8/1997 | Love et al. |
| 5,655,548 A | 8/1997 | Nelson et al. |
| 5,662,124 A | 9/1997 | Wilk |
| 5,662,671 A | 9/1997 | Barbut et al. |
| 5,662,703 A | 9/1997 | Yurek et al. |
| 5,665,115 A | 9/1997 | Cragg |

(56) References Cited

U.S. PATENT DOCUMENTS

| | | |
|---|---|---|
| 5,667,523 A | 9/1997 | Bynon et al. |
| 5,674,277 A | 10/1997 | Freitag |
| 5,674,298 A | 10/1997 | Levy et al. |
| 5,679,112 A | 10/1997 | Levy et al. |
| 5,681,345 A | 10/1997 | Euteneuer |
| 5,682,906 A | 11/1997 | Sterman et al. |
| 5,683,451 A | 11/1997 | Lenker et al. |
| 5,690,644 A | 11/1997 | Yurek et al. |
| 5,693,083 A | 12/1997 | Baker et al. |
| 5,693,088 A | 12/1997 | Lazarus |
| 5,693,310 A | 12/1997 | Gries et al. |
| 5,695,498 A | 12/1997 | Tower |
| 5,697,972 A | 12/1997 | Kim et al. |
| 5,700,269 A | 12/1997 | Pinchuk et al. |
| 5,702,368 A | 12/1997 | Stevens et al. |
| 5,709,713 A | 1/1998 | Evans et al. |
| 5,713,917 A | 2/1998 | Leonhardt et al. |
| 5,713,950 A | 2/1998 | Cox |
| 5,713,951 A | 2/1998 | Garrison et al. |
| 5,713,953 A | 2/1998 | Vallana et al. |
| 5,716,370 A | 2/1998 | Williamson, IV et al. |
| 5,716,417 A | 2/1998 | Girard et al. |
| 5,718,725 A | 2/1998 | Sterman et al. |
| 5,720,391 A | 2/1998 | Dohm et al. |
| 5,720,776 A | 2/1998 | Chuter et al. |
| 5,725,549 A | 3/1998 | Lam |
| 5,725,550 A | 3/1998 | Nadal |
| 5,728,068 A | 3/1998 | Leone et al. |
| 5,728,151 A | 3/1998 | Garrison et al. |
| 5,733,267 A | 3/1998 | Del Toro |
| 5,733,325 A | 3/1998 | Robinson et al. |
| 5,735,842 A | 4/1998 | Krueger et al. |
| 5,746,476 A | 5/1998 | Novak et al. |
| 5,746,709 A | 5/1998 | Rom et al. |
| 5,746,765 A | 5/1998 | Kleshinski et al. |
| 5,746,775 A | 5/1998 | Levy et al. |
| 5,749,890 A | 5/1998 | Shaknovich |
| 5,749,921 A | 5/1998 | Lenker et al. |
| 5,755,682 A | 5/1998 | Knudson et al. |
| 5,755,777 A | 5/1998 | Chuter |
| 5,755,783 A | 5/1998 | Stobie et al. |
| 5,756,476 A | 5/1998 | Epstein et al. |
| 5,758,663 A | 6/1998 | Wilk et al. |
| 5,766,151 A | 6/1998 | Valley et al. |
| 5,769,780 A | 6/1998 | Hata et al. |
| 5,769,812 A | 6/1998 | Stevens et al. |
| 5,769,882 A | 6/1998 | Fogarty et al. |
| 5,769,887 A | 6/1998 | Brown et al. |
| 5,772,609 A | 6/1998 | Nguyen et al. |
| 5,776,188 A | 7/1998 | Shepherd et al. |
| 5,782,809 A | 7/1998 | Umeno et al. |
| 5,782,904 A | 7/1998 | White et al. |
| 5,795,331 A | 8/1998 | Cragg et al. |
| 5,797,946 A | 8/1998 | Chin |
| 5,797,960 A | 8/1998 | Stevens et al. |
| 5,799,661 A | 9/1998 | Boyd et al. |
| 5,800,456 A | 9/1998 | Maeda et al. |
| 5,800,508 A | 9/1998 | Goicoechea et al. |
| 5,800,531 A | 9/1998 | Cosgrove et al. |
| 5,807,327 A | 9/1998 | Green et al. |
| 5,807,384 A | 9/1998 | Mueller |
| 5,807,405 A | 9/1998 | Vanney et al. |
| 5,810,836 A | 9/1998 | Hussein et al. |
| 5,814,016 A | 9/1998 | Valley et al. |
| 5,817,113 A | 10/1998 | Gifford, III et al. |
| 5,817,126 A | 10/1998 | Imran |
| 5,823,956 A | 10/1998 | Roth et al. |
| 5,824,037 A | 10/1998 | Fogarty et al. |
| 5,824,038 A | 10/1998 | Wall |
| 5,824,041 A | 10/1998 | Lenker et al. |
| 5,824,043 A | 10/1998 | Cottone, Jr. |
| 5,824,053 A | 10/1998 | Khosravi et al. |
| 5,824,055 A | 10/1998 | Spiridigliozzi et al. |
| 5,824,056 A | 10/1998 | Rosenberg |
| 5,824,061 A | 10/1998 | Quijano et al. |
| 5,824,063 A | 10/1998 | Cox |
| 5,824,064 A | 10/1998 | Taheri |
| 5,824,071 A | 10/1998 | Nelson et al. |
| 5,824,080 A | 10/1998 | Lamuraglia |
| 5,829,447 A | 11/1998 | Stevens et al. |
| 5,830,222 A | 11/1998 | Makower |
| 5,836,869 A | 11/1998 | Kudo et al. |
| 5,840,081 A | 11/1998 | Andersen et al. |
| 5,841,382 A | 11/1998 | Walden et al. |
| 5,843,158 A | 12/1998 | Lenker et al. |
| 5,843,161 A | 12/1998 | Solovay |
| 5,843,181 A | 12/1998 | Jaffe et al. |
| 5,851,232 A | 12/1998 | Lois |
| 5,853,419 A | 12/1998 | Imran |
| 5,853,420 A | 12/1998 | Chevillon et al. |
| 5,855,210 A | 1/1999 | Sterman et al. |
| 5,855,597 A | 1/1999 | Jayaraman |
| 5,855,600 A | 1/1999 | Alt |
| 5,855,601 A | 1/1999 | Bessler et al. |
| 5,855,602 A | 1/1999 | Angell |
| 5,860,966 A | 1/1999 | Tower |
| 5,860,996 A | 1/1999 | Urban et al. |
| 5,861,024 A | 1/1999 | Rashidi |
| 5,861,028 A | 1/1999 | Angell |
| 5,865,723 A | 2/1999 | Love |
| 5,868,783 A | 2/1999 | Tower |
| 5,873,812 A | 2/1999 | Ciana et al. |
| 5,873,906 A | 2/1999 | Lau et al. |
| 5,876,373 A | 3/1999 | Giba et al. |
| 5,876,419 A | 3/1999 | Carpenter et al. |
| 5,876,434 A | 3/1999 | Flomenblit et al. |
| 5,876,448 A | 3/1999 | Thompson et al. |
| 5,878,751 A | 3/1999 | Hussein et al. |
| 5,880,242 A | 3/1999 | Hu et al. |
| 5,885,228 A | 3/1999 | Rosenman et al. |
| 5,885,238 A | 3/1999 | Stevens et al. |
| 5,885,259 A | 3/1999 | Berg |
| 5,888,201 A | 3/1999 | Stinson et al. |
| 5,891,160 A | 4/1999 | Williamson, IV et al. |
| 5,891,191 A | 4/1999 | Stinson |
| 5,895,399 A | 4/1999 | Barbut et al. |
| 5,895,420 A | 4/1999 | Mirsch, II et al. |
| 5,899,936 A | 5/1999 | Goldstein |
| 5,906,619 A | 5/1999 | Olson et al. |
| 5,907,893 A | 6/1999 | Zadno-Azizi et al. |
| 5,908,028 A | 6/1999 | Wilk |
| 5,908,029 A | 6/1999 | Knudson et al. |
| 5,908,451 A | 6/1999 | Yeo |
| 5,908,452 A | 6/1999 | Bokros et al. |
| 5,910,144 A | 6/1999 | Hayashi |
| 5,910,154 A | 6/1999 | Tsugita et al. |
| 5,911,734 A | 6/1999 | Tsugita et al. |
| 5,911,752 A | 6/1999 | Dustrude et al. |
| 5,913,842 A | 6/1999 | Boyd et al. |
| 5,916,193 A | 6/1999 | Stevens et al. |
| 5,922,022 A | 7/1999 | Nash et al. |
| 5,924,424 A | 7/1999 | Stevens et al. |
| 5,925,012 A | 7/1999 | Murphy-Chutorian et al. |
| 5,925,063 A | 7/1999 | Khosravi |
| 5,928,281 A | 7/1999 | Huynh et al. |
| 5,931,848 A | 8/1999 | Saadat |
| 5,935,119 A | 8/1999 | Guy et al. |
| 5,935,161 A | 8/1999 | Robinson et al. |
| 5,935,163 A | 8/1999 | Gabbay |
| 5,938,632 A | 8/1999 | Ellis |
| 5,938,697 A | 8/1999 | Killion et al. |
| 5,941,908 A | 8/1999 | Goldsteen et al. |
| 5,944,019 A | 8/1999 | Knudson et al. |
| 5,944,738 A | 8/1999 | Amplatz et al. |
| 5,948,017 A | 9/1999 | Taheri |
| 5,954,764 A | 9/1999 | Parodi |
| 5,954,766 A | 9/1999 | Zadno-Azizi et al. |
| 5,957,949 A | 9/1999 | Leonhardt et al. |
| 5,961,549 A | 10/1999 | Nguyen et al. |
| 5,964,405 A | 10/1999 | Benary et al. |
| 5,964,798 A | 10/1999 | Imran |
| 5,968,064 A | 10/1999 | Selmon et al. |
| 5,968,068 A | 10/1999 | Dehdashtian et al. |
| 5,968,070 A | 10/1999 | Bley et al. |

(56) References Cited

U.S. PATENT DOCUMENTS

| | | |
|---|---|---|
| 5,971,993 A | 10/1999 | Hussein et al. |
| 5,975,949 A | 11/1999 | Holliday et al. |
| 5,976,153 A | 11/1999 | Fischell et al. |
| 5,976,155 A | 11/1999 | Foreman et al. |
| 5,976,174 A | 11/1999 | Ruiz |
| 5,976,178 A | 11/1999 | Goldsteen et al. |
| 5,976,192 A | 11/1999 | McIntyre et al. |
| 5,976,650 A | 11/1999 | Campbell et al. |
| 5,979,455 A | 11/1999 | Maginot |
| 5,980,455 A | 11/1999 | Daniel et al. |
| 5,980,533 A | 11/1999 | Holman |
| 5,980,548 A | 11/1999 | Evans et al. |
| 5,984,956 A | 11/1999 | Tweden et al. |
| 5,984,957 A | 11/1999 | Laptewicz, Jr. et al. |
| 5,984,959 A | 11/1999 | Robertson et al. |
| 5,984,964 A | 11/1999 | Roberts et al. |
| 5,987,344 A | 11/1999 | West |
| 5,989,276 A | 11/1999 | Houser et al. |
| 5,989,287 A | 11/1999 | Yang et al. |
| 5,993,469 A | 11/1999 | McKenzie et al. |
| 5,993,481 A | 11/1999 | Marcade et al. |
| 5,997,525 A | 12/1999 | March et al. |
| 5,997,557 A | 12/1999 | Barbut et al. |
| 5,997,563 A | 12/1999 | Kretzers |
| 5,997,573 A | 12/1999 | Quijano et al. |
| 5,999,678 A | 12/1999 | Murphy-Chutorian et al. |
| 6,001,123 A | 12/1999 | Lau |
| 6,001,126 A | 12/1999 | Nguyen-Thien-Nhon |
| 6,004,261 A | 12/1999 | Sinofsky et al. |
| 6,004,347 A | 12/1999 | McNamara et al. |
| 6,004,348 A | 12/1999 | Banas et al. |
| 6,007,543 A | 12/1999 | Ellis et al. |
| 6,010,449 A | 1/2000 | Selmon et al. |
| 6,010,522 A | 1/2000 | Barbut et al. |
| 6,010,530 A | 1/2000 | Goicoechea |
| 6,010,531 A | 1/2000 | Donlon et al. |
| 6,012,457 A | 1/2000 | Lesh |
| 6,013,854 A | 1/2000 | Moriuchi |
| 6,015,431 A | 1/2000 | Thornton et al. |
| 6,019,777 A | 2/2000 | Mackenzie |
| 6,019,778 A | 2/2000 | Wilson et al. |
| 6,022,370 A | 2/2000 | Tower |
| 6,026,814 A | 2/2000 | LaFontaine et al. |
| 6,027,476 A | 2/2000 | Sterman et al. |
| 6,027,520 A | 2/2000 | Tsugita et al. |
| 6,027,525 A | 2/2000 | Suh et al. |
| 6,029,671 A | 2/2000 | Stevens et al. |
| 6,029,672 A | 2/2000 | Vanney et al. |
| 6,033,582 A | 3/2000 | Lee et al. |
| 6,035,856 A | 3/2000 | LaFontaine et al. |
| 6,036,677 A | 3/2000 | Javier, Jr. et al. |
| 6,036,697 A | 3/2000 | DiCaprio |
| 6,042,554 A | 3/2000 | Rosenman et al. |
| 6,042,581 A | 3/2000 | Ryan et al. |
| 6,042,589 A | 3/2000 | Marianne |
| 6,042,598 A | 3/2000 | Tsugita et al. |
| 6,042,607 A | 3/2000 | Williamson, IV et al. |
| 6,045,565 A | 4/2000 | Ellis et al. |
| 6,051,014 A | 4/2000 | Jang |
| 6,051,104 A | 4/2000 | Oriaran et al. |
| 6,053,924 A | 4/2000 | Hussein |
| 6,053,942 A | 4/2000 | Eno et al. |
| 6,056,743 A | 5/2000 | Ellis et al. |
| 6,059,809 A | 5/2000 | Amor et al. |
| 6,059,827 A | 5/2000 | Fenton, Jr. |
| 6,066,160 A | 5/2000 | Colvin et al. |
| 6,067,988 A | 5/2000 | Mueller |
| 6,068,638 A | 5/2000 | Makower |
| 6,071,292 A | 6/2000 | Makower et al. |
| 6,074,416 A | 6/2000 | Berg et al. |
| 6,074,417 A | 6/2000 | Peredo |
| 6,074,418 A | 6/2000 | Buchanan et al. |
| 6,076,529 A | 6/2000 | Vanney et al. |
| 6,076,742 A | 6/2000 | Benary |
| 6,077,297 A | 6/2000 | Robinson et al. |
| 6,079,414 A | 6/2000 | Roth |
| 6,080,163 A | 6/2000 | Hussein et al. |
| 6,080,170 A | 6/2000 | Nash et al. |
| 6,083,257 A | 7/2000 | Taylor et al. |
| 6,091,042 A | 7/2000 | Benary |
| 6,092,526 A | 7/2000 | LaFontaine et al. |
| 6,092,529 A | 7/2000 | Cox |
| 6,093,166 A | 7/2000 | Knudson et al. |
| 6,093,177 A | 7/2000 | Javier, Jr. et al. |
| 6,093,185 A | 7/2000 | Ellis et al. |
| 6,093,203 A | 7/2000 | Uflacker |
| 6,093,530 A | 7/2000 | McIlroy et al. |
| 6,096,074 A | 8/2000 | Pedros |
| 6,102,941 A | 8/2000 | Tweden et al. |
| 6,102,944 A | 8/2000 | Huynh et al. |
| 6,106,550 A | 8/2000 | Magovern et al. |
| 6,110,191 A | 8/2000 | Dehdashtian et al. |
| 6,110,198 A | 8/2000 | Fogarty et al. |
| 6,110,201 A | 8/2000 | Quijano et al. |
| 6,113,612 A | 9/2000 | Swanson et al. |
| 6,113,630 A | 9/2000 | Vanney et al. |
| 6,113,823 A | 9/2000 | Eno |
| 6,117,169 A | 9/2000 | Moe |
| 6,120,520 A | 9/2000 | Saadat et al. |
| 6,120,534 A | 9/2000 | Ruiz |
| 6,123,682 A | 9/2000 | Knudson et al. |
| 6,123,723 A | 9/2000 | Konya et al. |
| 6,125,852 A | 10/2000 | Stevens et al. |
| 6,126,649 A | 10/2000 | Vantassel et al. |
| 6,126,654 A | 10/2000 | Giba et al. |
| 6,126,685 A | 10/2000 | Lenker et al. |
| 6,126,686 A | 10/2000 | Badylak et al. |
| 6,132,451 A | 10/2000 | Payne et al. |
| 6,132,473 A | 10/2000 | Williams et al. |
| 6,132,986 A | 10/2000 | Pathak et al. |
| 6,139,510 A | 10/2000 | Palermo |
| 6,139,541 A | 10/2000 | Vanney et al. |
| 6,142,987 A | 11/2000 | Tsugita |
| 6,143,021 A | 11/2000 | Staehle |
| 6,143,987 A | 11/2000 | Makita |
| 6,146,366 A | 11/2000 | Schachar |
| 6,146,415 A | 11/2000 | Fitz |
| 6,146,417 A | 11/2000 | Ischinger |
| 6,152,937 A | 11/2000 | Peterson et al. |
| 6,152,956 A | 11/2000 | Pierce |
| 6,155,264 A | 12/2000 | Ressemann et al. |
| 6,156,031 A | 12/2000 | Aita et al. |
| 6,156,055 A | 12/2000 | Ravenscroft |
| 6,156,531 A | 12/2000 | Pathak et al. |
| 6,157,852 A | 12/2000 | Selmon et al. |
| 6,159,225 A | 12/2000 | Makower |
| 6,159,239 A | 12/2000 | Greenhalgh |
| 6,162,208 A | 12/2000 | Hipps |
| 6,162,245 A | 12/2000 | Jayaraman |
| 6,165,185 A | 12/2000 | Shennib et al. |
| 6,165,188 A | 12/2000 | Saadat et al. |
| 6,165,200 A | 12/2000 | Tsugita et al. |
| 6,165,209 A | 12/2000 | Patterson et al. |
| 6,167,605 B1 | 1/2001 | Morales |
| 6,168,579 B1 | 1/2001 | Tsugita |
| 6,168,614 B1 | 1/2001 | Andersen et al. |
| 6,168,616 B1 | 1/2001 | Brown, III |
| 6,171,251 B1 | 1/2001 | Mueller et al. |
| 6,171,327 B1 | 1/2001 | Daniel et al. |
| 6,171,335 B1 | 1/2001 | Wheatley et al. |
| 6,177,514 B1 | 1/2001 | Pathak et al. |
| 6,179,859 B1 | 1/2001 | Bates et al. |
| 6,182,664 B1 | 2/2001 | Cosgrove |
| 6,182,668 B1 | 2/2001 | Tweden et al. |
| 6,183,481 B1 | 2/2001 | Lee et al. |
| 6,186,972 B1 | 2/2001 | Nelson et al. |
| 6,187,016 B1 | 2/2001 | Hedges et al. |
| 6,190,353 B1 | 2/2001 | Makower et al. |
| 6,190,393 B1 | 2/2001 | Bevier et al. |
| 6,190,405 B1 | 2/2001 | Culombo et al. |
| 6,193,726 B1 | 2/2001 | Vanney |
| 6,193,734 B1 | 2/2001 | Bolduc et al. |
| 6,196,230 B1 | 3/2001 | Hall et al. |
| 6,197,050 B1 | 3/2001 | Eno et al. |

(56) References Cited

U.S. PATENT DOCUMENTS

| | | |
|---|---|---|
| 6,197,053 B1 | 3/2001 | Cosgrove et al. |
| 6,197,296 B1 | 3/2001 | Davies et al. |
| 6,197,324 B1 | 3/2001 | Crittenden |
| 6,200,311 B1 | 3/2001 | Danek et al. |
| 6,200,336 B1 | 3/2001 | Pavcnik et al. |
| 6,203,550 B1 | 3/2001 | Olson |
| 6,203,556 B1 | 3/2001 | Evans et al. |
| 6,206,888 B1 | 3/2001 | Bicek et al. |
| 6,206,911 B1 | 3/2001 | Milo |
| 6,210,408 B1 | 4/2001 | Chandrasekaran et al. |
| 6,210,957 B1 | 4/2001 | Carpentier et al. |
| 6,213,126 B1 | 4/2001 | LaFontaine et al. |
| 6,214,036 B1 | 4/2001 | Letendre et al. |
| 6,214,041 B1 | 4/2001 | Tweden et al. |
| 6,214,054 B1 | 4/2001 | Cunanan et al. |
| 6,214,055 B1 | 4/2001 | Simionescu et al. |
| 6,217,527 B1 | 4/2001 | Selmon et al. |
| 6,217,549 B1 | 4/2001 | Selmon et al. |
| 6,217,575 B1 | 4/2001 | DeVore et al. |
| 6,217,609 B1 | 4/2001 | Haverkost |
| 6,218,662 B1 | 4/2001 | Tchakarov et al. |
| 6,221,006 B1 | 4/2001 | Dubrul et al. |
| 6,221,049 B1 | 4/2001 | Selmon et al. |
| 6,221,091 B1 | 4/2001 | Khosravi |
| 6,221,096 B1 | 4/2001 | Aiba et al. |
| 6,221,100 B1 | 4/2001 | Strecker |
| 6,223,752 B1 | 5/2001 | Vanney et al. |
| 6,224,584 B1 | 5/2001 | March et al. |
| 6,231,544 B1 | 5/2001 | Tsugita et al. |
| 6,231,546 B1 | 5/2001 | Milo et al. |
| 6,231,551 B1 | 5/2001 | Barbut |
| 6,231,587 B1 | 5/2001 | Makower |
| 6,231,602 B1 | 5/2001 | Carpentier et al. |
| 6,235,000 B1 | 5/2001 | Milo et al. |
| 6,237,607 B1 | 5/2001 | Vanney et al. |
| 6,238,406 B1 | 5/2001 | Ellis et al. |
| 6,241,667 B1 | 6/2001 | Vetter et al. |
| 6,241,738 B1 | 6/2001 | Dereume |
| 6,241,741 B1 | 6/2001 | Duhaylongsod et al. |
| 6,241,757 B1 | 6/2001 | An et al. |
| 6,245,102 B1 | 6/2001 | Jayaraman |
| 6,245,103 B1 | 6/2001 | Stinson |
| 6,245,105 B1 | 6/2001 | Nguyen et al. |
| 6,248,112 B1 | 6/2001 | Gambale et al. |
| 6,248,116 B1 | 6/2001 | Chevillon et al. |
| 6,250,305 B1 | 6/2001 | Tweden |
| 6,251,079 B1 | 6/2001 | Gambale et al. |
| 6,251,104 B1 | 6/2001 | Kesten et al. |
| 6,251,116 B1 | 6/2001 | Shennib et al. |
| 6,251,135 B1 | 6/2001 | Stinson et al. |
| 6,251,418 B1 | 6/2001 | Ahern et al. |
| 6,253,768 B1 | 7/2001 | Wilk |
| 6,253,769 B1 | 7/2001 | LaFontaine et al. |
| 6,254,564 B1 | 7/2001 | Wilk et al. |
| 6,254,635 B1 | 7/2001 | Schroeder et al. |
| 6,254,636 B1 | 7/2001 | Peredo |
| 6,257,634 B1 | 7/2001 | Wei |
| 6,258,052 B1 | 7/2001 | Milo |
| 6,258,087 B1 | 7/2001 | Edwards et al. |
| 6,258,114 B1 | 7/2001 | Konya et al. |
| 6,258,115 B1 | 7/2001 | Dubrul |
| 6,258,119 B1 | 7/2001 | Hussein et al. |
| 6,258,120 B1 | 7/2001 | McKenzie et al. |
| 6,258,129 B1 | 7/2001 | Dybdal et al. |
| 6,258,150 B1 | 7/2001 | Mackellar |
| 6,261,304 B1 | 7/2001 | Hall et al. |
| 6,267,783 B1 | 7/2001 | Letendre et al. |
| 6,269,819 B1 | 8/2001 | Oz et al. |
| 6,270,513 B1 | 8/2001 | Tsugita et al. |
| 6,270,521 B1 | 8/2001 | Fischell et al. |
| 6,270,526 B1 | 8/2001 | Cox |
| 6,273,876 B1 | 8/2001 | Klima et al. |
| 6,273,895 B1 | 8/2001 | Pinchuk et al. |
| 6,276,661 B1 | 8/2001 | Laird |
| 6,277,555 B1 | 8/2001 | Duran et al. |
| 6,283,127 B1 | 9/2001 | Sterman et al. |
| 6,283,951 B1 | 9/2001 | Flaherty et al. |
| 6,283,983 B1 | 9/2001 | Makower et al. |
| 6,283,995 B1 | 9/2001 | Moe et al. |
| 6,285,903 B1 | 9/2001 | Rosenthal et al. |
| 6,287,317 B1 | 9/2001 | Makower et al. |
| 6,287,334 B1 | 9/2001 | Moll et al. |
| 6,287,338 B1 | 9/2001 | Sarnowski et al. |
| 6,287,339 B1 | 9/2001 | Vazquez et al. |
| 6,290,709 B1 | 9/2001 | Ellis et al. |
| 6,290,728 B1 | 9/2001 | Phelps et al. |
| 6,296,662 B1 | 10/2001 | Caffey |
| 6,299,637 B1 | 10/2001 | Shaolian et al. |
| 6,302,875 B1 | 10/2001 | Makower et al. |
| 6,302,892 B1 | 10/2001 | Wilk |
| 6,302,906 B1 | 10/2001 | Goicoechea et al. |
| 6,306,164 B1 | 10/2001 | Kujawski |
| 6,309,382 B1 | 10/2001 | Garrison et al. |
| 6,309,417 B1 | 10/2001 | Spence et al. |
| 6,311,693 B1 | 11/2001 | Sterman et al. |
| 6,312,465 B1 | 11/2001 | Griffin et al. |
| 6,319,281 B1 | 11/2001 | Patel |
| 6,322,548 B1 | 11/2001 | Payne et al. |
| 6,322,593 B1 | 11/2001 | Pathak et al. |
| 6,325,067 B1 | 12/2001 | Sterman et al. |
| 6,327,772 B1 | 12/2001 | Zadno-Azizi et al. |
| 6,330,884 B1 | 12/2001 | Kim |
| 6,331,189 B1 | 12/2001 | Wolinsky et al. |
| 6,334,873 B1 | 1/2002 | Lane et al. |
| 6,336,934 B1 | 1/2002 | Gilson et al. |
| 6,336,937 B1 | 1/2002 | Vonesh et al. |
| 6,338,735 B1 | 1/2002 | Stevens |
| 6,338,740 B1 | 1/2002 | Carpentier |
| 6,342,070 B1 | 1/2002 | Nguyen-Thien-Nhon |
| 6,344,044 B1 | 2/2002 | Fulkerson et al. |
| 6,346,074 B1 | 2/2002 | Roth |
| 6,346,116 B1 | 2/2002 | Brooks et al. |
| 6,348,063 B1 | 2/2002 | Yassour et al. |
| 6,350,248 B1 | 2/2002 | Knudson et al. |
| 6,350,277 B1 | 2/2002 | Kocur |
| 6,350,278 B1 | 2/2002 | Lenker et al. |
| 6,352,547 B1 | 3/2002 | Brown et al. |
| 6,352,554 B2 | 3/2002 | De Paulis |
| 6,352,708 B1 | 3/2002 | Duran et al. |
| 6,357,104 B1 | 3/2002 | Myers |
| 6,358,277 B1 | 3/2002 | Duran |
| 6,361,519 B1 | 3/2002 | Knudson et al. |
| 6,361,545 B1 | 3/2002 | Macoviak et al. |
| 6,363,938 B2 | 4/2002 | Saadat et al. |
| 6,363,939 B1 | 4/2002 | Wilk |
| 6,364,895 B1 | 4/2002 | Greenhalgh |
| 6,368,338 B1 | 4/2002 | Konya et al. |
| 6,371,970 B1 | 4/2002 | Khosravi et al. |
| 6,371,983 B1 | 4/2002 | Lane |
| 6,375,615 B1 | 4/2002 | Flaherty et al. |
| 6,378,221 B1 | 4/2002 | Ekholm, Jr. et al. |
| 6,379,319 B1 | 4/2002 | Garibotto et al. |
| 6,379,365 B1 | 4/2002 | Diaz |
| 6,379,372 B1 | 4/2002 | Dehdashtian et al. |
| 6,379,383 B1 | 4/2002 | Palmaz et al. |
| 6,379,740 B1 | 4/2002 | Rinaldi et al. |
| 6,380,457 B1 | 4/2002 | Yurek et al. |
| 6,383,193 B1 | 5/2002 | Cathcart et al. |
| 6,387,119 B2 | 5/2002 | Wolf et al. |
| 6,387,122 B1 | 5/2002 | Cragg |
| 6,390,098 B1 | 5/2002 | LaFontaine et al. |
| 6,391,051 B2 | 5/2002 | Sullivan, III et al. |
| 6,391,538 B1 | 5/2002 | Vyavahare et al. |
| 6,395,208 B1 | 5/2002 | Herweck et al. |
| 6,398,807 B1 | 6/2002 | Chouinard et al. |
| 6,401,720 B1 | 6/2002 | Stevens et al. |
| 6,402,736 B1 | 6/2002 | Brown et al. |
| 6,402,740 B1 | 6/2002 | Ellis et al. |
| 6,406,488 B1 | 6/2002 | Tweden et al. |
| 6,406,491 B1 | 6/2002 | Vanney |
| 6,406,493 B1 | 6/2002 | Tu et al. |
| 6,409,697 B2 | 6/2002 | Eno et al. |
| 6,409,750 B1 | 6/2002 | Hyodoh et al. |
| 6,409,751 B1 | 6/2002 | Hall et al. |

(56) References Cited

U.S. PATENT DOCUMENTS

| | | |
|---|---|---|
| 6,409,755 B1 | 6/2002 | Vrba |
| 6,409,759 B1 | 6/2002 | Peredo |
| 6,413,275 B1 | 7/2002 | Nguyen et al. |
| 6,416,490 B1 | 7/2002 | Ellis et al. |
| 6,416,510 B1 | 7/2002 | Altman et al. |
| 6,423,089 B1 | 7/2002 | Gingras et al. |
| 6,425,916 B1 | 7/2002 | Garrison et al. |
| 6,432,119 B1 | 8/2002 | Saadat |
| 6,432,126 B1 | 8/2002 | Gambale et al. |
| 6,432,127 B1 | 8/2002 | Kim et al. |
| 6,432,132 B1 | 8/2002 | Cottone et al. |
| 6,440,164 B1 | 8/2002 | DiMatteo et al. |
| 6,443,158 B1 | 9/2002 | LaFontaine et al. |
| 6,447,522 B2 | 9/2002 | Gambale et al. |
| 6,447,539 B1 | 9/2002 | Nelson et al. |
| 6,451,025 B1 | 9/2002 | Jervis |
| 6,451,054 B1 | 9/2002 | Stevens |
| 6,454,760 B2 | 9/2002 | Vanney |
| 6,454,794 B1 | 9/2002 | Knudson et al. |
| 6,454,799 B1 | 9/2002 | Schreck |
| 6,458,092 B1 | 10/2002 | Gambale et al. |
| 6,458,140 B2 | 10/2002 | Akin et al. |
| 6,458,153 B1 | 10/2002 | Bailey et al. |
| 6,458,323 B1 | 10/2002 | Boekstegers |
| 6,461,382 B1 | 10/2002 | Cao |
| 6,464,709 B2 | 10/2002 | Shennib et al. |
| 6,468,303 B1 | 10/2002 | Amplatz et al. |
| 6,468,660 B2 | 10/2002 | Ogle et al. |
| 6,471,723 B1 | 10/2002 | Ashworth et al. |
| 6,475,169 B2 | 11/2002 | Ferrera |
| 6,475,226 B1 | 11/2002 | Belef et al. |
| 6,475,239 B1 | 11/2002 | Campbell et al. |
| 6,475,244 B2 | 11/2002 | Herweck et al. |
| 6,478,819 B2 | 11/2002 | Moe |
| 6,479,079 B1 | 11/2002 | Pathak et al. |
| 6,482,220 B1 | 11/2002 | Mueller |
| 6,482,228 B1 | 11/2002 | Norred |
| 6,485,501 B1 | 11/2002 | Green |
| 6,485,502 B2 | 11/2002 | Don Michael et al. |
| 6,485,513 B1 | 11/2002 | Fan |
| 6,485,524 B2 | 11/2002 | Strecker |
| 6,487,581 B1 | 11/2002 | Spence et al. |
| 6,488,704 B1 | 12/2002 | Connelly et al. |
| 6,491,689 B1 | 12/2002 | Ellis et al. |
| 6,491,707 B2 | 12/2002 | Makower et al. |
| 6,494,211 B1 | 12/2002 | Boyd et al. |
| 6,494,897 B2 | 12/2002 | Sterman et al. |
| 6,494,909 B2 | 12/2002 | Greenhalgh |
| 6,503,272 B2 | 1/2003 | Duerig et al. |
| 6,508,496 B1 | 1/2003 | Huang |
| 6,508,803 B1 | 1/2003 | Horikawa et al. |
| 6,508,825 B1 | 1/2003 | Selmon et al. |
| 6,508,833 B2 | 1/2003 | Pavcnik et al. |
| 6,509,145 B1 | 1/2003 | Torrianni |
| 6,511,458 B2 | 1/2003 | Milo et al. |
| 6,511,491 B2 | 1/2003 | Grudem et al. |
| 6,514,217 B1 | 2/2003 | Selmon et al. |
| 6,514,271 B2 | 2/2003 | Evans et al. |
| 6,517,527 B2 | 2/2003 | Gambale et al. |
| 6,517,558 B2 | 2/2003 | Gittings et al. |
| 6,517,573 B1 | 2/2003 | Pollock et al. |
| 6,521,179 B1 | 2/2003 | Girardot et al. |
| 6,524,323 B1 | 2/2003 | Nash et al. |
| 6,524,335 B1 | 2/2003 | Hartley et al. |
| 6,527,800 B1 | 3/2003 | McGuckin, Jr. et al. |
| 6,530,949 B2 | 3/2003 | Konya et al. |
| 6,530,952 B2 | 3/2003 | Vesely |
| 6,533,807 B2 | 3/2003 | Wolinsky et al. |
| 6,537,297 B2 | 3/2003 | Tsugita et al. |
| 6,537,310 B1 | 3/2003 | Palmaz et al. |
| 6,540,768 B1 | 4/2003 | Diaz et al. |
| 6,540,782 B1 | 4/2003 | Snyders |
| 6,544,230 B1 | 4/2003 | Flaherty et al. |
| 6,547,827 B2 | 4/2003 | Carpentier et al. |
| 6,551,303 B1 | 4/2003 | Van Tassel et al. |
| 6,558,318 B1 | 5/2003 | Daniel et al. |
| 6,558,417 B2 | 5/2003 | Peredo |
| 6,558,418 B2 | 5/2003 | Carpentier et al. |
| 6,558,429 B2 | 5/2003 | Taylor |
| 6,559,132 B1 | 5/2003 | Holmer |
| 6,561,998 B1 | 5/2003 | Roth et al. |
| 6,562,031 B2 | 5/2003 | Chandrasekaran et al. |
| 6,562,058 B2 | 5/2003 | Seguin et al. |
| 6,562,063 B1 | 5/2003 | Euteneuer et al. |
| 6,562,069 B2 | 5/2003 | Cai et al. |
| 6,564,805 B2 | 5/2003 | Garrison et al. |
| 6,565,528 B1 | 5/2003 | Mueller |
| 6,565,594 B1 | 5/2003 | Herweck et al. |
| 6,569,145 B1 | 5/2003 | Shmulewitz et al. |
| 6,569,147 B1 | 5/2003 | Evans et al. |
| 6,569,196 B1 | 5/2003 | Vesely |
| 6,572,593 B1 | 6/2003 | Daum |
| 6,572,642 B2 | 6/2003 | Rinaldi et al. |
| 6,572,643 B1 | 6/2003 | Gharibadeh |
| 6,572,652 B2 | 6/2003 | Shaknovich |
| 6,575,168 B2 | 6/2003 | LaFontaine et al. |
| 6,579,311 B1 | 6/2003 | Makower |
| 6,582,444 B2 | 6/2003 | Wilk |
| 6,582,460 B1 | 6/2003 | Cryer |
| 6,582,462 B1 | 6/2003 | Andersen et al. |
| 6,585,756 B1 | 7/2003 | Strecker |
| 6,585,758 B1 | 7/2003 | Chouinard et al. |
| 6,585,766 B1 | 7/2003 | Huynh et al. |
| 6,589,279 B1 | 7/2003 | Anderson et al. |
| 6,592,546 B1 | 7/2003 | Barbut et al. |
| 6,592,614 B2 | 7/2003 | Lenker et al. |
| 6,599,304 B1 | 7/2003 | Selmon et al. |
| 6,600,803 B2 | 7/2003 | Bruder et al. |
| 6,605,053 B1 | 8/2003 | Kamm et al. |
| 6,605,112 B1 | 8/2003 | Moll et al. |
| 6,605,113 B2 | 8/2003 | Wilk |
| 6,608,040 B1 | 8/2003 | Lin et al. |
| 6,610,077 B1 | 8/2003 | Hancock et al. |
| 6,610,085 B1 | 8/2003 | Lazarus |
| 6,610,100 B2 | 8/2003 | Phelps et al. |
| 6,613,069 B2 | 9/2003 | Boyd et al. |
| 6,613,077 B2 | 9/2003 | Gilligan et al. |
| 6,613,079 B1 | 9/2003 | Wolinsky et al. |
| 6,613,081 B2 | 9/2003 | Kim et al. |
| 6,613,086 B1 | 9/2003 | Moe et al. |
| 6,616,675 B1 | 9/2003 | Evard et al. |
| 6,616,682 B2 | 9/2003 | Joergensen et al. |
| 6,622,604 B1 | 9/2003 | Chouinard et al. |
| 6,623,491 B2 | 9/2003 | Thompson |
| 6,623,518 B2 | 9/2003 | Thompson et al. |
| 6,623,521 B2 | 9/2003 | Steinke et al. |
| 6,626,938 B1 | 9/2003 | Butaric et al. |
| 6,626,939 B1 | 9/2003 | Burnside et al. |
| 6,632,241 B1 | 10/2003 | Hancock et al. |
| 6,632,243 B1 | 10/2003 | Zadno-Azizi et al. |
| 6,632,470 B2 | 10/2003 | Morra et al. |
| 6,635,068 B1 | 10/2003 | Dubrul et al. |
| 6,635,079 B2 | 10/2003 | Unsworth et al. |
| 6,635,080 B1 | 10/2003 | Lauterjung et al. |
| 6,635,085 B1 | 10/2003 | Caffey et al. |
| 6,638,237 B1 | 10/2003 | Guiles et al. |
| 6,638,247 B1 | 10/2003 | Selmon et al. |
| 6,638,293 B1 | 10/2003 | Makower et al. |
| 6,641,610 B2 | 11/2003 | Wolf et al. |
| 6,651,670 B2 | 11/2003 | Rapacki et al. |
| 6,651,672 B2 | 11/2003 | Roth |
| 6,652,540 B1 | 11/2003 | Cole et al. |
| 6,652,546 B1 | 11/2003 | Nash et al. |
| 6,652,555 B1 | 11/2003 | Vantassel et al. |
| 6,652,571 B1 | 11/2003 | White et al. |
| 6,652,578 B2 | 11/2003 | Bailey et al. |
| 6,655,386 B1 | 12/2003 | Makower et al. |
| 6,656,213 B2 | 12/2003 | Solem |
| 6,660,003 B1 | 12/2003 | DeVore et al. |
| 6,660,024 B1 | 12/2003 | Flaherty et al. |
| 6,663,588 B2 | 12/2003 | DuBois et al. |
| 6,663,663 B2 | 12/2003 | Kim et al. |
| 6,663,667 B2 | 12/2003 | Dehdashtian et al. |
| 6,666,863 B2 | 12/2003 | Wentzel et al. |

(56) References Cited

U.S. PATENT DOCUMENTS

| | | |
|---|---|---|
| 6,669,709 B1 | 12/2003 | Cohn et al. |
| 6,669,724 B2 | 12/2003 | Park et al. |
| 6,673,089 B1 | 1/2004 | Yassour et al. |
| 6,673,101 B1 | 1/2004 | Fitzgerald et al. |
| 6,673,106 B2 | 1/2004 | Mitelberg et al. |
| 6,673,109 B2 | 1/2004 | Cox |
| 6,676,668 B2 | 1/2004 | Mercereau et al. |
| 6,676,692 B2 | 1/2004 | Rabkin et al. |
| 6,676,693 B1 | 1/2004 | Belding et al. |
| 6,676,698 B2 | 1/2004 | McGuckin, Jr. et al. |
| 6,679,268 B2 | 1/2004 | Stevens et al. |
| 6,682,543 B2 | 1/2004 | Barbut et al. |
| 6,682,558 B2 | 1/2004 | Tu et al. |
| 6,682,559 B2 | 1/2004 | Myers et al. |
| 6,685,648 B2 | 2/2004 | Flaherty et al. |
| 6,685,739 B2 | 2/2004 | DiMatteo et al. |
| 6,689,144 B2 | 2/2004 | Gerberding |
| 6,689,164 B1 | 2/2004 | Seguin |
| 6,692,512 B2 | 2/2004 | Jang |
| 6,692,513 B2 | 2/2004 | Streeter et al. |
| 6,694,983 B2 | 2/2004 | Wolf et al. |
| 6,695,864 B2 | 2/2004 | Macoviak et al. |
| 6,695,865 B2 | 2/2004 | Boyle et al. |
| 6,695,875 B2 | 2/2004 | Stelter et al. |
| 6,695,878 B2 | 2/2004 | McGuckin, Jr. et al. |
| 6,699,274 B2 | 3/2004 | Stinson |
| 6,701,932 B2 | 3/2004 | Knudson et al. |
| 6,702,851 B1 | 3/2004 | Chinn et al. |
| 6,709,425 B2 | 3/2004 | Gambale et al. |
| 6,709,444 B1 | 3/2004 | Makower |
| 6,712,842 B1 | 3/2004 | Gifford, III et al. |
| 6,712,843 B2 | 3/2004 | Elliott |
| 6,714,841 B1 | 3/2004 | Wright et al. |
| 6,714,842 B1 | 3/2004 | Ito |
| 6,719,770 B2 | 4/2004 | Laufer et al. |
| 6,719,787 B2 | 4/2004 | Cox |
| 6,719,788 B2 | 4/2004 | Cox |
| 6,719,789 B2 | 4/2004 | Cox |
| 6,723,116 B2 | 4/2004 | Taheri |
| 6,723,122 B2 | 4/2004 | Yang et al. |
| 6,726,677 B1 | 4/2004 | Flaherty et al. |
| 6,729,356 B1 | 5/2004 | Baker et al. |
| 6,730,118 B2 | 5/2004 | Spenser et al. |
| 6,730,121 B2 | 5/2004 | Ortiz et al. |
| 6,730,377 B2 | 5/2004 | Wang |
| 6,733,513 B2 | 5/2004 | Boyle et al. |
| 6,733,525 B2 | 5/2004 | Yang et al. |
| 6,736,827 B1 | 5/2004 | McAndrew et al. |
| 6,736,839 B2 | 5/2004 | Cummings |
| 6,736,845 B2 | 5/2004 | Marquez et al. |
| 6,736,846 B2 | 5/2004 | Cox |
| 6,743,252 B1 | 6/2004 | Bates et al. |
| 6,746,464 B1 | 6/2004 | Makower |
| 6,752,828 B2 | 6/2004 | Thornton |
| 6,755,854 B2 | 6/2004 | Gillick et al. |
| 6,755,855 B2 | 6/2004 | Yurek et al. |
| 6,758,855 B2 | 7/2004 | Fulton, III et al. |
| 6,764,503 B1 | 7/2004 | Ishimaru |
| 6,764,509 B2 | 7/2004 | Chinn et al. |
| 6,767,345 B2 | 7/2004 | St. Germain et al. |
| 6,767,362 B2 | 7/2004 | Schreck |
| 6,769,434 B2 | 8/2004 | Liddicoat et al. |
| 6,773,454 B2 | 8/2004 | Wholey et al. |
| 6,773,455 B2 | 8/2004 | Allen et al. |
| 6,773,456 B1 | 8/2004 | Gordon et al. |
| 6,774,278 B1 | 8/2004 | Ragheb et al. |
| 6,776,791 B1 | 8/2004 | Stallings et al. |
| 6,786,925 B1 | 9/2004 | Schoon et al. |
| 6,786,929 B2 | 9/2004 | Gambale et al. |
| 6,790,229 B1 | 9/2004 | Berreklouw |
| 6,790,230 B2 | 9/2004 | Beyersdorf et al. |
| 6,790,237 B2 | 9/2004 | Stinson |
| 6,792,979 B2 | 9/2004 | Konya et al. |
| 6,797,000 B2 | 9/2004 | Simpson et al. |
| 6,797,002 B2 | 9/2004 | Spence et al. |
| 6,802,319 B2 | 10/2004 | Stevens et al. |
| 6,802,858 B2 | 10/2004 | Gambale et al. |
| 6,805,711 B2 | 10/2004 | Quijano et al. |
| 6,808,498 B2 | 10/2004 | Laroya et al. |
| 6,808,504 B2 | 10/2004 | Schorgl et al. |
| 6,808,529 B2 | 10/2004 | Fulkerson |
| 6,814,746 B2 | 11/2004 | Thompson et al. |
| 6,814,754 B2 | 11/2004 | Greenhalgh |
| 6,820,676 B2 | 11/2004 | Palmaz et al. |
| 6,821,211 B2 | 11/2004 | Otten et al. |
| 6,821,297 B2 | 11/2004 | Snyders |
| 6,824,041 B2 | 11/2004 | Grieder et al. |
| 6,824,970 B2 | 11/2004 | Vyavahare et al. |
| 6,830,568 B1 | 12/2004 | Kesten et al. |
| 6,830,575 B2 | 12/2004 | Stenzel et al. |
| 6,830,584 B1 | 12/2004 | Seguin |
| 6,830,585 B1 | 12/2004 | Artof et al. |
| 6,830,586 B2 | 12/2004 | Quijano et al. |
| 6,837,901 B2 | 1/2005 | Rabkin et al. |
| 6,837,902 B2 | 1/2005 | Nguyen et al. |
| 6,840,957 B2 | 1/2005 | DiMatteo et al. |
| 6,843,802 B1 | 1/2005 | Villalobos et al. |
| 6,846,325 B2 | 1/2005 | Liddicoat |
| 6,849,084 B2 | 2/2005 | Rabkin et al. |
| 6,849,085 B2 | 2/2005 | Marton |
| 6,854,467 B2 | 2/2005 | Boekstegers |
| 6,860,898 B2 | 3/2005 | Stack et al. |
| 6,861,211 B2 | 3/2005 | Levy et al. |
| 6,863,668 B2 | 3/2005 | Gillespie et al. |
| 6,863,684 B2 | 3/2005 | Kim et al. |
| 6,863,688 B2 | 3/2005 | Ralph et al. |
| 6,866,650 B2 | 3/2005 | Stevens et al. |
| 6,866,669 B2 | 3/2005 | Buzzard et al. |
| 6,872,223 B2 | 3/2005 | Roberts et al. |
| 6,872,226 B2 | 3/2005 | Cali et al. |
| 6,875,231 B2 | 4/2005 | Anduiza et al. |
| 6,881,199 B2 | 4/2005 | Wilk et al. |
| 6,881,220 B2 | 4/2005 | Edwin et al. |
| 6,883,522 B2 | 4/2005 | Spence et al. |
| 6,887,266 B2 | 5/2005 | Williams et al. |
| 6,890,330 B2 | 5/2005 | Streeter et al. |
| 6,890,340 B2 | 5/2005 | Duane |
| 6,893,459 B1 | 5/2005 | Macoviak |
| 6,893,460 B2 | 5/2005 | Spenser et al. |
| 6,896,690 B1 | 5/2005 | Lambrecht et al. |
| 6,899,704 B2 | 5/2005 | Sterman et al. |
| 6,905,743 B1 | 6/2005 | Chen et al. |
| 6,908,481 B2 | 6/2005 | Cribier |
| 6,911,036 B2 | 6/2005 | Douk et al. |
| 6,911,040 B2 | 6/2005 | Johnson et al. |
| 6,911,043 B2 | 6/2005 | Myers et al. |
| 6,913,021 B2 | 7/2005 | Knudson et al. |
| 6,913,600 B2 | 7/2005 | Valley et al. |
| 6,916,304 B2 | 7/2005 | Eno et al. |
| 6,920,674 B2 | 7/2005 | Thornton |
| 6,920,732 B2 | 7/2005 | Mårtensson |
| 6,926,690 B2 | 8/2005 | Renati |
| 6,926,732 B2 | 8/2005 | Derus et al. |
| 6,929,009 B2 | 8/2005 | Makower et al. |
| 6,929,011 B2 | 8/2005 | Knudson et al. |
| 6,929,653 B2 | 8/2005 | Strecter |
| 6,936,058 B2 | 8/2005 | Forde et al. |
| 6,936,066 B2 | 8/2005 | Palmaz et al. |
| 6,936,067 B2 | 8/2005 | Buchanan |
| 6,939,352 B2 | 9/2005 | Buzzard et al. |
| 6,939,359 B2 | 9/2005 | Tu et al. |
| 6,939,365 B1 | 9/2005 | Fogarty et al. |
| 6,939,370 B2 | 9/2005 | Hartley et al. |
| 6,942,682 B2 | 9/2005 | Vrba et al. |
| 6,945,949 B2 | 9/2005 | Wilk |
| 6,945,997 B2 | 9/2005 | Huynh et al. |
| 6,949,080 B2 | 9/2005 | Wolf et al. |
| 6,949,118 B2 | 9/2005 | Kohler et al. |
| 6,951,571 B1 | 10/2005 | Srivastava |
| 6,953,332 B1 | 10/2005 | Kurk et al. |
| 6,953,481 B2 | 10/2005 | Phelps et al. |
| 6,955,175 B2 | 10/2005 | Stevens et al. |
| 6,955,681 B2 | 10/2005 | Evans et al. |
| 6,964,652 B2 | 11/2005 | Guiles et al. |

(56) References Cited

U.S. PATENT DOCUMENTS

| | | | |
|---|---|---|---|
| 6,964,673 B2 | 11/2005 | Tsugita et al. |
| 6,964,676 B1 | 11/2005 | Gerberding et al. |
| 6,969,395 B2 | 11/2005 | Eskuri |
| 6,972,025 B2 | 12/2005 | Wasdyke |
| 6,972,029 B2 | 12/2005 | Mayrhofer et al. |
| 6,974,464 B2 | 12/2005 | Quijano et al. |
| 6,974,474 B2 | 12/2005 | Pavcnik et al. |
| 6,974,476 B2 | 12/2005 | McGuckin, Jr. et al. |
| 6,976,990 B2 | 12/2005 | Mowry |
| 6,979,350 B2 | 12/2005 | Moll et al. |
| 6,984,242 B2 | 1/2006 | Campbell et al. |
| 6,984,244 B2 | 1/2006 | Perez et al. |
| 6,986,742 B2 | 1/2006 | Hart et al. |
| 6,986,784 B1 | 1/2006 | Weiser et al. |
| 6,988,949 B2 | 1/2006 | Wang |
| 6,989,027 B2 | 1/2006 | Allen et al. |
| 6,989,028 B2 | 1/2006 | Lashinski et al. |
| 6,991,649 B2 | 1/2006 | Sievers |
| 7,001,425 B2 | 2/2006 | McCullagh et al. |
| 7,004,176 B2 | 2/2006 | Lau |
| 7,008,397 B2 | 3/2006 | Tweden et al. |
| 7,011,095 B2 | 3/2006 | Wolf et al. |
| 7,011,681 B2 | 3/2006 | Vesely |
| 7,014,655 B2 | 3/2006 | Barbarash et al. |
| 7,018,401 B1 | 3/2006 | Hyodoh et al. |
| 7,018,406 B2 | 3/2006 | Seguin et al. |
| 7,018,408 B2 | 3/2006 | Bailey et al. |
| 7,022,134 B1 | 4/2006 | Quijano et al. |
| 7,025,773 B2 | 4/2006 | Gittings et al. |
| 7,025,780 B2 | 4/2006 | Gabbay |
| 7,025,791 B2 | 4/2006 | Levine et al. |
| 7,028,692 B2 | 4/2006 | Sterman et al. |
| 7,037,331 B2 | 5/2006 | Mitelberg et al. |
| 7,037,333 B2 | 5/2006 | Myers et al. |
| 7,041,128 B2 | 5/2006 | McGuckin, Jr. et al. |
| 7,041,132 B2 | 5/2006 | Quijano et al. |
| 7,044,966 B2 | 5/2006 | Svanidze et al. |
| 7,048,014 B2 | 5/2006 | Hyodoh et al. |
| 7,048,757 B2 | 5/2006 | Shaknovich |
| 7,050,276 B2 | 5/2006 | Nishiyama |
| 7,074,236 B2 | 7/2006 | Rabkin et al. |
| 7,078,163 B2 | 7/2006 | Torrianni |
| 7,081,132 B2 | 7/2006 | Cook et al. |
| 7,097,658 B2 | 8/2006 | Oktay |
| 7,097,659 B2 | 8/2006 | Woolfson et al. |
| 7,101,396 B2 | 9/2006 | Artof et al. |
| 7,105,016 B2 | 9/2006 | Shiu et al. |
| 7,108,715 B2 | 9/2006 | Lawrence-Brown et al. |
| 7,115,141 B2 | 10/2006 | Menz et al. |
| 7,118,585 B2 | 10/2006 | Addis |
| 7,122,020 B2 | 10/2006 | Mogul |
| 7,125,418 B2 | 10/2006 | Duran et al. |
| 7,128,759 B2 | 10/2006 | Osborne et al. |
| 7,137,184 B2 | 11/2006 | Schreck |
| 7,141,063 B2 | 11/2006 | White et al. |
| 7,141,064 B2 | 11/2006 | Scott et al. |
| 7,143,312 B1 | 11/2006 | Wang et al. |
| 7,147,662 B1 | 12/2006 | Pollock et al. |
| 7,147,663 B1 | 12/2006 | Berg et al. |
| 7,153,324 B2 | 12/2006 | Case et al. |
| 7,160,319 B2 | 1/2007 | Chouinard et al. |
| 7,163,556 B2 | 1/2007 | Xie et al. |
| 7,166,097 B2 | 1/2007 | Barbut |
| 7,175,652 B2 | 2/2007 | Cook et al. |
| 7,175,653 B2 | 2/2007 | Gaber |
| 7,175,654 B2 | 2/2007 | Bonsignore et al. |
| 7,175,656 B2 | 2/2007 | Khairkhahan |
| 7,179,290 B2 | 2/2007 | Cao |
| 7,186,265 B2 | 3/2007 | Sharkawy et al. |
| 7,189,258 B2 | 3/2007 | Johnson et al. |
| 7,189,259 B2 | 3/2007 | Simionescu et al. |
| 7,191,018 B2 | 3/2007 | Gielen et al. |
| 7,191,406 B1 | 3/2007 | Barber et al. |
| 7,195,641 B2 | 3/2007 | Palmaz et al. |
| 7,198,646 B2 | 4/2007 | Figulla et al. |
| 7,201,761 B2 | 4/2007 | Woolfson et al. |
| 7,201,772 B2 | 4/2007 | Schwammenthal et al. |
| 7,214,344 B2 | 5/2007 | Carpentier et al. |
| 7,217,287 B2 | 5/2007 | Wilson et al. |
| 7,235,092 B2 | 6/2007 | Banas et al. |
| 7,235,093 B2 | 6/2007 | Gregorich |
| 7,238,200 B2 | 7/2007 | Lee et al. |
| 7,241,257 B1 | 7/2007 | Ainsworth et al. |
| 7,252,682 B2 | 8/2007 | Seguin |
| 7,258,696 B2 | 8/2007 | Rabkin et al. |
| 7,258,891 B2 | 8/2007 | Pacetti et al. |
| 7,261,732 B2 | 8/2007 | Justino |
| 7,264,632 B2 | 9/2007 | Wright et al. |
| 7,267,686 B2 | 9/2007 | DiMatteo et al. |
| 7,276,078 B2 | 10/2007 | Spenser et al. |
| 7,276,084 B2 | 10/2007 | Yang et al. |
| 7,285,130 B2 | 10/2007 | Austin |
| 7,297,150 B2 | 11/2007 | Cartledge et al. |
| 7,300,457 B2 | 11/2007 | Palmaz |
| 7,300,463 B2 | 11/2007 | Liddicoat |
| 7,311,730 B2 | 12/2007 | Gabbay |
| 7,314,449 B2 | 1/2008 | Pfeiffer et al. |
| 7,314,485 B2 | 1/2008 | Mathis |
| 7,314,880 B2 | 1/2008 | Chang et al. |
| 7,316,706 B2 | 1/2008 | Bloom et al. |
| 7,316,712 B2 | 1/2008 | Peredo |
| 7,317,005 B2 | 1/2008 | Hoekstra et al. |
| 7,317,942 B2 | 1/2008 | Brown |
| 7,317,950 B2 | 1/2008 | Lee |
| 7,318,278 B2 | 1/2008 | Zhang et al. |
| 7,318,998 B2 | 1/2008 | Goldstein et al. |
| 7,319,096 B2 | 1/2008 | Malm et al. |
| 7,320,692 B1 | 1/2008 | Bender et al. |
| 7,320,704 B2 | 1/2008 | Lashinski et al. |
| 7,320,705 B2 | 1/2008 | Quintessenza |
| 7,320,706 B2 | 1/2008 | Al-Najjar |
| 7,322,932 B2 | 1/2008 | Xie et al. |
| 7,323,006 B2 | 1/2008 | Andreas et al. |
| 7,323,066 B1 | 1/2008 | Budron |
| 7,326,174 B2 | 2/2008 | Cox et al. |
| 7,326,219 B2 | 2/2008 | Mowry et al. |
| 7,326,236 B2 | 2/2008 | Andreas et al. |
| 7,327,862 B2 | 2/2008 | Murphy et al. |
| 7,329,278 B2 | 2/2008 | Seguin et al. |
| 7,329,279 B2 | 2/2008 | Haug et al. |
| 7,329,280 B2 | 2/2008 | Bolling et al. |
| 7,329,777 B2 | 2/2008 | Harter et al. |
| 7,331,991 B2 | 2/2008 | Kheradvar et al. |
| 7,331,993 B2 | 2/2008 | White |
| 7,333,643 B2 | 2/2008 | Murphy et al. |
| 7,335,158 B2 | 2/2008 | Taylor |
| 7,335,213 B1 | 2/2008 | Hyde et al. |
| 7,335,218 B2 | 2/2008 | Wilson et al. |
| 7,335,490 B2 | 2/2008 | Van Gilst et al. |
| 7,338,484 B2 | 3/2008 | Schoon et al. |
| 7,338,520 B2 | 3/2008 | Bailey et al. |
| 7,361,189 B2 | 4/2008 | Case et al. |
| 7,361,190 B2 | 4/2008 | Shaoulian et al. |
| 7,364,588 B2 | 4/2008 | Mathis et al. |
| 7,371,258 B2 | 5/2008 | Woo et al. |
| 7,374,560 B2 | 5/2008 | Ressemann et al. |
| 7,374,571 B2 | 5/2008 | Pease et al. |
| 7,377,895 B2 | 5/2008 | Spence et al. |
| 7,377,938 B2 | 5/2008 | Sarac et al. |
| 7,377,940 B2 | 5/2008 | Ryan et al. |
| 7,381,210 B2 | 6/2008 | Zarbatany et al. |
| 7,381,216 B2 | 6/2008 | Buzzard et al. |
| 7,381,218 B2 | 6/2008 | Schreck |
| 7,381,219 B2 | 6/2008 | Salahieh et al. |
| 7,381,220 B2 | 6/2008 | Macoviak et al. |
| 7,384,411 B1 | 6/2008 | Condado |
| 7,387,640 B2 | 6/2008 | Cummings |
| 7,389,874 B2 | 6/2008 | Quest et al. |
| 7,390,325 B2 | 6/2008 | Wang et al. |
| 7,393,358 B2 | 7/2008 | Malewicz |
| 7,393,360 B2 | 7/2008 | Spenser et al. |
| 7,396,364 B2 | 7/2008 | Moaddeb et al. |
| 7,399,315 B2 | 7/2008 | Iobbi |
| 7,402,171 B2 | 7/2008 | Osborne et al. |

(56) References Cited

U.S. PATENT DOCUMENTS

| | | |
|---|---|---|
| 7,404,792 B2 | 7/2008 | Spence et al. |
| 7,404,793 B2 | 7/2008 | Lau et al. |
| 7,405,259 B2 | 7/2008 | Frye et al. |
| 7,410,499 B2 | 8/2008 | Bicer |
| 7,412,274 B2 | 8/2008 | Mejia |
| 7,412,290 B2 | 8/2008 | Janke et al. |
| 7,415,861 B2 | 8/2008 | Sokel |
| 7,416,530 B2 | 8/2008 | Turner et al. |
| 7,422,603 B2 | 9/2008 | Lane |
| 7,422,606 B2 | 9/2008 | Ung-Chhun et al. |
| 7,423,032 B2 | 9/2008 | Ozaki et al. |
| 7,426,413 B2 | 9/2008 | Balczewski et al. |
| 7,427,279 B2 | 9/2008 | Frazier et al. |
| 7,427,287 B2 | 9/2008 | Turovskiy et al. |
| 7,427,291 B2 | 9/2008 | Liddicoat et al. |
| 7,429,269 B2 | 9/2008 | Schwammenthal et al. |
| 7,430,448 B1 | 9/2008 | Zimmer et al. |
| 7,430,484 B2 | 9/2008 | Ohara |
| 7,431,691 B1 | 10/2008 | Wilk |
| 7,431,733 B2 | 10/2008 | Knight |
| 7,435,059 B2 | 10/2008 | Smith et al. |
| 7,435,257 B2 | 10/2008 | Lashinski et al. |
| 7,442,204 B2 | 10/2008 | Schwammenthal et al. |
| RE40,570 E | 11/2008 | Carpentier et al. |
| 7,445,630 B2 | 11/2008 | Lashinski et al. |
| 7,445,631 B2 | 11/2008 | Salahieh et al. |
| 7,445,632 B2 | 11/2008 | McGuckin, Jr. et al. |
| 7,452,371 B2 | 11/2008 | Pavcnik et al. |
| 7,455,689 B2 | 11/2008 | Johnson |
| 7,462,156 B2 | 12/2008 | Mitrev |
| 7,462,184 B2 | 12/2008 | Worley et al. |
| 7,462,191 B2 | 12/2008 | Spenser et al. |
| 7,468,050 B1 | 12/2008 | Kantrowitz |
| 7,470,284 B2 | 12/2008 | Lambrecht et al. |
| 7,470,285 B2 | 12/2008 | Nugent et al. |
| 7,473,271 B2 | 1/2009 | Gunderson |
| 7,473,275 B2 | 1/2009 | Marquez |
| 7,473,417 B2 | 1/2009 | Zeltinger et al. |
| 7,476,196 B2 | 1/2009 | Spence et al. |
| 7,476,199 B2 | 1/2009 | Spence et al. |
| 7,476,200 B2 | 1/2009 | Tal |
| 7,476,244 B2 | 1/2009 | Buzzard et al. |
| 7,481,838 B2 | 1/2009 | Carpentier et al. |
| 7,485,088 B2 | 2/2009 | Murphy et al. |
| 7,485,143 B2 | 2/2009 | Webler et al. |
| 7,488,346 B2 | 2/2009 | Navia |
| 7,491,232 B2 | 2/2009 | Bolduc et al. |
| 7,493,869 B1 | 2/2009 | Foster et al. |
| 7,497,824 B2 | 3/2009 | Taylor |
| 7,500,949 B2 | 3/2009 | Gottlieb et al. |
| 7,500,989 B2 | 3/2009 | Solem et al. |
| 7,503,929 B2 | 3/2009 | Johnson et al. |
| 7,503,930 B2 | 3/2009 | Sharkawy et al. |
| 7,507,199 B2 | 3/2009 | Wang et al. |
| 7,510,572 B2 | 3/2009 | Gabbay |
| 7,510,574 B2 | 3/2009 | Lê et al. |
| 7,510,575 B2 | 3/2009 | Spenser et al. |
| 7,510,577 B2 | 3/2009 | Moaddeb et al. |
| 7,513,863 B2 | 4/2009 | Bolling et al. |
| 7,513,909 B2 | 4/2009 | Lane et al. |
| 7,522,950 B2 | 4/2009 | Fuimaono et al. |
| 7,524,330 B2 | 4/2009 | Berreklouw |
| 7,530,253 B2 | 5/2009 | Spenser et al. |
| 7,530,995 B2 | 5/2009 | Quijano et al. |
| 7,534,261 B2 | 5/2009 | Friedman |
| 7,544,206 B2 | 6/2009 | Cohn |
| 7,547,322 B2 | 6/2009 | Sarac et al. |
| 7,553,324 B2 | 6/2009 | Andreas et al. |
| 7,556,386 B2 | 7/2009 | Smith |
| 7,556,646 B2 | 7/2009 | Yang et al. |
| 7,569,071 B2 | 8/2009 | Haverkost et al. |
| 7,578,828 B2 | 8/2009 | Gittings et al. |
| 7,585,321 B2 | 9/2009 | Cribier |
| 7,591,848 B2 | 9/2009 | Allen |
| 7,594,974 B2 | 9/2009 | Cali et al. |
| 7,601,159 B2 | 10/2009 | Ewers et al. |
| 7,601,195 B2 | 10/2009 | Ichikawa |
| 7,608,099 B2 | 10/2009 | Johnson et al. |
| 7,611,534 B2 | 11/2009 | Kapadia et al. |
| 7,618,446 B2 | 11/2009 | Andersen et al. |
| 7,622,276 B2 | 11/2009 | Cunanan et al. |
| 7,625,403 B2 | 12/2009 | Krivoruchko |
| 7,628,802 B2 | 12/2009 | White et al. |
| 7,628,803 B2 | 12/2009 | Pavcnik et al. |
| 7,632,296 B2 | 12/2009 | Malewicz |
| 7,632,298 B2 | 12/2009 | Hijlkema et al. |
| 7,635,386 B1 | 12/2009 | Gammie |
| 7,641,687 B2 | 1/2010 | Chinn et al. |
| 7,651,519 B2 | 1/2010 | Dittman |
| 7,655,034 B2 | 2/2010 | Mitchell et al. |
| 7,674,282 B2 | 3/2010 | Wu et al. |
| 7,682,390 B2 | 3/2010 | Seguin |
| 7,704,222 B2 | 4/2010 | Wilk et al. |
| 7,704,277 B2 | 4/2010 | Zakay et al. |
| 7,712,606 B2 | 5/2010 | Salahieh et al. |
| 7,715,903 B2 | 5/2010 | Hartley et al. |
| 7,717,955 B2 | 5/2010 | Lane et al. |
| 7,722,638 B2 | 5/2010 | Deyette, Jr. et al. |
| 7,722,662 B2 | 5/2010 | Steinke et al. |
| 7,722,666 B2 | 5/2010 | Lafontaine |
| 7,722,671 B1 | 5/2010 | Carlyle et al. |
| 7,731,742 B2 | 6/2010 | Schlick et al. |
| 7,735,493 B2 | 6/2010 | Van Der Burg et al. |
| 7,736,327 B2 | 6/2010 | Wilk et al. |
| 7,736,388 B2 | 6/2010 | Goldfarb et al. |
| 7,743,481 B2 | 6/2010 | Lafont et al. |
| 7,748,389 B2 | 7/2010 | Salahieh et al. |
| 7,758,625 B2 | 7/2010 | Wu et al. |
| 7,763,065 B2 | 7/2010 | Schmid et al. |
| 7,771,463 B2 | 8/2010 | Ton et al. |
| 7,771,467 B2 | 8/2010 | Svensson |
| 7,776,083 B2 | 8/2010 | Vesely |
| 7,780,725 B2 | 8/2010 | Haug et al. |
| 7,780,726 B2 | 8/2010 | Seguin |
| 7,785,360 B2 | 8/2010 | Freitag |
| 7,794,487 B2 | 9/2010 | Majercak et al. |
| 7,799,046 B2 | 9/2010 | White et al. |
| 7,799,065 B2 | 9/2010 | Pappas |
| 7,803,185 B2 | 9/2010 | Gabbay |
| 7,806,919 B2 | 10/2010 | Bloom et al. |
| 7,823,267 B2 | 11/2010 | Bolduc |
| 7,824,442 B2 | 11/2010 | Salahieh et al. |
| 7,824,443 B2 | 11/2010 | Salahieh et al. |
| 7,833,262 B2 | 11/2010 | McGuckin, Jr. et al. |
| 7,837,727 B2 | 11/2010 | Goetz et al. |
| 7,846,203 B2 | 12/2010 | Cribier |
| 7,846,204 B2 | 12/2010 | Letac et al. |
| 7,854,758 B2 | 12/2010 | Taheri |
| 7,857,845 B2 | 12/2010 | Stacchino et al. |
| 7,862,602 B2 | 1/2011 | Licata et al. |
| 7,867,274 B2 | 1/2011 | Hill et al. |
| 7,887,583 B2 | 2/2011 | Macoviak |
| 7,892,276 B2 | 2/2011 | Stocker et al. |
| 7,892,292 B2 | 2/2011 | Stack et al. |
| 7,896,913 B2 | 3/2011 | Damm et al. |
| 7,896,915 B2 | 3/2011 | Guyenot et al. |
| 7,914,569 B2 | 3/2011 | Nguyen et al. |
| 7,914,574 B2 | 3/2011 | Schmid et al. |
| 7,914,575 B2 | 3/2011 | Guyenot et al. |
| 7,918,880 B2 | 4/2011 | Austin |
| 7,927,363 B2 | 4/2011 | Perouse |
| 7,938,851 B2 | 5/2011 | Olson et al. |
| 7,947,071 B2 | 5/2011 | Schmid et al. |
| 7,947,075 B2 | 5/2011 | Goetz et al. |
| 7,951,189 B2 | 5/2011 | Haverkost et al. |
| 7,959,666 B2 | 6/2011 | Salahieh et al. |
| 7,959,672 B2 | 6/2011 | Salahieh et al. |
| 7,967,853 B2 | 6/2011 | Eidenschink et al. |
| 7,972,359 B2 | 7/2011 | Kreidler |
| 7,972,376 B1 | 7/2011 | Dove et al. |
| 7,972,378 B2 | 7/2011 | Tabor et al. |
| 7,988,724 B2 | 8/2011 | Salahieh et al. |
| 7,993,386 B2 | 8/2011 | Elliott |
| 8,002,824 B2 | 8/2011 | Jenson et al. |

(56) References Cited

U.S. PATENT DOCUMENTS

| | | |
|---|---|---|
| 8,002,825 B2 | 8/2011 | Letac et al. |
| 8,012,198 B2 | 9/2011 | Hill et al. |
| 8,021,421 B2 | 9/2011 | Fogarty et al. |
| RE42,818 E | 10/2011 | Cali et al. |
| RE42,857 E | 10/2011 | Cali et al. |
| 8,038,704 B2 | 10/2011 | Sherburne |
| 8,038,709 B2 | 10/2011 | Palasis et al. |
| 8,043,450 B2 | 10/2011 | Cali et al. |
| 8,048,153 B2 | 11/2011 | Salahieh et al. |
| 8,052,715 B2 | 11/2011 | Quinn et al. |
| 8,052,749 B2 | 11/2011 | Salahieh et al. |
| 8,052,750 B2 | 11/2011 | Tuval et al. |
| 8,057,540 B2 | 11/2011 | Letac et al. |
| 8,062,355 B2 | 11/2011 | Figulla et al. |
| 8,062,536 B2 | 11/2011 | Liu et al. |
| 8,062,537 B2 | 11/2011 | Tuominen et al. |
| 8,062,749 B2 | 11/2011 | Shelestak et al. |
| 8,070,799 B2 | 12/2011 | Righini et al. |
| 8,075,641 B2 | 12/2011 | Aravanis et al. |
| 8,083,788 B2 | 12/2011 | Acosta et al. |
| 8,092,518 B2 | 1/2012 | Schreck |
| 8,092,520 B2 | 1/2012 | Quadri |
| 8,092,521 B2 | 1/2012 | Figulla et al. |
| 8,128,676 B2 | 3/2012 | Cummings |
| 8,128,681 B2 | 3/2012 | Shoemaker et al. |
| 8,133,217 B2 | 3/2012 | Stokes et al. |
| 8,133,270 B2 | 3/2012 | Kheradvar et al. |
| 8,136,659 B2 | 3/2012 | Salahieh et al. |
| 8,137,394 B2 | 3/2012 | Stocker et al. |
| 8,137,398 B2 | 3/2012 | Tuval et al. |
| 8,147,534 B2 | 4/2012 | Berez et al. |
| 8,157,853 B2 | 4/2012 | Laske et al. |
| 8,167,894 B2 | 5/2012 | Miles et al. |
| 8,172,896 B2 | 5/2012 | McNamara et al. |
| 8,182,528 B2 | 5/2012 | Salahieh et al. |
| 8,192,351 B2 | 6/2012 | Fishler et al. |
| 8,206,437 B2 | 6/2012 | Bonhoeffer et al. |
| 8,211,107 B2 | 7/2012 | Parks et al. |
| 8,216,174 B2 | 7/2012 | Wilk et al. |
| 8,216,301 B2 | 7/2012 | Bonhoeffer et al. |
| 8,221,493 B2 | 7/2012 | Boyle et al. |
| 8,226,707 B2 | 7/2012 | White |
| 8,226,710 B2 | 7/2012 | Nguyen et al. |
| 8,231,670 B2 | 7/2012 | Salahieh et al. |
| 8,236,049 B2 | 8/2012 | Rowe et al. |
| 8,236,241 B2 | 8/2012 | Carpentier et al. |
| 8,246,675 B2 | 8/2012 | Zegdi |
| 8,246,678 B2 | 8/2012 | Salahieh et al. |
| 8,252,051 B2 | 8/2012 | Chau et al. |
| 8,252,052 B2 | 8/2012 | Salahieh et al. |
| 8,277,500 B2 | 10/2012 | Schmid et al. |
| 8,287,584 B2 | 10/2012 | Salahieh et al. |
| 8,303,653 B2 | 11/2012 | Bonhoeffer et al. |
| 8,308,798 B2 | 11/2012 | Pintor et al. |
| 8,317,858 B2 | 11/2012 | Straubinger et al. |
| 8,323,335 B2 | 12/2012 | Rowe et al. |
| 8,328,868 B2 | 12/2012 | Paul et al. |
| 8,343,136 B2 | 1/2013 | Howat et al. |
| 8,343,213 B2 | 1/2013 | Salahieh et al. |
| 8,348,995 B2 | 1/2013 | Tuval et al. |
| 8,348,996 B2 | 1/2013 | Tuval et al. |
| 8,348,999 B2 | 1/2013 | Kheradvar et al. |
| 8,357,387 B2 | 1/2013 | Dove et al. |
| 8,366,767 B2 | 2/2013 | Zhang |
| 8,372,134 B2 | 2/2013 | Schlick et al. |
| 8,376,865 B2 | 2/2013 | Forster et al. |
| 8,377,117 B2 | 2/2013 | Keidar et al. |
| 8,382,822 B2 | 2/2013 | Pavcnik et al. |
| 8,398,704 B2 | 3/2013 | Straubinger et al. |
| 8,398,708 B2 | 3/2013 | Meiri et al. |
| 8,403,983 B2 | 3/2013 | Quadri et al. |
| 8,414,641 B2 | 4/2013 | Stocker et al. |
| 8,414,643 B2 | 4/2013 | Tuval et al. |
| 8,414,644 B2 | 4/2013 | Quadri et al. |
| 8,414,645 B2 | 4/2013 | Dwork et al. |
| 8,439,961 B2 | 5/2013 | Jagger et al. |
| 8,445,278 B2 | 5/2013 | Everaerts et al. |
| 8,460,365 B2 | 6/2013 | Haverkost et al. |
| 8,465,540 B2 | 6/2013 | Straubinger et al. |
| 8,468,667 B2 | 6/2013 | Straubinger et al. |
| 8,470,023 B2 | 6/2013 | Eidenschink et al. |
| 8,491,650 B2 | 7/2013 | Wiemeyer et al. |
| 8,512,394 B2 | 8/2013 | Schmid et al. |
| 8,512,399 B2 | 8/2013 | Lafontaine |
| 8,512,400 B2 | 8/2013 | Tran et al. |
| 8,512,401 B2 | 8/2013 | Murray, III et al. |
| 8,523,936 B2 | 9/2013 | Schmid et al. |
| 8,535,368 B2 | 9/2013 | Headley, Jr. et al. |
| 8,540,762 B2 | 9/2013 | Schmid et al. |
| 8,545,547 B2 | 10/2013 | Schmid et al. |
| 8,545,552 B2 | 10/2013 | Garrison et al. |
| 8,551,160 B2 | 10/2013 | Figulla et al. |
| 8,556,880 B2 | 10/2013 | Freyman et al. |
| 8,556,966 B2 | 10/2013 | Jenson |
| 8,568,475 B2 | 10/2013 | Nguyen et al. |
| 8,579,936 B2 | 11/2013 | Abbott et al. |
| 8,579,962 B2 | 11/2013 | Salahieh et al. |
| 8,579,965 B2 | 11/2013 | Bonhoeffer et al. |
| 8,585,756 B2 | 11/2013 | Bonhoeffer et al. |
| 8,585,759 B2 | 11/2013 | Bumbalough |
| 8,591,570 B2 | 11/2013 | Revuelta |
| 8,597,226 B2 | 12/2013 | Wilk et al. |
| 8,603,159 B2 | 12/2013 | Seguin et al. |
| 8,603,160 B2 | 12/2013 | Salahieh et al. |
| 8,617,235 B2 | 12/2013 | Schmid et al. |
| 8,617,236 B2 | 12/2013 | Paul et al. |
| 8,623,074 B2 | 1/2014 | Ryan |
| 8,623,075 B2 | 1/2014 | Murray, III et al. |
| 8,623,076 B2 | 1/2014 | Salahieh et al. |
| 8,623,078 B2 | 1/2014 | Salahieh et al. |
| 8,628,562 B2 | 1/2014 | Cummings |
| 8,628,571 B1 | 1/2014 | Hacohen et al. |
| 8,647,381 B2 | 2/2014 | Essinger et al. |
| 8,668,733 B2 | 3/2014 | Haug et al. |
| 8,672,997 B2 | 3/2014 | Drasler et al. |
| 8,679,174 B2 | 3/2014 | Ottma et al. |
| 8,685,077 B2 | 4/2014 | Laske et al. |
| 8,696,743 B2 | 4/2014 | Holecek et al. |
| 8,721,713 B2 | 5/2014 | Tower et al. |
| 8,721,717 B2 | 5/2014 | Shoemaker et al. |
| 8,734,508 B2 | 5/2014 | Hastings et al. |
| 8,758,430 B2 | 6/2014 | Ferrari et al. |
| 8,764,818 B2 | 7/2014 | Gregg |
| 8,778,020 B2 | 7/2014 | Gregg et al. |
| 8,790,395 B2 | 7/2014 | Straubinger et al. |
| 8,795,305 B2 | 8/2014 | Martin et al. |
| 8,795,356 B2 | 8/2014 | Quadri et al. |
| 8,808,356 B2 | 8/2014 | Braido et al. |
| 8,808,364 B2 | 8/2014 | Palasis et al. |
| RE45,130 E | 9/2014 | Figulla et al. |
| 8,828,078 B2 | 9/2014 | Salahieh et al. |
| 8,828,079 B2 | 9/2014 | Thielen et al. |
| 8,840,662 B2 | 9/2014 | Salahieh et al. |
| 8,840,663 B2 | 9/2014 | Salahieh et al. |
| 8,845,721 B2 | 9/2014 | Braido et al. |
| 8,851,286 B2 | 10/2014 | Chang et al. |
| 8,852,272 B2 | 10/2014 | Gross et al. |
| 8,858,620 B2 | 10/2014 | Salahieh et al. |
| 8,894,703 B2 | 11/2014 | Salahieh et al. |
| 8,932,349 B2 | 1/2015 | Jenson et al. |
| 8,940,014 B2 | 1/2015 | Gamarra et al. |
| 8,951,243 B2 | 2/2015 | Crisostomo et al. |
| 8,951,299 B2 | 2/2015 | Paul et al. |
| 8,956,383 B2 | 2/2015 | Aklog et al. |
| 8,992,608 B2 | 3/2015 | Haug et al. |
| 8,998,976 B2 | 4/2015 | Gregg et al. |
| 9,005,273 B2 | 4/2015 | Salahieh et al. |
| 9,011,521 B2 | 4/2015 | Haug et al. |
| 9,023,099 B2 | 5/2015 | Duffy et al. |
| 9,028,542 B2 | 5/2015 | Hill et al. |
| 9,039,756 B2 | 5/2015 | White |
| 9,044,318 B2 | 6/2015 | Straubinger et al. |
| 9,131,926 B2 | 9/2015 | Crisostomo et al. |
| 9,138,315 B2 | 9/2015 | Straubinger et al. |

(56) References Cited

U.S. PATENT DOCUMENTS

| | | |
|---|---|---|
| 9,149,358 B2 | 10/2015 | Tabor et al. |
| 9,168,130 B2 | 10/2015 | Straubinger et al. |
| 9,168,131 B2 | 10/2015 | Yohanan et al. |
| 9,168,136 B2 | 10/2015 | Yang et al. |
| RE45,790 E | 11/2015 | Figulla et al. |
| 9,180,005 B1 | 11/2015 | Lashinski et al. |
| 9,186,482 B2 | 11/2015 | Dorn |
| 9,211,266 B2 | 12/2015 | Iwazawa et al. |
| 9,216,082 B2 | 12/2015 | Von Segesser et al. |
| 9,248,037 B2 | 2/2016 | Roeder et al. |
| 9,265,608 B2 | 2/2016 | Miller et al. |
| 9,277,991 B2 | 3/2016 | Salahieh et al. |
| 9,277,993 B2 | 3/2016 | Gamarra et al. |
| 9,295,551 B2 | 3/2016 | Straubinger et al. |
| 9,301,840 B2 | 4/2016 | Nguyen et al. |
| 9,301,843 B2 | 4/2016 | Richardson et al. |
| 9,308,085 B2 | 4/2016 | Salahieh et al. |
| 9,320,599 B2 | 4/2016 | Salahieh et al. |
| 9,326,853 B2 | 5/2016 | Olson et al. |
| 9,358,106 B2 | 6/2016 | Salahieh et al. |
| 9,358,110 B2 | 6/2016 | Paul et al. |
| 9,370,419 B2 | 6/2016 | Hill et al. |
| 9,370,421 B2 | 6/2016 | Crisostomo et al. |
| 9,387,076 B2 | 7/2016 | Paul et al. |
| 9,393,094 B2 | 7/2016 | Salahieh et al. |
| 9,393,113 B2 | 7/2016 | Salahieh et al. |
| 9,393,114 B2 | 7/2016 | Sutton et al. |
| 9,393,115 B2 | 7/2016 | Tabor et al. |
| 9,415,567 B2 | 8/2016 | Sogard et al. |
| 9,421,083 B2 | 8/2016 | Eidenschink et al. |
| 9,439,759 B2 | 9/2016 | Straubinger et al. |
| 9,463,084 B2 | 10/2016 | Stinson |
| 9,474,598 B2 | 10/2016 | Gregg et al. |
| 9,474,609 B2 | 10/2016 | Haverkost et al. |
| 9,492,276 B2 | 11/2016 | Lee et al. |
| 9,510,945 B2 | 12/2016 | Sutton et al. |
| 9,510,947 B2 | 12/2016 | Straubinger et al. |
| 9,526,609 B2 | 12/2016 | Salahieh et al. |
| 9,532,872 B2 | 1/2017 | Salahieh et al. |
| 9,539,091 B2 | 1/2017 | Yang et al. |
| 9,554,924 B2 | 1/2017 | Schlick et al. |
| 9,597,432 B2 | 3/2017 | Nakamura |
| 9,649,212 B2 | 5/2017 | Fargahi |
| 9,717,593 B2 | 8/2017 | Alkhatib et al. |
| 9,744,031 B2 | 8/2017 | Girard et al. |
| D800,908 S | 10/2017 | Hariton et al. |
| 9,775,709 B2 | 10/2017 | Miller et al. |
| 9,788,945 B2 | 10/2017 | Ottma et al. |
| 9,861,476 B2 | 1/2018 | Salahieh et al. |
| 9,867,694 B2 | 1/2018 | Girard et al. |
| 9,867,699 B2 | 1/2018 | Straubinger et al. |
| 9,872,768 B2 | 1/2018 | Paul et al. |
| 9,878,127 B2 | 1/2018 | Damm et al. |
| 9,889,002 B2 | 2/2018 | Bonhoeffer et al. |
| 9,901,445 B2 | 2/2018 | Backus et al. |
| 9,949,824 B2 | 4/2018 | Bonhoeffer et al. |
| 9,956,075 B2 | 5/2018 | Salahieh et al. |
| 9,968,761 B2 | 5/2018 | Brecker |
| 9,987,133 B2 | 6/2018 | Straubinger et al. |
| 10,092,324 B2 | 10/2018 | Gillespie et al. |
| 10,143,552 B2 | 12/2018 | Wallace et al. |
| 10,154,901 B2 | 12/2018 | Straubinger et al. |
| 10,321,987 B2 | 6/2019 | Wang et al. |
| 10,363,134 B2 | 7/2019 | Figulla et al. |
| 10,543,084 B2 | 1/2020 | Guyenot et al. |
| 10,575,947 B2 | 3/2020 | Straubinger et al. |
| 10,638,918 B2 | 5/2020 | Atarot et al. |
| 10,702,382 B2 | 7/2020 | Straubinger et al. |
| 10,709,555 B2 | 7/2020 | Schreck et al. |
| 10,856,978 B2 | 12/2020 | Straubinger et al. |
| 10,856,987 B2 | 12/2020 | Cabiri et al. |
| 11,065,138 B2 | 7/2021 | Schreck et al. |
| 11,147,669 B2 | 10/2021 | Straubinger et al. |
| 11,154,398 B2 | 10/2021 | Straubinger et al. |
| 11,185,405 B2 | 11/2021 | Girard et al. |
| 11,197,754 B2 | 12/2021 | Saffari et al. |
| 11,266,497 B2 | 3/2022 | Cao et al. |
| 11,911,264 B2 | 2/2024 | Chau et al. |
| 11,951,005 B2 | 4/2024 | Gross et al. |
| 2001/0000041 A1 | 3/2001 | Selmon et al. |
| 2001/0001314 A1 | 5/2001 | Davison et al. |
| 2001/0002445 A1 | 5/2001 | Vesely |
| 2001/0004683 A1 | 6/2001 | Gambale et al. |
| 2001/0004690 A1 | 6/2001 | Gambale et al. |
| 2001/0004699 A1 | 6/2001 | Gittings et al. |
| 2001/0007956 A1 | 7/2001 | Letac et al. |
| 2001/0008969 A1 | 7/2001 | Evans et al. |
| 2001/0010017 A1 | 7/2001 | Letac et al. |
| 2001/0011187 A1 | 8/2001 | Pavcnik et al. |
| 2001/0011189 A1 | 8/2001 | Drasler et al. |
| 2001/0012948 A1 | 8/2001 | Vanney |
| 2001/0014813 A1 | 8/2001 | Saadat et al. |
| 2001/0016700 A1 | 8/2001 | Eno et al. |
| 2001/0018596 A1 | 8/2001 | Selmon et al. |
| 2001/0020172 A1 | 9/2001 | Selmon et al. |
| 2001/0021872 A1 | 9/2001 | Bailey et al. |
| 2001/0025196 A1 | 9/2001 | Chinn et al. |
| 2001/0025643 A1 | 10/2001 | Foley |
| 2001/0027287 A1 | 10/2001 | Shmulewitz et al. |
| 2001/0027338 A1 | 10/2001 | Greenberg |
| 2001/0027339 A1 | 10/2001 | Boatman et al. |
| 2001/0029385 A1 | 10/2001 | Shennib et al. |
| 2001/0032013 A1 | 10/2001 | Marton |
| 2001/0034547 A1 | 10/2001 | Hall et al. |
| 2001/0037117 A1 | 11/2001 | Gambale et al. |
| 2001/0037141 A1 | 11/2001 | Yee et al. |
| 2001/0037149 A1 | 11/2001 | Wilk |
| 2001/0039426 A1 | 11/2001 | Makower et al. |
| 2001/0039445 A1 | 11/2001 | Hall et al. |
| 2001/0039450 A1 | 11/2001 | Pavcnik et al. |
| 2001/0041902 A1 | 11/2001 | Lepulu et al. |
| 2001/0041928 A1 | 11/2001 | Pavcnik et al. |
| 2001/0041930 A1 | 11/2001 | Globerman et al. |
| 2001/0044631 A1 | 11/2001 | Akin et al. |
| 2001/0044634 A1 | 11/2001 | Don Michael et al. |
| 2001/0044647 A1 | 11/2001 | Pinchuk et al. |
| 2001/0044652 A1 | 11/2001 | Moore |
| 2001/0044656 A1 | 11/2001 | Williamson, IV et al. |
| 2001/0047165 A1 | 11/2001 | Makower et al. |
| 2001/0049523 A1 | 12/2001 | DeVore et al. |
| 2001/0051822 A1 | 12/2001 | Stack et al. |
| 2001/0053930 A1 | 12/2001 | Kugler et al. |
| 2001/0053932 A1 | 12/2001 | Phelps et al. |
| 2002/0002349 A1 | 1/2002 | Flaherty et al. |
| 2002/0002396 A1 | 1/2002 | Fulkerson |
| 2002/0002401 A1 | 1/2002 | McGuckin, Jr. et al. |
| 2002/0004662 A1 | 1/2002 | Wilk |
| 2002/0004663 A1 | 1/2002 | Gittings et al. |
| 2002/0007138 A1 | 1/2002 | Wilk et al. |
| 2002/0010489 A1 | 1/2002 | Grayzel et al. |
| 2002/0010508 A1 | 1/2002 | Chobotov |
| 2002/0026233 A1 | 2/2002 | Shaknovich |
| 2002/0029014 A1 | 3/2002 | Jayaraman |
| 2002/0029079 A1 | 3/2002 | Kim et al. |
| 2002/0029981 A1 | 3/2002 | Nigam |
| 2002/0032476 A1 | 3/2002 | Gambale et al. |
| 2002/0032478 A1 | 3/2002 | Boekstegers et al. |
| 2002/0032480 A1 | 3/2002 | Spence et al. |
| 2002/0032481 A1 | 3/2002 | Gabbay |
| 2002/0035390 A1 | 3/2002 | Schaldach et al. |
| 2002/0035396 A1 | 3/2002 | Heath |
| 2002/0042650 A1 | 4/2002 | Vardi et al. |
| 2002/0042651 A1 | 4/2002 | Liddicoat et al. |
| 2002/0045846 A1 | 4/2002 | Kaplon et al. |
| 2002/0045928 A1 | 4/2002 | Boekstegers |
| 2002/0045929 A1 | 4/2002 | Diaz |
| 2002/0049486 A1 | 4/2002 | Knudson et al. |
| 2002/0052651 A1 | 5/2002 | Myers et al. |
| 2002/0055767 A1 | 5/2002 | Forde et al. |
| 2002/0055769 A1 | 5/2002 | Wang |
| 2002/0055772 A1 | 5/2002 | McGuckin, Jr. et al. |
| 2002/0055774 A1 | 5/2002 | Liddicoat |
| 2002/0055775 A1 | 5/2002 | Carpentier et al. |
| 2002/0058897 A1 | 5/2002 | Renati |

(56) References Cited

U.S. PATENT DOCUMENTS

| | | |
|---|---|---|
| 2002/0058987 A1 | 5/2002 | Butaric et al. |
| 2002/0058993 A1 | 5/2002 | Landau et al. |
| 2002/0058995 A1 | 5/2002 | Stevens |
| 2002/0062146 A1 | 5/2002 | Makower et al. |
| 2002/0065478 A1 | 5/2002 | Knudson et al. |
| 2002/0065485 A1 | 5/2002 | DuBois et al. |
| 2002/0072699 A1 | 6/2002 | Knudson et al. |
| 2002/0072789 A1 | 6/2002 | Hackett et al. |
| 2002/0077566 A1 | 6/2002 | Laroya et al. |
| 2002/0077654 A1 | 6/2002 | Javier, Jr. et al. |
| 2002/0077696 A1 | 6/2002 | Zadno-Azizi et al. |
| 2002/0082584 A1 | 6/2002 | Rosenman et al. |
| 2002/0082609 A1 | 6/2002 | Green |
| 2002/0092535 A1 | 7/2002 | Wilk |
| 2002/0092536 A1 | 7/2002 | LaFontaine et al. |
| 2002/0095111 A1 | 7/2002 | Tweden et al. |
| 2002/0095173 A1 | 7/2002 | Mazzocchi et al. |
| 2002/0095206 A1 | 7/2002 | Addonizio et al. |
| 2002/0095209 A1 | 7/2002 | Zadno-Azizi et al. |
| 2002/0099439 A1 | 7/2002 | Schwartz et al. |
| 2002/0100484 A1 | 8/2002 | Hall et al. |
| 2002/0103533 A1 | 8/2002 | Langberg et al. |
| 2002/0107565 A1 | 8/2002 | Greenhalgh |
| 2002/0111627 A1 | 8/2002 | Vincent-Prestigiacomo |
| 2002/0111665 A1 | 8/2002 | Lauterjung |
| 2002/0111668 A1 | 8/2002 | Smith |
| 2002/0111672 A1 | 8/2002 | Kim et al. |
| 2002/0111674 A1 | 8/2002 | Chouinard et al. |
| 2002/0117789 A1 | 8/2002 | Childers et al. |
| 2002/0120322 A1 | 8/2002 | Thompson et al. |
| 2002/0120323 A1 | 8/2002 | Thompson et al. |
| 2002/0120328 A1 | 8/2002 | Pathak et al. |
| 2002/0123698 A1 | 9/2002 | Garibotto et al. |
| 2002/0123786 A1 | 9/2002 | Gittings et al. |
| 2002/0123790 A1 | 9/2002 | White et al. |
| 2002/0123802 A1 | 9/2002 | Snyders |
| 2002/0128552 A1 | 9/2002 | Nowlin et al. |
| 2002/0133183 A1 | 9/2002 | Lentz et al. |
| 2002/0133226 A1 | 9/2002 | Marquez et al. |
| 2002/0138087 A1 | 9/2002 | Shennib et al. |
| 2002/0138138 A1 | 9/2002 | Yang |
| 2002/0143285 A1 | 10/2002 | Eno et al. |
| 2002/0143289 A1 | 10/2002 | Ellis et al. |
| 2002/0143387 A1 | 10/2002 | Soetikno et al. |
| 2002/0144696 A1 | 10/2002 | Sharkawy et al. |
| 2002/0151913 A1 | 10/2002 | Berg et al. |
| 2002/0151970 A1 | 10/2002 | Garrison et al. |
| 2002/0156522 A1 | 10/2002 | Ivancev et al. |
| 2002/0161377 A1 | 10/2002 | Rabkin |
| 2002/0161383 A1 | 10/2002 | Akin et al. |
| 2002/0161390 A1 | 10/2002 | Mouw |
| 2002/0161392 A1 | 10/2002 | Dubrul |
| 2002/0161394 A1 | 10/2002 | Macoviak et al. |
| 2002/0161424 A1 | 10/2002 | Rapacki et al. |
| 2002/0161426 A1 | 10/2002 | Iancea |
| 2002/0165479 A1 | 11/2002 | Wilk |
| 2002/0165576 A1 | 11/2002 | Boyle et al. |
| 2002/0165606 A1 | 11/2002 | Wolf et al. |
| 2002/0173842 A1 | 11/2002 | Buchanan |
| 2002/0177766 A1 | 11/2002 | Mogul |
| 2002/0177772 A1 | 11/2002 | Altman et al. |
| 2002/0177840 A1 | 11/2002 | Farnholtz |
| 2002/0177894 A1 | 11/2002 | Acosta et al. |
| 2002/0179098 A1 | 12/2002 | Makower et al. |
| 2002/0183716 A1 | 12/2002 | Herweck et al. |
| 2002/0183781 A1 | 12/2002 | Casey et al. |
| 2002/0186558 A1 | 12/2002 | Plank et al. |
| 2002/0188341 A1 | 12/2002 | Elliott |
| 2002/0188344 A1 | 12/2002 | Bolea et al. |
| 2002/0193782 A1 | 12/2002 | Ellis et al. |
| 2002/0193871 A1 | 12/2002 | Beyersdorf et al. |
| 2002/0198594 A1 | 12/2002 | Schreck |
| 2003/0004541 A1 | 1/2003 | Linder et al. |
| 2003/0004560 A1 | 1/2003 | Chobotov et al. |
| 2003/0009189 A1 | 1/2003 | Gilson et al. |
| 2003/0014104 A1 | 1/2003 | Cribier |
| 2003/0018377 A1 | 1/2003 | Berg et al. |
| 2003/0018379 A1 | 1/2003 | Knudson et al. |
| 2003/0023300 A1 | 1/2003 | Bailey et al. |
| 2003/0023303 A1 | 1/2003 | Palmaz et al. |
| 2003/0027332 A1 | 2/2003 | Lafrance et al. |
| 2003/0028213 A1 | 2/2003 | Thill et al. |
| 2003/0028247 A1 | 2/2003 | Cali |
| 2003/0033001 A1 | 2/2003 | Igaki |
| 2003/0036791 A1 | 2/2003 | Philipp et al. |
| 2003/0036795 A1 | 2/2003 | Andersen et al. |
| 2003/0040736 A1 | 2/2003 | Stevens et al. |
| 2003/0040771 A1 | 2/2003 | Hyodoh et al. |
| 2003/0040772 A1 | 2/2003 | Hyodoh et al. |
| 2003/0040791 A1 | 2/2003 | Oktay |
| 2003/0040792 A1 | 2/2003 | Gabbay |
| 2003/0042186 A1 | 3/2003 | Boyle |
| 2003/0044315 A1 | 3/2003 | Boekstegers |
| 2003/0045828 A1 | 3/2003 | Wilk |
| 2003/0050694 A1 | 3/2003 | Yang et al. |
| 2003/0055371 A1 | 3/2003 | Wolf et al. |
| 2003/0055495 A1 | 3/2003 | Pease et al. |
| 2003/0057156 A1 | 3/2003 | Peterson et al. |
| 2003/0060844 A1 | 3/2003 | Borillo et al. |
| 2003/0065386 A1 | 4/2003 | Weadock |
| 2003/0069492 A1 | 4/2003 | Abrams et al. |
| 2003/0069646 A1 | 4/2003 | Stinson |
| 2003/0070944 A1 | 4/2003 | Nigam |
| 2003/0073973 A1 | 4/2003 | Evans et al. |
| 2003/0074058 A1 | 4/2003 | Sherry |
| 2003/0078561 A1 | 4/2003 | Gambale et al. |
| 2003/0078652 A1 | 4/2003 | Sutherland |
| 2003/0083730 A1 | 5/2003 | Stinson |
| 2003/0093145 A1 | 5/2003 | Lawrence-Brown et al. |
| 2003/0100918 A1 | 5/2003 | Duane |
| 2003/0100919 A1 | 5/2003 | Hopkins et al. |
| 2003/0100920 A1 | 5/2003 | Akin et al. |
| 2003/0105514 A1 | 6/2003 | Phelps et al. |
| 2003/0109924 A1 | 6/2003 | Cribier |
| 2003/0109930 A1 | 6/2003 | Bluni et al. |
| 2003/0114912 A1 | 6/2003 | Sequin et al. |
| 2003/0114913 A1 | 6/2003 | Spenser et al. |
| 2003/0120195 A1 | 6/2003 | Milo et al. |
| 2003/0125795 A1 | 7/2003 | Pavcnik et al. |
| 2003/0130726 A1 | 7/2003 | Thorpe et al. |
| 2003/0130727 A1 | 7/2003 | Drasler et al. |
| 2003/0130729 A1 | 7/2003 | Paniagua et al. |
| 2003/0130746 A1 | 7/2003 | Ashworth et al. |
| 2003/0135257 A1 | 7/2003 | Taheri |
| 2003/0139796 A1 | 7/2003 | Sequin et al. |
| 2003/0139798 A1 | 7/2003 | Brown et al. |
| 2003/0139803 A1 | 7/2003 | Sequin et al. |
| 2003/0139804 A1 | 7/2003 | Hankh et al. |
| 2003/0144657 A1 | 7/2003 | Bowe et al. |
| 2003/0144732 A1 | 7/2003 | Cosgrove et al. |
| 2003/0149474 A1 | 8/2003 | Becker |
| 2003/0149475 A1 | 8/2003 | Hyodoh et al. |
| 2003/0149476 A1 | 8/2003 | Damm et al. |
| 2003/0149477 A1 | 8/2003 | Gabbay |
| 2003/0149478 A1 | 8/2003 | Figulla et al. |
| 2003/0153971 A1 | 8/2003 | Chandrasekaran |
| 2003/0153974 A1 | 8/2003 | Spenser et al. |
| 2003/0158573 A1 | 8/2003 | Gittings et al. |
| 2003/0158595 A1 | 8/2003 | Randall et al. |
| 2003/0163193 A1 | 8/2003 | Widenhouse |
| 2003/0163198 A1 | 8/2003 | Morra et al. |
| 2003/0165352 A1 | 9/2003 | Ibrahim et al. |
| 2003/0171803 A1 | 9/2003 | Shimon |
| 2003/0171805 A1 | 9/2003 | Berg et al. |
| 2003/0176884 A1 | 9/2003 | Berrada et al. |
| 2003/0181850 A1 | 9/2003 | Diamond et al. |
| 2003/0181938 A1 | 9/2003 | Roth et al. |
| 2003/0181942 A1 | 9/2003 | Sutton et al. |
| 2003/0187495 A1 | 10/2003 | Cully et al. |
| 2003/0191449 A1 | 10/2003 | Nash et al. |
| 2003/0191516 A1 | 10/2003 | Weldon et al. |
| 2003/0191519 A1 | 10/2003 | Lombardi et al. |
| 2003/0191526 A1 | 10/2003 | Van Tassel et al. |
| 2003/0195457 A1 | 10/2003 | LaFontaine et al. |

(56) References Cited

U.S. PATENT DOCUMENTS

| | | |
|---|---|---|
| 2003/0195458 A1 | 10/2003 | Phelps et al. |
| 2003/0195609 A1 | 10/2003 | Berenstein et al. |
| 2003/0195620 A1 | 10/2003 | Huynh et al. |
| 2003/0198722 A1 | 10/2003 | Johnston, Jr. et al. |
| 2003/0199759 A1 | 10/2003 | Richard |
| 2003/0199913 A1 | 10/2003 | Dubrul et al. |
| 2003/0199963 A1 | 10/2003 | Tower et al. |
| 2003/0199971 A1 | 10/2003 | Tower et al. |
| 2003/0199972 A1 | 10/2003 | Zadno-Azizi et al. |
| 2003/0204160 A1 | 10/2003 | Kamm et al. |
| 2003/0204249 A1 | 10/2003 | Letort |
| 2003/0208224 A1 | 11/2003 | Broome |
| 2003/0212410 A1 | 11/2003 | Stenzel et al. |
| 2003/0212413 A1 | 11/2003 | Wilk |
| 2003/0212429 A1 | 11/2003 | Keegan et al. |
| 2003/0212452 A1 | 11/2003 | Zadno-Azizi et al. |
| 2003/0212454 A1 | 11/2003 | Scott et al. |
| 2003/0216678 A1 | 11/2003 | March et al. |
| 2003/0216679 A1 | 11/2003 | Wolf et al. |
| 2003/0216774 A1 | 11/2003 | Larson |
| 2003/0220661 A1 | 11/2003 | Mowry et al. |
| 2003/0220667 A1 | 11/2003 | Van Der Burg et al. |
| 2003/0225445 A1 | 12/2003 | Derus et al. |
| 2003/0229366 A1 | 12/2003 | Reggie et al. |
| 2003/0229390 A1 | 12/2003 | Ashton et al. |
| 2003/0233117 A1 | 12/2003 | Adams et al. |
| 2003/0236542 A1 | 12/2003 | Makower |
| 2003/0236567 A1 | 12/2003 | Elliot |
| 2003/0236568 A1 | 12/2003 | Hojeibane et al. |
| 2003/0236570 A1 | 12/2003 | Cook et al. |
| 2004/0004926 A1 | 1/2004 | Maeda |
| 2004/0006298 A1 | 1/2004 | Wilk |
| 2004/0006380 A1 | 1/2004 | Buck et al. |
| 2004/0015225 A1 | 1/2004 | Kim et al. |
| 2004/0015228 A1 | 1/2004 | Lombardi et al. |
| 2004/0018651 A1 | 1/2004 | Nadeau |
| 2004/0019348 A1 | 1/2004 | Stevens et al. |
| 2004/0019374 A1 | 1/2004 | Hojeibane et al. |
| 2004/0026389 A1 | 2/2004 | Kessler et al. |
| 2004/0033364 A1 | 2/2004 | Spiridigliozzi et al. |
| 2004/0034411 A1 | 2/2004 | Quijano et al. |
| 2004/0037946 A1 | 2/2004 | Morra et al. |
| 2004/0039343 A1 | 2/2004 | Eppstein et al. |
| 2004/0039436 A1 | 2/2004 | Spenser et al. |
| 2004/0044350 A1 | 3/2004 | Martin et al. |
| 2004/0044361 A1 | 3/2004 | Frazier et al. |
| 2004/0044392 A1 | 3/2004 | Von Oepen |
| 2004/0044400 A1 | 3/2004 | Cheng et al. |
| 2004/0044402 A1 | 3/2004 | Jung et al. |
| 2004/0049204 A1 | 3/2004 | Harari et al. |
| 2004/0049207 A1 | 3/2004 | Goldfarb et al. |
| 2004/0049224 A1 | 3/2004 | Buehlmann et al. |
| 2004/0049226 A1 | 3/2004 | Keegan et al. |
| 2004/0049262 A1 | 3/2004 | Obermiller et al. |
| 2004/0049266 A1 | 3/2004 | Anduiza et al. |
| 2004/0058097 A1 | 3/2004 | Weder |
| 2004/0059280 A1 | 3/2004 | Makower et al. |
| 2004/0059407 A1 | 3/2004 | Escamilla et al. |
| 2004/0059409 A1 | 3/2004 | Stenzel |
| 2004/0059429 A1 | 3/2004 | Amin et al. |
| 2004/0073157 A1 | 4/2004 | Knudson et al. |
| 2004/0073198 A1 | 4/2004 | Gilson et al. |
| 2004/0073238 A1 | 4/2004 | Makower |
| 2004/0073289 A1 | 4/2004 | Hartley |
| 2004/0077987 A1 | 4/2004 | Rapacki et al. |
| 2004/0077988 A1 | 4/2004 | Tweden et al. |
| 2004/0077990 A1 | 4/2004 | Knudson et al. |
| 2004/0078950 A1 | 4/2004 | Schreck |
| 2004/0082904 A1 | 4/2004 | Houde et al. |
| 2004/0082967 A1 | 4/2004 | Broome et al. |
| 2004/0082989 A1 | 4/2004 | Cook et al. |
| 2004/0087982 A1 | 5/2004 | Eskuri |
| 2004/0088042 A1 | 5/2004 | Kim et al. |
| 2004/0088045 A1 | 5/2004 | Cox |
| 2004/0092858 A1 | 5/2004 | Wilson et al. |
| 2004/0092989 A1 | 5/2004 | Wilson et al. |
| 2004/0093005 A1 | 5/2004 | Durcan |
| 2004/0093016 A1 | 5/2004 | Root et al. |
| 2004/0093060 A1 | 5/2004 | Seguin et al. |
| 2004/0093063 A1 | 5/2004 | Wright et al. |
| 2004/0093070 A1 | 5/2004 | Hojeibane et al. |
| 2004/0093075 A1 | 5/2004 | Kuehne |
| 2004/0097788 A1 | 5/2004 | Mourlas et al. |
| 2004/0098022 A1 | 5/2004 | Barone |
| 2004/0098098 A1 | 5/2004 | McGuckin, Jr. et al. |
| 2004/0098099 A1 | 5/2004 | McCullagh et al. |
| 2004/0098112 A1 | 5/2004 | DiMatteo et al. |
| 2004/0102855 A1 | 5/2004 | Shank |
| 2004/0106931 A1 | 6/2004 | Guiles et al. |
| 2004/0106976 A1 | 6/2004 | Bailey et al. |
| 2004/0106990 A1 | 6/2004 | Spence et al. |
| 2004/0107004 A1 | 6/2004 | Levine et al. |
| 2004/0111096 A1 | 6/2004 | Tu et al. |
| 2004/0113306 A1 | 6/2004 | Rapacki et al. |
| 2004/0116951 A1 | 6/2004 | Rosengart |
| 2004/0116999 A1 | 6/2004 | Ledergerber |
| 2004/0117004 A1 | 6/2004 | Osborne et al. |
| 2004/0117009 A1 | 6/2004 | Cali et al. |
| 2004/0118415 A1 | 6/2004 | Hall et al. |
| 2004/0122318 A1 | 6/2004 | Flaherty et al. |
| 2004/0122347 A1 | 6/2004 | Knudson et al. |
| 2004/0122468 A1 | 6/2004 | Yodfat et al. |
| 2004/0122514 A1 | 6/2004 | Fogarty et al. |
| 2004/0122516 A1 | 6/2004 | Fogarty et al. |
| 2004/0127847 A1 | 7/2004 | DuBois et al. |
| 2004/0127912 A1 | 7/2004 | Rabkin et al. |
| 2004/0127936 A1 | 7/2004 | Salahieh et al. |
| 2004/0127979 A1 | 7/2004 | Wilson et al. |
| 2004/0127982 A1 | 7/2004 | Machold et al. |
| 2004/0133154 A1 | 7/2004 | Flaherty et al. |
| 2004/0133225 A1 | 7/2004 | Makower |
| 2004/0133274 A1 | 7/2004 | Webler et al. |
| 2004/0138694 A1 | 7/2004 | Tran et al. |
| 2004/0138742 A1 | 7/2004 | Myers et al. |
| 2004/0138743 A1 | 7/2004 | Myers et al. |
| 2004/0138745 A1 | 7/2004 | Macoviak et al. |
| 2004/0147868 A1 | 7/2004 | Bardsley et al. |
| 2004/0147869 A1 | 7/2004 | Wolf et al. |
| 2004/0148018 A1 | 7/2004 | Carpentier et al. |
| 2004/0148021 A1 | 7/2004 | Cartledge et al. |
| 2004/0153094 A1 | 8/2004 | Dunfee et al. |
| 2004/0153145 A1 | 8/2004 | Simionescu et al. |
| 2004/0153146 A1 | 8/2004 | Lashinski et al. |
| 2004/0158143 A1 | 8/2004 | Flaherty et al. |
| 2004/0158277 A1 | 8/2004 | Lowe et al. |
| 2004/0163094 A1 | 8/2004 | Matsui et al. |
| 2004/0167444 A1 | 8/2004 | Laroya et al. |
| 2004/0167565 A1 | 8/2004 | Beulke et al. |
| 2004/0167573 A1 | 8/2004 | Williamson, IV et al. |
| 2004/0167620 A1 | 8/2004 | Ortiz et al. |
| 2004/0168691 A1 | 9/2004 | Sharkawy et al. |
| 2004/0176791 A1 | 9/2004 | Lim et al. |
| 2004/0181140 A1 | 9/2004 | Falwell et al. |
| 2004/0186507 A1 | 9/2004 | Hall et al. |
| 2004/0186557 A1 | 9/2004 | Gambale et al. |
| 2004/0186558 A1 | 9/2004 | Pavcnik et al. |
| 2004/0186563 A1 | 9/2004 | Lobbi |
| 2004/0186565 A1 | 9/2004 | Schreck |
| 2004/0186587 A1 | 9/2004 | Ahern |
| 2004/0193180 A1 | 9/2004 | Buzzard et al. |
| 2004/0193244 A1 | 9/2004 | Hartley et al. |
| 2004/0193252 A1 | 9/2004 | Perez et al. |
| 2004/0193261 A1 | 9/2004 | Berreklouw |
| 2004/0197695 A1 | 10/2004 | Aono |
| 2004/0199245 A1 | 10/2004 | Lauterjung |
| 2004/0204683 A1 | 10/2004 | McGuckin, Jr. et al. |
| 2004/0204755 A1 | 10/2004 | Robin |
| 2004/0206363 A1 | 10/2004 | McCarthy et al. |
| 2004/0210104 A1 | 10/2004 | Lau et al. |
| 2004/0210190 A1 | 10/2004 | Kohler et al. |
| 2004/0210240 A1 | 10/2004 | Saint |
| 2004/0210301 A1 | 10/2004 | Obermiller |
| 2004/0210304 A1 | 10/2004 | Seguin et al. |
| 2004/0210306 A1 | 10/2004 | Quijano et al. |

(56) References Cited

U.S. PATENT DOCUMENTS

| | | |
|---|---|---|
| 2004/0210307 A1 | 10/2004 | Khairkhahan |
| 2004/0215317 A1 | 10/2004 | Cummings |
| 2004/0215331 A1 | 10/2004 | Chew et al. |
| 2004/0215333 A1 | 10/2004 | Duran et al. |
| 2004/0215339 A1 | 10/2004 | Drasler et al. |
| 2004/0219180 A1 | 11/2004 | Gambale et al. |
| 2004/0220598 A1 | 11/2004 | Bolduc et al. |
| 2004/0220655 A1 | 11/2004 | Swanson et al. |
| 2004/0225321 A1 | 11/2004 | Krolik et al. |
| 2004/0225353 A1 | 11/2004 | McGuckin, Jr. et al. |
| 2004/0225354 A1 | 11/2004 | Allen et al. |
| 2004/0225355 A1 | 11/2004 | Stevens |
| 2004/0236411 A1 | 11/2004 | Sarac et al. |
| 2004/0236418 A1 | 11/2004 | Stevens |
| 2004/0243143 A1 | 12/2004 | Corcoran et al. |
| 2004/0243221 A1 | 12/2004 | Fawzi et al. |
| 2004/0249343 A1 | 12/2004 | Cioanta |
| 2004/0254594 A1 | 12/2004 | Alfaro |
| 2004/0254636 A1 | 12/2004 | Flagle et al. |
| 2004/0260389 A1 | 12/2004 | Case et al. |
| 2004/0260390 A1 | 12/2004 | Sarac et al. |
| 2004/0260393 A1 | 12/2004 | Rahdert et al. |
| 2004/0260394 A1 | 12/2004 | Douk et al. |
| 2004/0267357 A1 | 12/2004 | Allen et al. |
| 2005/0000858 A1 | 1/2005 | Roovers |
| 2005/0004505 A1 | 1/2005 | Phelps et al. |
| 2005/0004558 A1 | 1/2005 | Gambale et al. |
| 2005/0004648 A1 | 1/2005 | Boekstegers |
| 2005/0008589 A1 | 1/2005 | Legrand et al. |
| 2005/0009000 A1 | 1/2005 | Wilhelm et al. |
| 2005/0010246 A1 | 1/2005 | Streeter et al. |
| 2005/0010285 A1 | 1/2005 | Lambrecht et al. |
| 2005/0010287 A1 | 1/2005 | Macoviak et al. |
| 2005/0015112 A1 | 1/2005 | Cohn et al. |
| 2005/0021136 A1 | 1/2005 | Xie et al. |
| 2005/0025857 A1 | 2/2005 | Schoenherr et al. |
| 2005/0027305 A1 | 2/2005 | Shiu et al. |
| 2005/0027348 A1 | 2/2005 | Case et al. |
| 2005/0033220 A1 | 2/2005 | Wilk et al. |
| 2005/0033398 A1 | 2/2005 | Seguin |
| 2005/0033402 A1 | 2/2005 | Cully et al. |
| 2005/0038495 A1 | 2/2005 | Greenan |
| 2005/0038509 A1 | 2/2005 | Ashe |
| 2005/0043585 A1 | 2/2005 | Datta et al. |
| 2005/0043711 A1 | 2/2005 | Corcoran et al. |
| 2005/0043757 A1 | 2/2005 | Arad et al. |
| 2005/0043759 A1 | 2/2005 | Chanduszko |
| 2005/0043760 A1 | 2/2005 | Fogarty et al. |
| 2005/0043781 A1 | 2/2005 | Foley |
| 2005/0043790 A1 | 2/2005 | Seguin |
| 2005/0049674 A1 | 3/2005 | Berra et al. |
| 2005/0049692 A1 | 3/2005 | Numamoto et al. |
| 2005/0049696 A1 | 3/2005 | Siess et al. |
| 2005/0055088 A1 | 3/2005 | Liddicoat et al. |
| 2005/0060016 A1 | 3/2005 | Wu et al. |
| 2005/0060018 A1 | 3/2005 | Dittman |
| 2005/0060029 A1 | 3/2005 | Le et al. |
| 2005/0060030 A1 | 3/2005 | Lashinski et al. |
| 2005/0065594 A1 | 3/2005 | DiMatteo et al. |
| 2005/0070794 A1 | 3/2005 | Deal et al. |
| 2005/0070957 A1 | 3/2005 | Das |
| 2005/0075584 A1 | 4/2005 | Cali |
| 2005/0075662 A1 | 4/2005 | Pedersen et al. |
| 2005/0075712 A1 | 4/2005 | Biancucci et al. |
| 2005/0075717 A1 | 4/2005 | Nguyen et al. |
| 2005/0075719 A1 | 4/2005 | Bergheim |
| 2005/0075720 A1 | 4/2005 | Nguyen et al. |
| 2005/0075724 A1 | 4/2005 | Svanidze et al. |
| 2005/0075725 A1 | 4/2005 | Rowe |
| 2005/0075726 A1 | 4/2005 | Svanidze et al. |
| 2005/0075727 A1 | 4/2005 | Wheatley |
| 2005/0075730 A1 | 4/2005 | Myers et al. |
| 2005/0075731 A1 | 4/2005 | Artof et al. |
| 2005/0075776 A1 | 4/2005 | Cho |
| 2005/0084595 A1 | 4/2005 | Shukla et al. |
| 2005/0085841 A1 | 4/2005 | Eversull et al. |
| 2005/0085842 A1 | 4/2005 | Eversull et al. |
| 2005/0085843 A1 | 4/2005 | Opolski et al. |
| 2005/0085890 A1 | 4/2005 | Rasmussen et al. |
| 2005/0085900 A1 | 4/2005 | Case et al. |
| 2005/0090846 A1 | 4/2005 | Pedersen et al. |
| 2005/0090890 A1 | 4/2005 | Wu et al. |
| 2005/0096568 A1 | 5/2005 | Kato |
| 2005/0096692 A1 | 5/2005 | Linder et al. |
| 2005/0096724 A1 | 5/2005 | Stenzel et al. |
| 2005/0096726 A1 | 5/2005 | Sequin et al. |
| 2005/0096734 A1 | 5/2005 | Majercak et al. |
| 2005/0096735 A1 | 5/2005 | Hojeibane et al. |
| 2005/0096736 A1 | 5/2005 | Osse et al. |
| 2005/0096738 A1 | 5/2005 | Cali et al. |
| 2005/0096768 A1 | 5/2005 | Huang et al. |
| 2005/0098547 A1 | 5/2005 | Cali et al. |
| 2005/0100580 A1 | 5/2005 | Osborne et al. |
| 2005/0101903 A1 | 5/2005 | Kohler et al. |
| 2005/0101904 A1 | 5/2005 | Wilk |
| 2005/0101968 A1 | 5/2005 | Dadourian |
| 2005/0102020 A1 | 5/2005 | Grayzel et al. |
| 2005/0107822 A1 | 5/2005 | Wasdyke |
| 2005/0107871 A1 | 5/2005 | Realyvasquez et al. |
| 2005/0113902 A1 | 5/2005 | Geiser et al. |
| 2005/0113904 A1 | 5/2005 | Shank et al. |
| 2005/0113910 A1 | 5/2005 | Paniagua et al. |
| 2005/0119688 A1 | 6/2005 | Bergheim |
| 2005/0119728 A1 | 6/2005 | Sarac |
| 2005/0119736 A1 | 6/2005 | Zilla et al. |
| 2005/0125075 A1 | 6/2005 | Meade et al. |
| 2005/0131438 A1 | 6/2005 | Cohn |
| 2005/0137499 A1 | 6/2005 | Sheets et al. |
| 2005/0137609 A1 | 6/2005 | Guiraudon |
| 2005/0137681 A1 | 6/2005 | Shoemaker et al. |
| 2005/0137682 A1 | 6/2005 | Justino |
| 2005/0137683 A1 | 6/2005 | Hezi-Yamit et al. |
| 2005/0137686 A1 | 6/2005 | Salahieh et al. |
| 2005/0137687 A1 | 6/2005 | Salahieh et al. |
| 2005/0137688 A1 | 6/2005 | Salahieh et al. |
| 2005/0137689 A1 | 6/2005 | Salahieh et al. |
| 2005/0137690 A1 | 6/2005 | Salahieh et al. |
| 2005/0137691 A1 | 6/2005 | Salahieh et al. |
| 2005/0137692 A1 | 6/2005 | Haug et al. |
| 2005/0137693 A1 | 6/2005 | Haug et al. |
| 2005/0137694 A1 | 6/2005 | Haug et al. |
| 2005/0137695 A1 | 6/2005 | Salahieh et al. |
| 2005/0137696 A1 | 6/2005 | Salahieh et al. |
| 2005/0137697 A1 | 6/2005 | Salahieh et al. |
| 2005/0137698 A1 | 6/2005 | Salahieh et al. |
| 2005/0137699 A1 | 6/2005 | Salahieh et al. |
| 2005/0137701 A1 | 6/2005 | Salahieh et al. |
| 2005/0137702 A1 | 6/2005 | Haug et al. |
| 2005/0138689 A1 | 6/2005 | Aukerman |
| 2005/0143804 A1 | 6/2005 | Haverkost |
| 2005/0143807 A1 | 6/2005 | Pavcnik et al. |
| 2005/0143809 A1 | 6/2005 | Salahieh et al. |
| 2005/0148997 A1 | 7/2005 | Valley et al. |
| 2005/0149159 A1 | 7/2005 | Andreas et al. |
| 2005/0149166 A1 | 7/2005 | Schaeffer et al. |
| 2005/0149181 A1 | 7/2005 | Eberhardt |
| 2005/0150775 A1 | 7/2005 | Zhang et al. |
| 2005/0159726 A1 | 7/2005 | Evans et al. |
| 2005/0165352 A1 | 7/2005 | Henry et al. |
| 2005/0165477 A1 | 7/2005 | Anduiza et al. |
| 2005/0165479 A1 | 7/2005 | Drews et al. |
| 2005/0171597 A1 | 8/2005 | Boatman et al. |
| 2005/0171598 A1 | 8/2005 | Schaeffer |
| 2005/0177227 A1 | 8/2005 | Heim et al. |
| 2005/0182483 A1 | 8/2005 | Osborne et al. |
| 2005/0182486 A1 | 8/2005 | Gabbay |
| 2005/0186349 A1 | 8/2005 | Loper et al. |
| 2005/0187616 A1 | 8/2005 | Realyvasquez |
| 2005/0192527 A1 | 9/2005 | Gharib et al. |
| 2005/0192665 A1 | 9/2005 | Spenser et al. |
| 2005/0197694 A1 | 9/2005 | Pai et al. |
| 2005/0197695 A1 | 9/2005 | Stacchino et al. |
| 2005/0203549 A1 | 9/2005 | Realyvasquez |
| 2005/0203605 A1 | 9/2005 | Dolan |

(56) References Cited

U.S. PATENT DOCUMENTS

| | | |
|---|---|---|
| 2005/0203614 A1 | 9/2005 | Forster et al. |
| 2005/0203615 A1 | 9/2005 | Forster et al. |
| 2005/0203616 A1 | 9/2005 | Cribier |
| 2005/0203617 A1 | 9/2005 | Forster et al. |
| 2005/0203618 A1 | 9/2005 | Sharkawy et al. |
| 2005/0203818 A9 | 9/2005 | Rotman et al. |
| 2005/0209580 A1 | 9/2005 | Freyman |
| 2005/0214342 A1 | 9/2005 | Tweden et al. |
| 2005/0222664 A1 | 10/2005 | Parker |
| 2005/0222668 A1 | 10/2005 | Schaeffer et al. |
| 2005/0222674 A1 | 10/2005 | Paine |
| 2005/0228334 A1 | 10/2005 | Knudson et al. |
| 2005/0228472 A1 | 10/2005 | Case et al. |
| 2005/0228495 A1 | 10/2005 | Macoviak |
| 2005/0228496 A1 | 10/2005 | Mensah et al. |
| 2005/0234546 A1 | 10/2005 | Nugent et al. |
| 2005/0240200 A1 | 10/2005 | Bergheim |
| 2005/0240262 A1 | 10/2005 | White |
| 2005/0240263 A1 | 10/2005 | Fogarty et al. |
| 2005/0251243 A1 | 11/2005 | Seppala et al. |
| 2005/0251250 A1 | 11/2005 | Verhoeven et al. |
| 2005/0251251 A1 | 11/2005 | Cribier |
| 2005/0251252 A1 | 11/2005 | Stobie |
| 2005/0256532 A1 | 11/2005 | Nayak et al. |
| 2005/0261759 A1 | 11/2005 | Lambrecht et al. |
| 2005/0267523 A1 | 12/2005 | Devellian et al. |
| 2005/0267560 A1 | 12/2005 | Bates |
| 2005/0267567 A1 | 12/2005 | Shalev |
| 2005/0267573 A9 | 12/2005 | Macoviak et al. |
| 2005/0283231 A1 | 12/2005 | Haug et al. |
| 2005/0283962 A1 | 12/2005 | Boudjemline |
| 2005/0288627 A1 | 12/2005 | Mogul |
| 2005/0288685 A1 | 12/2005 | Gulles et al. |
| 2005/0288706 A1 | 12/2005 | Widomski et al. |
| 2006/0004439 A1 | 1/2006 | Spenser et al. |
| 2006/0004442 A1 | 1/2006 | Spenser et al. |
| 2006/0004469 A1 | 1/2006 | Sokel |
| 2006/0009841 A1 | 1/2006 | McGuckin, Jr. et al. |
| 2006/0009842 A1 | 1/2006 | Huynh et al. |
| 2006/0015168 A1 | 1/2006 | Gunderson |
| 2006/0025855 A1 | 2/2006 | Lashinski et al. |
| 2006/0025857 A1 | 2/2006 | Bergheim et al. |
| 2006/0028766 A1 | 2/2006 | Khizroev |
| 2006/0041218 A1 | 2/2006 | Phelps et al. |
| 2006/0047338 A1 | 3/2006 | Jenson et al. |
| 2006/0047343 A1 | 3/2006 | Oviatt et al. |
| 2006/0052736 A1 | 3/2006 | Tweden et al. |
| 2006/0052867 A1 | 3/2006 | Revuelta et al. |
| 2006/0058775 A1 | 3/2006 | Stevens et al. |
| 2006/0058864 A1 | 3/2006 | Schaeffer et al. |
| 2006/0058871 A1 | 3/2006 | Zakay et al. |
| 2006/0058872 A1 | 3/2006 | Salahieh et al. |
| 2006/0064151 A1 | 3/2006 | Guterman et al. |
| 2006/0069424 A1 | 3/2006 | Acosta et al. |
| 2006/0074477 A1 | 4/2006 | Berthiaume et al. |
| 2006/0074484 A1 | 4/2006 | Huber |
| 2006/0074485 A1 | 4/2006 | Realyvasquez |
| 2006/0077447 A1 | 4/2006 | Sojian et al. |
| 2006/0085060 A1 | 4/2006 | Campbell |
| 2006/0089711 A1 | 4/2006 | Dolan |
| 2006/0100685 A1 | 5/2006 | Seguin et al. |
| 2006/0111770 A1 | 5/2006 | Pavcnik et al. |
| 2006/0116757 A1 | 6/2006 | Lashinski et al. |
| 2006/0122692 A1 | 6/2006 | Gilad et al. |
| 2006/0135961 A1 | 6/2006 | Rosenman et al. |
| 2006/0135964 A1 | 6/2006 | Vesely |
| 2006/0136034 A1 | 6/2006 | Modesitt et al. |
| 2006/0142846 A1 | 6/2006 | Pavcnik et al. |
| 2006/0142848 A1 | 6/2006 | Gabbay |
| 2006/0149360 A1 | 7/2006 | Schwammenthal et al. |
| 2006/0155312 A1 | 7/2006 | Levine et al. |
| 2006/0155363 A1 | 7/2006 | LaDuca et al. |
| 2006/0155366 A1 | 7/2006 | LaDuca et al. |
| 2006/0161248 A1 | 7/2006 | Case et al. |
| 2006/0161249 A1 | 7/2006 | Realyvasquez et al. |
| 2006/0161265 A1 | 7/2006 | Levine et al. |
| 2006/0167474 A1 | 7/2006 | Bloom et al. |
| 2006/0167543 A1 | 7/2006 | Bailey et al. |
| 2006/0173524 A1 | 8/2006 | Salahieh et al. |
| 2006/0178740 A1 | 8/2006 | Stacchino et al. |
| 2006/0190070 A1 | 8/2006 | Dieck et al. |
| 2006/0193885 A1 | 8/2006 | Leonard Neethling et al. |
| 2006/0195134 A1 | 8/2006 | Crittenden |
| 2006/0195183 A1 | 8/2006 | Navia et al. |
| 2006/0195186 A1 | 8/2006 | Drews et al. |
| 2006/0206192 A1 | 9/2006 | Tower et al. |
| 2006/0206202 A1 | 9/2006 | Bonhoeffer et al. |
| 2006/0210597 A1 | 9/2006 | Hiles |
| 2006/0212110 A1 | 9/2006 | Osborne et al. |
| 2006/0212111 A1 | 9/2006 | Case et al. |
| 2006/0217802 A1 | 9/2006 | Ruiz et al. |
| 2006/0224183 A1 | 10/2006 | Freudenthal |
| 2006/0229561 A1 | 10/2006 | Huszar |
| 2006/0229700 A1 | 10/2006 | Acosta et al. |
| 2006/0229718 A1 | 10/2006 | Marquez |
| 2006/0229719 A1 | 10/2006 | Marquez et al. |
| 2006/0241745 A1 | 10/2006 | Solem |
| 2006/0246584 A1 | 11/2006 | Covelli |
| 2006/0247570 A1 | 11/2006 | Pokorney |
| 2006/0247763 A1 | 11/2006 | Slater |
| 2006/0253191 A1 | 11/2006 | Salahieh et al. |
| 2006/0259134 A1 | 11/2006 | Schwammenthal et al. |
| 2006/0259135 A1 | 11/2006 | Navia et al. |
| 2006/0259136 A1 | 11/2006 | Nguyen et al. |
| 2006/0259137 A1 | 11/2006 | Artof et al. |
| 2006/0265043 A1 | 11/2006 | Mandrusov et al. |
| 2006/0265056 A1 | 11/2006 | Nguyen et al. |
| 2006/0270958 A1 | 11/2006 | George |
| 2006/0271149 A1 | 11/2006 | Berez et al. |
| 2006/0271161 A1 | 11/2006 | Meyer et al. |
| 2006/0271166 A1 | 11/2006 | Thill et al. |
| 2006/0271175 A1 | 11/2006 | Woolfson et al. |
| 2006/0276872 A1 | 12/2006 | Arbefeuille et al. |
| 2006/0276873 A1 | 12/2006 | Sato |
| 2006/0276874 A1 | 12/2006 | Wilson et al. |
| 2006/0276882 A1 | 12/2006 | Case et al. |
| 2006/0276887 A1 | 12/2006 | Brady et al. |
| 2006/0282161 A1 | 12/2006 | Huynh et al. |
| 2006/0287668 A1 | 12/2006 | Fawzi et al. |
| 2006/0287717 A1 | 12/2006 | Rowe et al. |
| 2006/0287719 A1 | 12/2006 | Rowe et al. |
| 2006/0290027 A1 | 12/2006 | O'Connor et al. |
| 2006/0293745 A1 | 12/2006 | Carpentier et al. |
| 2007/0005129 A1 | 1/2007 | Damm et al. |
| 2007/0005131 A1 | 1/2007 | Taylor |
| 2007/0005132 A1 | 1/2007 | Simionescu et al. |
| 2007/0010876 A1 | 1/2007 | Salahieh et al. |
| 2007/0010877 A1 | 1/2007 | Salahieh et al. |
| 2007/0010878 A1 | 1/2007 | Rafiee et al. |
| 2007/0010887 A1 | 1/2007 | Williams et al. |
| 2007/0016286 A1 | 1/2007 | Herrmann et al. |
| 2007/0016288 A1 | 1/2007 | Gurskis et al. |
| 2007/0020248 A1 | 1/2007 | Everaerts et al. |
| 2007/0021826 A1 | 1/2007 | Case et al. |
| 2007/0027518 A1 | 2/2007 | Case et al. |
| 2007/0027520 A1 | 2/2007 | Sherburne |
| 2007/0027533 A1 | 2/2007 | Douk |
| 2007/0027535 A1 | 2/2007 | Purdy et al. |
| 2007/0032856 A1 | 2/2007 | Limon |
| 2007/0032879 A1 | 2/2007 | Levine et al. |
| 2007/0038291 A1 | 2/2007 | Case et al. |
| 2007/0038295 A1 | 2/2007 | Case et al. |
| 2007/0043420 A1 | 2/2007 | Lostetter |
| 2007/0043424 A1 | 2/2007 | Pryor |
| 2007/0043431 A1 | 2/2007 | Melsheimer |
| 2007/0043435 A1 | 2/2007 | Seguin et al. |
| 2007/0050014 A1 | 3/2007 | Johnson |
| 2007/0051377 A1 | 3/2007 | Douk et al. |
| 2007/0055340 A1 | 3/2007 | Pryor |
| 2007/0056346 A1 | 3/2007 | Spenser et al. |
| 2007/0060998 A1 | 3/2007 | Butterwick et al. |
| 2007/0061002 A1 | 3/2007 | Paul et al. |
| 2007/0061008 A1 | 3/2007 | Salahieh et al. |
| 2007/0073389 A1 | 3/2007 | Bolduc et al. |

(56) References Cited

U.S. PATENT DOCUMENTS

| | | |
|---|---|---|
| 2007/0073392 A1 | 3/2007 | Heyninck-Jantz et al. |
| 2007/0078504 A1 | 4/2007 | Mialhe |
| 2007/0078509 A1 | 4/2007 | Lotfy |
| 2007/0078510 A1 | 4/2007 | Ryan |
| 2007/0088431 A1 | 4/2007 | Bourang et al. |
| 2007/0093869 A1 | 4/2007 | Bloom et al. |
| 2007/0093887 A1 | 4/2007 | Case et al. |
| 2007/0100427 A1 | 5/2007 | Perouse |
| 2007/0100435 A1 | 5/2007 | Case et al. |
| 2007/0100439 A1 | 5/2007 | Cangialosi et al. |
| 2007/0100440 A1 | 5/2007 | Figulla et al. |
| 2007/0100449 A1 | 5/2007 | O'Neil et al. |
| 2007/0112355 A1 | 5/2007 | Salahieh et al. |
| 2007/0112358 A1 | 5/2007 | Abbott et al. |
| 2007/0112415 A1 | 5/2007 | Bartlett |
| 2007/0112422 A1 | 5/2007 | Dehdashtian |
| 2007/0118214 A1 | 5/2007 | Salahieh et al. |
| 2007/0123700 A1 | 5/2007 | Ueda et al. |
| 2007/0123979 A1 | 5/2007 | Perier et al. |
| 2007/0135889 A1 | 6/2007 | Moore et al. |
| 2007/0142906 A1 | 6/2007 | Figulla et al. |
| 2007/0142907 A1 | 6/2007 | Moaddeb et al. |
| 2007/0155010 A1 | 7/2007 | Farnsworth et al. |
| 2007/0156233 A1 | 7/2007 | Kapadia et al. |
| 2007/0162102 A1 | 7/2007 | Ryan et al. |
| 2007/0162103 A1 | 7/2007 | Case et al. |
| 2007/0162107 A1 | 7/2007 | Haug et al. |
| 2007/0162113 A1 | 7/2007 | Sharkawy et al. |
| 2007/0173918 A1 | 7/2007 | Dreher et al. |
| 2007/0173932 A1 | 7/2007 | Cali et al. |
| 2007/0179592 A1 | 8/2007 | Schaeffer |
| 2007/0179600 A1 | 8/2007 | Vardi |
| 2007/0185513 A1 | 8/2007 | Woolfson et al. |
| 2007/0185565 A1 | 8/2007 | Schwammenthal et al. |
| 2007/0185571 A1 | 8/2007 | Kapadia et al. |
| 2007/0198078 A1 | 8/2007 | Berra et al. |
| 2007/0198097 A1 | 8/2007 | Zegdi |
| 2007/0203391 A1 | 8/2007 | Bloom et al. |
| 2007/0203503 A1 | 8/2007 | Salahieh et al. |
| 2007/0203560 A1 | 8/2007 | Forster et al. |
| 2007/0203576 A1 | 8/2007 | Lee et al. |
| 2007/0208550 A1 | 9/2007 | Cao et al. |
| 2007/0213813 A1 | 9/2007 | Von Segesser et al. |
| 2007/0225681 A1 | 9/2007 | House |
| 2007/0225802 A1 | 9/2007 | Forsell |
| 2007/0232898 A1 | 10/2007 | Huynh et al. |
| 2007/0233222 A1 | 10/2007 | Roeder et al. |
| 2007/0233228 A1 | 10/2007 | Eberhardt et al. |
| 2007/0233237 A1 | 10/2007 | Krivoruchko |
| 2007/0233238 A1 | 10/2007 | Huynh et al. |
| 2007/0238979 A1 | 10/2007 | Huynh et al. |
| 2007/0239254 A1 | 10/2007 | Chia et al. |
| 2007/0239265 A1 | 10/2007 | Birdsall |
| 2007/0239266 A1 | 10/2007 | Birdsall |
| 2007/0239269 A1 | 10/2007 | Dolan et al. |
| 2007/0239271 A1 | 10/2007 | Nguyen |
| 2007/0239273 A1 | 10/2007 | Allen |
| 2007/0244543 A1 | 10/2007 | Mitchell |
| 2007/0244544 A1 | 10/2007 | Birdsall et al. |
| 2007/0244545 A1 | 10/2007 | Birdsall et al. |
| 2007/0244546 A1 | 10/2007 | Francis |
| 2007/0244551 A1 | 10/2007 | Stobie |
| 2007/0244552 A1 | 10/2007 | Salahieh et al. |
| 2007/0244553 A1 | 10/2007 | Rafiee et al. |
| 2007/0244554 A1 | 10/2007 | Rafiee et al. |
| 2007/0244555 A1 | 10/2007 | Rafiee et al. |
| 2007/0244556 A1 | 10/2007 | Rafiee et al. |
| 2007/0244557 A1 | 10/2007 | Rafiee et al. |
| 2007/0250151 A1 | 10/2007 | Pereira |
| 2007/0250160 A1 | 10/2007 | Rafiee |
| 2007/0255386 A1 | 11/2007 | Tenne |
| 2007/0255390 A1 | 11/2007 | Ducke et al. |
| 2007/0255394 A1 | 11/2007 | Ryan |
| 2007/0255396 A1 | 11/2007 | Douk et al. |
| 2007/0260301 A1 | 11/2007 | Chuter et al. |
| 2007/0260327 A1 | 11/2007 | Case et al. |
| 2007/0265701 A1 | 11/2007 | Gurskis et al. |
| 2007/0270751 A1 | 11/2007 | Stangenes et al. |
| 2007/0270943 A1 | 11/2007 | Solem et al. |
| 2007/0273813 A1 | 11/2007 | Yoshida et al. |
| 2007/0282436 A1 | 12/2007 | Pinchuk |
| 2007/0287717 A1 | 12/2007 | Fanning et al. |
| 2007/0288000 A1 | 12/2007 | Bonan |
| 2007/0288087 A1 | 12/2007 | Fearnot et al. |
| 2007/0288089 A1 | 12/2007 | Gurskis et al. |
| 2008/0004688 A1 | 1/2008 | Spenser et al. |
| 2008/0004696 A1 | 1/2008 | Vesely |
| 2008/0009934 A1 | 1/2008 | Schneider et al. |
| 2008/0009940 A1 | 1/2008 | Cribier |
| 2008/0015671 A1 | 1/2008 | Bonhoeffer |
| 2008/0021546 A1 | 1/2008 | Patz et al. |
| 2008/0021552 A1 | 1/2008 | Gabbay |
| 2008/0022504 A1 | 1/2008 | Melsheimer |
| 2008/0033534 A1 | 2/2008 | Cook et al. |
| 2008/0033541 A1 | 2/2008 | Gelbart et al. |
| 2008/0039925 A1 | 2/2008 | Ishimaru et al. |
| 2008/0039934 A1 | 2/2008 | Styrc |
| 2008/0045921 A1 | 2/2008 | Anderson et al. |
| 2008/0048656 A1 | 2/2008 | Tan et al. |
| 2008/0065001 A1 | 3/2008 | DiNucci et al. |
| 2008/0065011 A1 | 3/2008 | Marchand et al. |
| 2008/0065206 A1 | 3/2008 | Liddicoat |
| 2008/0071361 A1 | 3/2008 | Tuval et al. |
| 2008/0071362 A1 | 3/2008 | Tuval et al. |
| 2008/0071363 A1 | 3/2008 | Tuval et al. |
| 2008/0071366 A1 | 3/2008 | Tuval et al. |
| 2008/0071368 A1 | 3/2008 | Tuval et al. |
| 2008/0071369 A1 | 3/2008 | Tuval et al. |
| 2008/0077227 A1 | 3/2008 | Ouellette et al. |
| 2008/0077234 A1 | 3/2008 | Styrc |
| 2008/0077236 A1 | 3/2008 | Letac et al. |
| 2008/0082165 A1 | 4/2008 | Wilson et al. |
| 2008/0082166 A1 | 4/2008 | Styrc et al. |
| 2008/0086205 A1 | 4/2008 | Gordy et al. |
| 2008/0097586 A1 | 4/2008 | Pavcnik et al. |
| 2008/0102439 A1 | 5/2008 | Tian et al. |
| 2008/0109070 A1 | 5/2008 | Wagner et al. |
| 2008/0125859 A1 | 5/2008 | Salahieh et al. |
| 2008/0127707 A1 | 6/2008 | Kokish et al. |
| 2008/0133002 A1 | 6/2008 | Gelbart et al. |
| 2008/0133003 A1 | 6/2008 | Seguin et al. |
| 2008/0140188 A1 | 6/2008 | Rahdert et al. |
| 2008/0140189 A1 | 6/2008 | Nguyen et al. |
| 2008/0147105 A1 | 6/2008 | Wilson et al. |
| 2008/0147180 A1 | 6/2008 | Ghione et al. |
| 2008/0147181 A1 | 6/2008 | Ghione et al. |
| 2008/0147182 A1 | 6/2008 | Righini et al. |
| 2008/0154355 A1 | 6/2008 | Benichou et al. |
| 2008/0154356 A1 | 6/2008 | Obermiller et al. |
| 2008/0161909 A1 | 7/2008 | Kheradvar et al. |
| 2008/0161910 A1 | 7/2008 | Revuelta et al. |
| 2008/0161911 A1 | 7/2008 | Revuelta et al. |
| 2008/0172119 A1 | 7/2008 | Yamasaki et al. |
| 2008/0177381 A1 | 7/2008 | Navia et al. |
| 2008/0183273 A1 | 7/2008 | Mesana et al. |
| 2008/0188928 A1 | 8/2008 | Salahieh et al. |
| 2008/0195193 A1 | 8/2008 | Purdy et al. |
| 2008/0195199 A1 | 8/2008 | Kheradvar et al. |
| 2008/0200977 A1 | 8/2008 | Paul et al. |
| 2008/0208209 A1 | 8/2008 | Fischer et al. |
| 2008/0208327 A1 | 8/2008 | Rowe |
| 2008/0208328 A1 | 8/2008 | Antocci et al. |
| 2008/0208332 A1 | 8/2008 | Lamphere et al. |
| 2008/0215143 A1 | 9/2008 | Seguin |
| 2008/0215144 A1 | 9/2008 | Ryan et al. |
| 2008/0221672 A1 | 9/2008 | Lamphere et al. |
| 2008/0221703 A1 | 9/2008 | Que et al. |
| 2008/0228254 A1 | 9/2008 | Ryan |
| 2008/0228263 A1 | 9/2008 | Ryan |
| 2008/0234443 A1 | 9/2008 | Kiss et al. |
| 2008/0234797 A1 | 9/2008 | Styrc |
| 2008/0234814 A1 | 9/2008 | Salahieh et al. |
| 2008/0243246 A1 | 10/2008 | Ryan et al. |
| 2008/0255651 A1 | 10/2008 | Dwork |

(56) References Cited

U.S. PATENT DOCUMENTS

| | | |
|---|---|---|
| 2008/0255660 A1 | 10/2008 | Guyenot et al. |
| 2008/0255661 A1 | 10/2008 | Straubinger et al. |
| 2008/0262590 A1 | 10/2008 | Murray |
| 2008/0262592 A1 | 10/2008 | Jordan et al. |
| 2008/0262593 A1 | 10/2008 | Ryan et al. |
| 2008/0262602 A1 | 10/2008 | Wilk et al. |
| 2008/0264102 A1 | 10/2008 | Berra |
| 2008/0269878 A1 | 10/2008 | Iobbi |
| 2008/0275549 A1 | 11/2008 | Rowe |
| 2008/0275550 A1 | 11/2008 | Kheradvar et al. |
| 2008/0288054 A1 | 11/2008 | Pulnev et al. |
| 2009/0005863 A1 | 1/2009 | Goetz et al. |
| 2009/0012356 A1 | 1/2009 | Dann et al. |
| 2009/0012600 A1 | 1/2009 | Styrc et al. |
| 2009/0030512 A1 | 1/2009 | Thielen et al. |
| 2009/0048656 A1 | 2/2009 | Wen |
| 2009/0054968 A1 | 2/2009 | Bonhoeffer et al. |
| 2009/0054969 A1 | 2/2009 | Salahieh et al. |
| 2009/0054976 A1 | 2/2009 | Tuval et al. |
| 2009/0062908 A1 | 3/2009 | Bonhoeffer et al. |
| 2009/0069886 A1 | 3/2009 | Suri et al. |
| 2009/0069887 A1 | 3/2009 | Righini et al. |
| 2009/0069889 A1 | 3/2009 | Suri |
| 2009/0069890 A1 | 3/2009 | Suri |
| 2009/0076598 A1 | 3/2009 | Salahieh et al. |
| 2009/0082844 A1 | 3/2009 | Zacharias et al. |
| 2009/0082858 A1 | 3/2009 | Nugent et al. |
| 2009/0085900 A1 | 4/2009 | Weiner |
| 2009/0093876 A1 | 4/2009 | Nitzan et al. |
| 2009/0093877 A1 | 4/2009 | Keidar et al. |
| 2009/0099640 A1 | 4/2009 | Weng |
| 2009/0099641 A1 | 4/2009 | Wu et al. |
| 2009/0099643 A1 | 4/2009 | Hyodoh et al. |
| 2009/0099653 A1 | 4/2009 | Suri et al. |
| 2009/0112309 A1 | 4/2009 | Jaramillo et al. |
| 2009/0138079 A1 | 5/2009 | Tuval et al. |
| 2009/0157175 A1 | 6/2009 | Benichou |
| 2009/0163951 A1 | 6/2009 | Simmons et al. |
| 2009/0164004 A1 | 6/2009 | Cohn |
| 2009/0164006 A1 | 6/2009 | Seguin et al. |
| 2009/0171432 A1 | 7/2009 | Von Segesser et al. |
| 2009/0171447 A1 | 7/2009 | Von Segesser et al. |
| 2009/0171456 A1 | 7/2009 | Kveen et al. |
| 2009/0182405 A1 | 7/2009 | Arnault De La Menardiere et al. |
| 2009/0192585 A1 | 7/2009 | Bloom et al. |
| 2009/0192586 A1 | 7/2009 | Tabor et al. |
| 2009/0192591 A1 | 7/2009 | Ryan et al. |
| 2009/0192601 A1 | 7/2009 | Rafiee et al. |
| 2009/0198316 A1 | 8/2009 | Laske et al. |
| 2009/0198323 A1 | 8/2009 | Johnson et al. |
| 2009/0210052 A1 | 8/2009 | Forster et al. |
| 2009/0216310 A1 | 8/2009 | Straubinger et al. |
| 2009/0216312 A1 | 8/2009 | Straubinger et al. |
| 2009/0216313 A1 | 8/2009 | Straubinger et al. |
| 2009/0222076 A1 | 9/2009 | Figulla et al. |
| 2009/0222082 A1 | 9/2009 | Lock et al. |
| 2009/0234407 A1 | 9/2009 | Hastings et al. |
| 2009/0234443 A1 | 9/2009 | Ottma et al. |
| 2009/0240264 A1 | 9/2009 | Tuval et al. |
| 2009/0240320 A1 | 9/2009 | Tuval et al. |
| 2009/0248143 A1 | 10/2009 | Laham |
| 2009/0259306 A1 | 10/2009 | Rowe |
| 2009/0264759 A1 | 10/2009 | Byrd |
| 2009/0264997 A1 | 10/2009 | Salahieh et al. |
| 2009/0276040 A1 | 11/2009 | Rowe et al. |
| 2009/0281619 A1 | 11/2009 | Le et al. |
| 2009/0287290 A1 | 11/2009 | Macaulay et al. |
| 2009/0287296 A1 | 11/2009 | Manasse |
| 2009/0287299 A1 | 11/2009 | Tabor et al. |
| 2009/0299462 A1 | 12/2009 | Fawzi et al. |
| 2009/0319037 A1 | 12/2009 | Rowe et al. |
| 2010/0004739 A1 | 1/2010 | Vesely |
| 2010/0004740 A1 | 1/2010 | Seguin et al. |
| 2010/0011564 A1 | 1/2010 | Millwee et al. |
| 2010/0030328 A1 | 2/2010 | Seguin et al. |
| 2010/0036479 A1 | 2/2010 | Hill et al. |
| 2010/0036485 A1 | 2/2010 | Seguin |
| 2010/0049313 A1 | 2/2010 | Alon et al. |
| 2010/0057051 A1 | 3/2010 | Howat et al. |
| 2010/0057185 A1 | 3/2010 | Melsheimer et al. |
| 2010/0063573 A1 | 3/2010 | Hijlkema et al. |
| 2010/0069852 A1 | 3/2010 | Kelley |
| 2010/0069916 A1 | 3/2010 | Cully et al. |
| 2010/0070027 A1 | 3/2010 | Bonhoeffer et al. |
| 2010/0082089 A1 | 4/2010 | Quadri et al. |
| 2010/0082094 A1 | 4/2010 | Quadri et al. |
| 2010/0087913 A1 | 4/2010 | Rabkin et al. |
| 2010/0094399 A1 | 4/2010 | Dorn et al. |
| 2010/0094411 A1 | 4/2010 | Tuval et al. |
| 2010/0100167 A1 | 4/2010 | Bortlein et al. |
| 2010/0121434 A1 | 5/2010 | Paul et al. |
| 2010/0131054 A1 | 5/2010 | Tuval et al. |
| 2010/0131057 A1 | 5/2010 | Subramanian et al. |
| 2010/0137979 A1 | 6/2010 | Tuval et al. |
| 2010/0145439 A1 | 6/2010 | Seguin et al. |
| 2010/0152840 A1 | 6/2010 | Seguin et al. |
| 2010/0160725 A1 | 6/2010 | Kiser et al. |
| 2010/0161045 A1 | 6/2010 | Righini |
| 2010/0168839 A1 | 7/2010 | Braido et al. |
| 2010/0174362 A1 | 7/2010 | Straubinger et al. |
| 2010/0185275 A1 | 7/2010 | Richter et al. |
| 2010/0185277 A1 | 7/2010 | Braido et al. |
| 2010/0191320 A1 | 7/2010 | Straubinger et al. |
| 2010/0191326 A1 | 7/2010 | Alkhatib |
| 2010/0198346 A1 | 8/2010 | Keogh et al. |
| 2010/0210991 A1 | 8/2010 | Wilk et al. |
| 2010/0219092 A1 | 9/2010 | Salahieh et al. |
| 2010/0234932 A1 | 9/2010 | Arbefeuille et al. |
| 2010/0234940 A1 | 9/2010 | Dolan |
| 2010/0239917 A1 | 9/2010 | Lee et al. |
| 2010/0249908 A1 | 9/2010 | Chau et al. |
| 2010/0249915 A1 | 9/2010 | Zhang |
| 2010/0249916 A1 | 9/2010 | Zhang |
| 2010/0249917 A1 | 9/2010 | Zhang |
| 2010/0249918 A1 | 9/2010 | Zhang |
| 2010/0256723 A1 | 10/2010 | Murray |
| 2010/0262231 A1 | 10/2010 | Tuval et al. |
| 2010/0268332 A1 | 10/2010 | Tuval et al. |
| 2010/0280459 A1 | 11/2010 | Werner |
| 2010/0280495 A1 | 11/2010 | Paul et al. |
| 2010/0286768 A1 | 11/2010 | Alkhatib |
| 2010/0292779 A1 | 11/2010 | Straubinger et al. |
| 2010/0292780 A1 | 11/2010 | Straubinger et al. |
| 2010/0292785 A1 | 11/2010 | Seguin et al. |
| 2010/0298931 A1 | 11/2010 | Quadri et al. |
| 2011/0004297 A1 | 1/2011 | Sogard et al. |
| 2011/0015616 A1 | 1/2011 | Straubinger et al. |
| 2011/0022157 A1 | 1/2011 | Essinger et al. |
| 2011/0029066 A1 | 2/2011 | Gilad et al. |
| 2011/0034852 A1 | 2/2011 | Hausler et al. |
| 2011/0040366 A1 | 2/2011 | Goetz et al. |
| 2011/0040374 A1 | 2/2011 | Goetz et al. |
| 2011/0071613 A1 | 3/2011 | Wood et al. |
| 2011/0093007 A1 | 4/2011 | Abbott et al. |
| 2011/0098805 A1 | 4/2011 | Dwork et al. |
| 2011/0106244 A1 | 5/2011 | Ferrari et al. |
| 2011/0118545 A1 | 5/2011 | Williams et al. |
| 2011/0137397 A1 | 6/2011 | Chau et al. |
| 2011/0166637 A1 | 7/2011 | Irwin et al. |
| 2011/0190862 A1 | 8/2011 | Bashiri et al. |
| 2011/0190874 A1 | 8/2011 | Celermajer et al. |
| 2011/0208290 A1 | 8/2011 | Straubinger et al. |
| 2011/0208297 A1 | 8/2011 | Tuval et al. |
| 2011/0224780 A1 | 9/2011 | Tabor et al. |
| 2011/0238159 A1 | 9/2011 | Guyenot et al. |
| 2011/0238167 A1 | 9/2011 | Dove et al. |
| 2011/0257729 A1 | 10/2011 | Spenser et al. |
| 2011/0257733 A1 | 10/2011 | Dwork |
| 2011/0257735 A1 | 10/2011 | Salahieh et al. |
| 2011/0264191 A1 | 10/2011 | Rothstein |
| 2011/0264196 A1 | 10/2011 | Savage et al. |
| 2011/0264203 A1 | 10/2011 | Dwork et al. |
| 2011/0276121 A1 | 11/2011 | Levine |
| 2011/0276129 A1 | 11/2011 | Salahieh et al. |

(56) References Cited

U.S. PATENT DOCUMENTS

| | | |
|---|---|---|
| 2011/0288626 A1 | 11/2011 | Straubinger et al. |
| 2011/0288634 A1 | 11/2011 | Tuval et al. |
| 2011/0295363 A1 | 12/2011 | Girard et al. |
| 2011/0319989 A1 | 12/2011 | Lane et al. |
| 2012/0016469 A1 | 1/2012 | Salahieh et al. |
| 2012/0016471 A1 | 1/2012 | Salahieh et al. |
| 2012/0022633 A1 | 1/2012 | Olson et al. |
| 2012/0022642 A1 | 1/2012 | Haug et al. |
| 2012/0029627 A1 | 2/2012 | Salahieh et al. |
| 2012/0035719 A1 | 2/2012 | Forster et al. |
| 2012/0035720 A1 | 2/2012 | Cali et al. |
| 2012/0041547 A1 | 2/2012 | Duffy et al. |
| 2012/0041549 A1 | 2/2012 | Salahieh et al. |
| 2012/0041550 A1 | 2/2012 | Salahieh et al. |
| 2012/0046740 A1 | 2/2012 | Paul et al. |
| 2012/0053683 A1 | 3/2012 | Salahieh et al. |
| 2012/0059447 A1 | 3/2012 | Zilla et al. |
| 2012/0065464 A1 | 3/2012 | Ellis et al. |
| 2012/0078347 A1 | 3/2012 | Braido et al. |
| 2012/0078357 A1 | 3/2012 | Conklin |
| 2012/0078360 A1 | 3/2012 | Rafiee |
| 2012/0089224 A1 | 4/2012 | Haug et al. |
| 2012/0100182 A1 | 4/2012 | Mooney et al. |
| 2012/0101571 A1 | 4/2012 | Thambar et al. |
| 2012/0101572 A1 | 4/2012 | Kovalsky et al. |
| 2012/0116496 A1 | 5/2012 | Chuter et al. |
| 2012/0123515 A1 | 5/2012 | Hosford et al. |
| 2012/0123529 A1 | 5/2012 | Levi et al. |
| 2012/0130468 A1 | 5/2012 | Khosravi et al. |
| 2012/0132547 A1 | 5/2012 | Salahieh et al. |
| 2012/0136430 A1 | 5/2012 | Sochman et al. |
| 2012/0143084 A1 | 6/2012 | Shoham |
| 2012/0165957 A1 | 6/2012 | Everland et al. |
| 2012/0172982 A1 | 7/2012 | Stacchino et al. |
| 2012/0179244 A1 | 7/2012 | Schankereli et al. |
| 2012/0185030 A1 | 7/2012 | Igaki et al. |
| 2012/0197379 A1 | 8/2012 | Laske et al. |
| 2012/0209374 A1 | 8/2012 | Bonhoeffer et al. |
| 2012/0209376 A1 | 8/2012 | Hauser et al. |
| 2012/0221100 A1 | 8/2012 | Huber |
| 2012/0226341 A1 | 9/2012 | Schreck et al. |
| 2012/0283715 A1 | 11/2012 | Mihalik et al. |
| 2012/0283823 A1 | 11/2012 | Bonhoeffer et al. |
| 2012/0303113 A1 | 11/2012 | Benichou et al. |
| 2012/0303116 A1 | 11/2012 | Gorman, III et al. |
| 2012/0305441 A1 | 12/2012 | Murray et al. |
| 2012/0310332 A1 | 12/2012 | Murray et al. |
| 2012/0316637 A1 | 12/2012 | Holm et al. |
| 2012/0330408 A1 | 12/2012 | Hillukka et al. |
| 2012/0330409 A1 | 12/2012 | Haug et al. |
| 2013/0013057 A1 | 1/2013 | Salahieh et al. |
| 2013/0018457 A1 | 1/2013 | Gregg et al. |
| 2013/0023984 A1 | 1/2013 | Conklin |
| 2013/0030519 A1 | 1/2013 | Tran et al. |
| 2013/0030520 A1 | 1/2013 | Lee et al. |
| 2013/0046373 A1 | 2/2013 | Cartledge et al. |
| 2013/0053949 A1 | 2/2013 | Pintor et al. |
| 2013/0066342 A1 | 3/2013 | Dell et al. |
| 2013/0066419 A1 | 3/2013 | Gregg |
| 2013/0071441 A1 | 3/2013 | Iwazawa et al. |
| 2013/0073037 A1 | 3/2013 | Gregg et al. |
| 2013/0079867 A1 | 3/2013 | Hoffman et al. |
| 2013/0079869 A1 | 3/2013 | Straubinger et al. |
| 2013/0089655 A1 | 4/2013 | Gregg |
| 2013/0090728 A1 | 4/2013 | Solem |
| 2013/0090729 A1 | 4/2013 | Gregg et al. |
| 2013/0096664 A1 | 4/2013 | Goetz et al. |
| 2013/0116778 A1 | 5/2013 | Gregg et al. |
| 2013/0118949 A1 | 5/2013 | Chang et al. |
| 2013/0123757 A1 | 5/2013 | Crisostomo et al. |
| 2013/0123795 A1 | 5/2013 | Gamarra et al. |
| 2013/0123796 A1 | 5/2013 | Sutton et al. |
| 2013/0123898 A1 | 5/2013 | Tung et al. |
| 2013/0138207 A1 | 5/2013 | Quadri et al. |
| 2013/0144203 A1 | 6/2013 | Wilk et al. |
| 2013/0144276 A1 | 6/2013 | Crisostomo et al. |
| 2013/0158653 A1 | 6/2013 | Gamarra et al. |
| 2013/0158655 A1 | 6/2013 | Sutton et al. |
| 2013/0158656 A1 | 6/2013 | Sutton et al. |
| 2013/0166017 A1 | 6/2013 | Cartledge et al. |
| 2013/0178930 A1 | 7/2013 | Straubinger et al. |
| 2013/0184813 A1 | 7/2013 | Quadri et al. |
| 2013/0190865 A1 | 7/2013 | Anderson |
| 2013/0204359 A1 | 8/2013 | Thubrikar et al. |
| 2013/0231735 A1 | 9/2013 | Deem et al. |
| 2013/0245752 A1 | 9/2013 | Goetz et al. |
| 2013/0253342 A1 | 9/2013 | Griswold et al. |
| 2013/0253635 A1 | 9/2013 | Straubinger et al. |
| 2013/0253640 A1 | 9/2013 | Meiri et al. |
| 2013/0268067 A1 | 10/2013 | Forster et al. |
| 2013/0274865 A1 | 10/2013 | Haverkost et al. |
| 2013/0274870 A1 | 10/2013 | Lombardi et al. |
| 2013/0289698 A1 | 10/2013 | Wang et al. |
| 2013/0296999 A1 | 11/2013 | Burriesci et al. |
| 2013/0304199 A1 | 11/2013 | Sutton et al. |
| 2013/0310917 A1 | 11/2013 | Richter et al. |
| 2013/0310923 A1 | 11/2013 | Kheradvar et al. |
| 2013/0310928 A1 | 11/2013 | Morriss et al. |
| 2013/0325101 A1 | 12/2013 | Goetz et al. |
| 2013/0338755 A1 | 12/2013 | Goetz et al. |
| 2013/0345799 A1 | 12/2013 | Lafontaine |
| 2014/0012368 A1 | 1/2014 | Sugimoto et al. |
| 2014/0012370 A1 | 1/2014 | Bonhoeffer et al. |
| 2014/0018911 A1 | 1/2014 | Zhou et al. |
| 2014/0052239 A1 | 2/2014 | Kong et al. |
| 2014/0058501 A1 | 2/2014 | Bonhoeffer et al. |
| 2014/0083190 A1 | 3/2014 | Kaack et al. |
| 2014/0088680 A1 | 3/2014 | Costello et al. |
| 2014/0094904 A1 | 4/2014 | Salahieh et al. |
| 2014/0114390 A1 | 4/2014 | Tobis et al. |
| 2014/0114405 A1 | 4/2014 | Paul et al. |
| 2014/0114406 A1 | 4/2014 | Salahieh et al. |
| 2014/0114407 A1 | 4/2014 | Rajamannan |
| 2014/0121763 A1 | 5/2014 | Duffy et al. |
| 2014/0121766 A1 | 5/2014 | Salahieh et al. |
| 2014/0128969 A1 | 5/2014 | Hill et al. |
| 2014/0135909 A1 | 5/2014 | Carr et al. |
| 2014/0135912 A1 | 5/2014 | Salahieh et al. |
| 2014/0207229 A1 | 7/2014 | Shoemaker et al. |
| 2014/0222142 A1 | 8/2014 | Kovalsky et al. |
| 2014/0236287 A1 | 8/2014 | Clague et al. |
| 2014/0243962 A1 | 8/2014 | Wilson et al. |
| 2014/0243963 A1 | 8/2014 | Sheps et al. |
| 2014/0243967 A1 | 8/2014 | Salahieh et al. |
| 2014/0249621 A1 | 9/2014 | Eidenschink |
| 2014/0257473 A1 | 9/2014 | Rajamannan |
| 2014/0277414 A1 | 9/2014 | Kheradvar |
| 2014/0296962 A1 | 10/2014 | Cartledge et al. |
| 2014/0309732 A1 | 10/2014 | Solem |
| 2014/0316518 A1 | 10/2014 | Kheradvar et al. |
| 2014/0330371 A1 | 11/2014 | Gloss et al. |
| 2014/0343669 A1 | 11/2014 | Lane et al. |
| 2014/0364799 A1 | 12/2014 | Beauvais et al. |
| 2014/0379068 A1 | 12/2014 | Thielen et al. |
| 2015/0012085 A1 | 1/2015 | Salahieh et al. |
| 2015/0032056 A1 | 1/2015 | Okamura et al. |
| 2015/0032198 A1 | 1/2015 | Folk |
| 2015/0073540 A1 | 3/2015 | Salahieh et al. |
| 2015/0073541 A1 | 3/2015 | Salahieh et al. |
| 2015/0088252 A1 | 3/2015 | Jenson et al. |
| 2015/0094804 A1 | 4/2015 | Bonhoeffer et al. |
| 2015/0105857 A1 | 4/2015 | Bonhoeffer et al. |
| 2015/0127092 A1 | 5/2015 | Straubinger et al. |
| 2015/0127094 A1 | 5/2015 | Salahieh et al. |
| 2015/0142102 A1 | 5/2015 | Lafontaine et al. |
| 2015/0148894 A1 | 5/2015 | Damm et al. |
| 2015/0209142 A1 | 7/2015 | Paul et al. |
| 2015/0209146 A1 | 7/2015 | Hill et al. |
| 2015/0223933 A1 | 8/2015 | Haug et al. |
| 2015/0238315 A1 | 8/2015 | Rabito et al. |
| 2015/0245909 A1 | 9/2015 | Salahieh et al. |
| 2015/0272731 A1 | 10/2015 | Racchini et al. |
| 2015/0320557 A1 | 11/2015 | Sutton et al. |
| 2015/0335423 A1 | 11/2015 | Gregg et al. |

(56) References Cited

U.S. PATENT DOCUMENTS

| | | | |
|---|---|---|---|
| 2015/0352252 A1 | 12/2015 | Nakamura et al. |
| 2015/0359997 A1 | 12/2015 | Crisostomo et al. |
| 2016/0022418 A1 | 1/2016 | Salahieh et al. |
| 2016/0045306 A1 | 2/2016 | Agrawal et al. |
| 2016/0045307 A1 | 2/2016 | Yohanan et al. |
| 2016/0051362 A1 | 2/2016 | Cooper et al. |
| 2016/0067040 A1 | 3/2016 | Agrawal et al. |
| 2016/0120645 A1 | 5/2016 | Alon |
| 2016/0135951 A1 | 5/2016 | Salahieh et al. |
| 2016/0143731 A1 | 5/2016 | Backus et al. |
| 2016/0158003 A1 | 6/2016 | Wallace et al. |
| 2016/0166384 A1 | 6/2016 | Olson et al. |
| 2016/0199184 A1 | 7/2016 | Ma et al. |
| 2016/0206423 A1 | 7/2016 | O'Connor et al. |
| 2016/0213467 A1 | 7/2016 | Backus et al. |
| 2016/0220359 A1 | 8/2016 | Backus et al. |
| 2016/0220360 A1 | 8/2016 | Lin et al. |
| 2016/0220365 A1 | 8/2016 | Backus et al. |
| 2016/0250024 A1 | 9/2016 | Hill et al. |
| 2016/0256271 A1 | 9/2016 | Backus et al. |
| 2016/0262878 A1 | 9/2016 | Backus et al. |
| 2016/0346107 A1 | 12/2016 | Matthison-Hansen et al. |
| 2016/0354203 A1 | 12/2016 | Tuval et al. |
| 2016/0374793 A1 | 12/2016 | Lafontaine et al. |
| 2016/0376063 A1 | 12/2016 | Salahieh et al. |
| 2017/0000609 A1 | 1/2017 | Gross et al. |
| 2017/0007400 A1 | 1/2017 | Sogard et al. |
| 2017/0027654 A1 | 2/2017 | Frimer et al. |
| 2017/0027693 A1 | 2/2017 | Paul et al. |
| 2017/0049563 A1 | 2/2017 | Straubinger et al. |
| 2017/0049568 A1 | 2/2017 | Straubinger et al. |
| 2017/0056172 A1 | 3/2017 | Salahieh et al. |
| 2017/0065410 A1 | 3/2017 | Straubinger et al. |
| 2017/0087343 A1 | 3/2017 | Assaf et al. |
| 2017/0095595 A1 | 4/2017 | Nakamura |
| 2017/0212723 A1 | 7/2017 | Atarot et al. |
| 2017/0265849 A1 | 9/2017 | Assaf et al. |
| 2017/0325954 A1 | 11/2017 | Perszyk |
| 2017/0333230 A1 | 11/2017 | Folan et al. |
| 2017/0348013 A1 | 12/2017 | Mottola et al. |
| 2018/0116843 A1 | 5/2018 | Schreck et al. |
| 2018/0325604 A1 | 11/2018 | Atarot et al. |
| 2018/0368976 A1 | 12/2018 | Bonhoeffer et al. |
| 2019/0328522 A1 | 10/2019 | Straubinger et al. |
| 2020/0054449 A1 | 2/2020 | Min et al. |
| 2021/0038313 A1 | 2/2021 | Sholev et al. |
| 2021/0322153 A1 | 10/2021 | Tuval et al. |
| 2022/0061987 A1 | 3/2022 | Duffy |
| 2022/0079747 A1 | 3/2022 | Girard et al. |
| 2022/0192765 A1 | 6/2022 | Brasset et al. |
| 2022/0304803 A1 | 9/2022 | Guyenot et al. |
| 2024/0148503 A1 | 5/2024 | Chu et al. |
| 2024/0164902 A1 | 5/2024 | Lee et al. |
| 2024/0164903 A1 | 5/2024 | Chu et al. |

FOREIGN PATENT DOCUMENTS

| | | |
|---|---|---|
| AU | 777443 B2 | 10/2004 |
| AU | 778831 B2 | 12/2004 |
| AU | 2004231189 A1 | 12/2004 |
| AU | 2004242527 A1 | 1/2005 |
| AU | 2001281277 B2 | 9/2005 |
| AU | 2006308187 A1 | 5/2007 |
| AU | 2006310681 A1 | 5/2007 |
| AU | 2006328896 A1 | 6/2007 |
| AU | 2002329324 B2 | 7/2007 |
| AU | 2007294199 A1 | 3/2008 |
| AU | 2008305600 A1 | 4/2009 |
| AU | 2009200985 A1 | 4/2009 |
| AU | 2006328896 B2 | 8/2013 |
| CA | 2378589 A1 | 2/2001 |
| CA | 2381192 A1 | 2/2001 |
| CA | 2385662 A1 | 3/2001 |
| CA | 2407987 A1 | 11/2001 |
| CA | 2418958 A1 | 2/2002 |
| CA | 2435962 A1 | 8/2002 |
| CA | 2457755 A1 | 2/2003 |
| CA | 2436258 A1 | 1/2005 |
| CA | 2848485 A1 | 1/2005 |
| CA | 2848490 A1 | 1/2005 |
| CA | 2595233 A1 | 7/2006 |
| CA | 2627409 A1 | 5/2007 |
| CA | 2627555 A1 | 5/2007 |
| CA | 2634358 A1 | 6/2007 |
| CA | 2657839 A1 | 3/2008 |
| CA | 2659690 A1 | 3/2008 |
| CN | 1338951 A | 3/2002 |
| CN | 1342443 A | 4/2002 |
| CN | 1745727 A | 3/2006 |
| CN | 2762776 Y | 3/2006 |
| CN | 1897892 A | 1/2007 |
| CN | 2933337 Y | 8/2007 |
| CN | 101011298 A | 8/2007 |
| CN | 101431963 A | 5/2009 |
| CN | 101605509 A | 12/2009 |
| CN | 101623217 A | 1/2010 |
| CN | 101700199 A | 5/2010 |
| CN | 101720211 A | 6/2010 |
| CN | 102271626 A | 12/2011 |
| CN | 102413793 A | 4/2012 |
| CN | 103118630 A | 5/2013 |
| DE | 2815756 A1 | 10/1979 |
| DE | 3640745 A1 | 6/1987 |
| DE | 3920657 A1 | 1/1991 |
| DE | 3640745 C2 | 3/1992 |
| DE | 4316971 A1 | 11/1994 |
| DE | 19532846 A1 | 3/1997 |
| DE | 19546692 A1 | 6/1997 |
| DE | 19633901 A1 | 2/1998 |
| DE | 20003874 U1 | 5/2000 |
| DE | 19857887 A1 | 7/2000 |
| DE | 19907646 A1 | 8/2000 |
| DE | 10010073 A1 | 9/2001 |
| DE | 10010074 A1 | 10/2001 |
| DE | 10034105 C1 | 4/2002 |
| DE | 10049812 A1 | 4/2002 |
| DE | 10049813 C1 | 4/2002 |
| DE | 10049814 A1 | 4/2002 |
| DE | 10049815 A1 | 4/2002 |
| DE | 10048814 A1 | 5/2002 |
| DE | 10121210 A1 | 11/2002 |
| DE | 19546692 C2 | 11/2002 |
| DE | 10301026 A1 | 2/2004 |
| DE | 10048814 B4 | 4/2004 |
| DE | 10049812 B4 | 6/2004 |
| DE | 10302447 A1 | 7/2004 |
| DE | 10335948 B3 | 2/2005 |
| DE | 10010074 B4 | 4/2005 |
| DE | 19857887 B4 | 5/2005 |
| DE | 10049815 B4 | 10/2005 |
| DE | 10010073 B4 | 12/2005 |
| DE | 102005003632 A1 | 8/2006 |
| DE | 102005051849 A1 | 5/2007 |
| DE | 102005052628 A1 | 5/2007 |
| DE | 202007005491 U1 | 6/2007 |
| DE | 20221871 U1 | 9/2008 |
| DE | 69937568 T2 | 9/2008 |
| DK | 1112042 T3 | 2/2008 |
| DK | 200800058 U1 | 6/2008 |
| DK | 200800058 U3 | 7/2008 |
| DK | 1259195 T3 | 2/2009 |
| DK | 1281375 T3 | 5/2012 |
| EP | 0084395 A1 | 7/1983 |
| EP | 0103546 A1 | 3/1984 |
| EP | 0103546 B1 | 5/1988 |
| EP | 0144167 B1 | 11/1989 |
| EP | 0402036 A1 | 12/1990 |
| EP | 0402176 A2 | 12/1990 |
| EP | 0411118 A1 | 2/1991 |
| EP | 0458877 A1 | 12/1991 |
| EP | 0515324 A1 | 11/1992 |
| EP | 0547135 A1 | 6/1993 |
| EP | 0579523 A1 | 1/1994 |
| EP | 0402176 B1 | 4/1994 |

(56) References Cited

FOREIGN PATENT DOCUMENTS

| | | |
|---|---|---|
| EP | 0592410 A1 | 4/1994 |
| EP | 0597967 A1 | 5/1994 |
| EP | 0597967 A4 | 12/1994 |
| EP | 0458877 B1 | 5/1995 |
| EP | 0657147 A2 | 6/1995 |
| EP | 0592410 B1 | 10/1995 |
| EP | 0696447 A2 | 2/1996 |
| EP | 0402036 B1 | 4/1996 |
| EP | 0729364 A1 | 9/1996 |
| EP | 0732088 A2 | 9/1996 |
| EP | 0756498 A1 | 2/1997 |
| EP | 0409929 B1 | 4/1997 |
| EP | 0778775 A1 | 6/1997 |
| EP | 0786970 A1 | 8/1997 |
| EP | 0792624 A1 | 9/1997 |
| EP | 0797957 A1 | 10/1997 |
| EP | 0797958 A1 | 10/1997 |
| EP | 0799604 A1 | 10/1997 |
| EP | 0801928 A1 | 10/1997 |
| EP | 0815798 A2 | 1/1998 |
| EP | 0826346 A1 | 3/1998 |
| EP | 0829239 A1 | 3/1998 |
| EP | 0836834 A2 | 4/1998 |
| EP | 0850607 A1 | 7/1998 |
| EP | 0853921 A2 | 7/1998 |
| EP | 0858779 A1 | 8/1998 |
| EP | 0871414 A1 | 10/1998 |
| EP | 0876796 A2 | 11/1998 |
| EP | 0876803 A2 | 11/1998 |
| EP | 0778775 B1 | 1/1999 |
| EP | 0888142 A1 | 1/1999 |
| EP | 0888750 A1 | 1/1999 |
| EP | 0895752 A1 | 2/1999 |
| EP | 0896813 A2 | 2/1999 |
| EP | 0903122 A2 | 3/1999 |
| EP | 0876796 A3 | 5/1999 |
| EP | 0928615 A1 | 7/1999 |
| EP | 0657147 B1 | 8/1999 |
| EP | 0934728 A2 | 8/1999 |
| EP | 0938877 A2 | 9/1999 |
| EP | 0943302 A2 | 9/1999 |
| EP | 0597967 B1 | 12/1999 |
| EP | 0696447 B1 | 1/2000 |
| EP | 0971649 A1 | 1/2000 |
| EP | 0986348 A1 | 3/2000 |
| EP | 1000590 A1 | 5/2000 |
| EP | 1011523 A1 | 6/2000 |
| EP | 1020166 A1 | 7/2000 |
| EP | 1027870 A1 | 8/2000 |
| EP | 1041942 A1 | 10/2000 |
| EP | 1041943 A1 | 10/2000 |
| EP | 1051204 A2 | 11/2000 |
| EP | 1057459 A1 | 12/2000 |
| EP | 1057460 A1 | 12/2000 |
| EP | 1078610 A2 | 2/2001 |
| EP | 1088529 A2 | 4/2001 |
| EP | 1089676 A2 | 4/2001 |
| EP | 1093771 A2 | 4/2001 |
| EP | 1097676 A1 | 5/2001 |
| EP | 1112042 A1 | 7/2001 |
| EP | 1112097 A1 | 7/2001 |
| EP | 1117446 A1 | 7/2001 |
| EP | 1158937 A1 | 12/2001 |
| EP | 0547135 B1 | 1/2002 |
| EP | 0729364 B1 | 1/2002 |
| EP | 1164976 A1 | 1/2002 |
| EP | 1166721 A2 | 1/2002 |
| EP | 1171061 A1 | 1/2002 |
| EP | 1206179 A1 | 5/2002 |
| EP | 0756498 B1 | 7/2002 |
| EP | 1233731 A1 | 8/2002 |
| EP | 0986348 B1 | 9/2002 |
| EP | 1235537 A1 | 9/2002 |
| EP | 1248655 A1 | 10/2002 |
| EP | 1251804 A1 | 10/2002 |
| EP | 1251805 A2 | 10/2002 |
| EP | 1255510 A1 | 11/2002 |
| EP | 1257305 A1 | 11/2002 |
| EP | 1259193 A1 | 11/2002 |
| EP | 1259195 A1 | 11/2002 |
| EP | 0959815 B1 | 12/2002 |
| EP | 0971649 B1 | 12/2002 |
| EP | 1262201 A1 | 12/2002 |
| EP | 1264582 A2 | 12/2002 |
| EP | 1281357 A2 | 2/2003 |
| EP | 1281375 A2 | 2/2003 |
| EP | 0888142 B1 | 5/2003 |
| EP | 1112097 B1 | 6/2003 |
| EP | 1330213 A1 | 7/2003 |
| EP | 0937439 B1 | 9/2003 |
| EP | 1017868 B1 | 9/2003 |
| EP | 1340473 A2 | 9/2003 |
| EP | 1347785 A1 | 10/2003 |
| EP | 1354569 A1 | 10/2003 |
| EP | 1356793 A2 | 10/2003 |
| EP | 1281375 A3 | 12/2003 |
| EP | 1340473 A3 | 2/2004 |
| EP | 1041943 B1 | 3/2004 |
| EP | 1356793 A3 | 3/2004 |
| EP | 1395208 A1 | 3/2004 |
| EP | 1401359 A2 | 3/2004 |
| EP | 0871414 B1 | 4/2004 |
| EP | 1406561 A2 | 4/2004 |
| EP | 1408882 A1 | 4/2004 |
| EP | 1042045 B1 | 5/2004 |
| EP | 1414295 A2 | 5/2004 |
| EP | 0819013 B1 | 6/2004 |
| EP | 1430853 A2 | 6/2004 |
| EP | 1347785 B1 | 7/2004 |
| EP | 1435878 A1 | 7/2004 |
| EP | 1435879 A1 | 7/2004 |
| EP | 1439800 A2 | 7/2004 |
| EP | 1441672 A1 | 8/2004 |
| EP | 0954248 B1 | 9/2004 |
| EP | 1452153 A1 | 9/2004 |
| EP | 0987998 B1 | 10/2004 |
| EP | 1206179 B1 | 10/2004 |
| EP | 1469797 A1 | 10/2004 |
| EP | 1087727 B1 | 11/2004 |
| EP | 1115452 B1 | 11/2004 |
| EP | 1117446 B1 | 11/2004 |
| EP | 1472996 A1 | 11/2004 |
| EP | 1477202 A2 | 11/2004 |
| EP | 1107710 B1 | 12/2004 |
| EP | 1233731 B1 | 12/2004 |
| EP | 1484081 A1 | 12/2004 |
| EP | 1494616 A2 | 1/2005 |
| EP | 1499366 A1 | 1/2005 |
| EP | 1143879 B1 | 3/2005 |
| EP | 1516599 A2 | 3/2005 |
| EP | 1518518 A2 | 3/2005 |
| EP | 1229864 B1 | 4/2005 |
| EP | 1253875 B1 | 4/2005 |
| EP | 1519697 A1 | 4/2005 |
| EP | 1521414 A1 | 4/2005 |
| EP | 1522278 A2 | 4/2005 |
| EP | 1088529 B1 | 6/2005 |
| EP | 1093771 B1 | 6/2005 |
| EP | 1251803 B1 | 6/2005 |
| EP | 1430853 A3 | 6/2005 |
| EP | 1539047 A2 | 6/2005 |
| EP | 1547533 A2 | 6/2005 |
| EP | 1059894 B1 | 7/2005 |
| EP | 1551274 A2 | 7/2005 |
| EP | 1551336 A1 | 7/2005 |
| EP | 1000590 B1 | 8/2005 |
| EP | 1027013 B1 | 8/2005 |
| EP | 1078610 B1 | 8/2005 |
| EP | 1560542 A1 | 8/2005 |
| EP | 1562515 A1 | 8/2005 |
| EP | 1570809 A1 | 9/2005 |
| EP | 1576937 A2 | 9/2005 |
| EP | 0943302 B1 | 10/2005 |
| EP | 1267753 B1 | 10/2005 |

(56) References Cited

FOREIGN PATENT DOCUMENTS

| | | |
|---|---|---|
| EP | 1582178 A2 | 10/2005 |
| EP | 1582179 A2 | 10/2005 |
| EP | 1011523 B1 | 11/2005 |
| EP | 1067869 B1 | 11/2005 |
| EP | 1469797 B1 | 11/2005 |
| EP | 1589902 A1 | 11/2005 |
| EP | 1598031 A2 | 11/2005 |
| EP | 1600110 A1 | 11/2005 |
| EP | 1600121 A1 | 11/2005 |
| EP | 0786970 B1 | 12/2005 |
| EP | 1156757 B1 | 12/2005 |
| EP | 1603493 A2 | 12/2005 |
| EP | 1605871 A1 | 12/2005 |
| EP | 1021141 B1 | 1/2006 |
| EP | 1614400 A2 | 1/2006 |
| EP | 1616531 A2 | 1/2006 |
| EP | 1616536 A2 | 1/2006 |
| EP | 1041942 B1 | 6/2006 |
| EP | 1441672 A4 | 6/2006 |
| EP | 1663070 A2 | 6/2006 |
| EP | 1667614 A1 | 6/2006 |
| EP | 1494616 A4 | 7/2006 |
| EP | 1690515 A1 | 8/2006 |
| EP | 1702247 A2 | 9/2006 |
| EP | 1051204 B1 | 12/2006 |
| EP | 1734902 A1 | 12/2006 |
| EP | 1395208 B1 | 1/2007 |
| EP | 1251805 B1 | 3/2007 |
| EP | 1255510 B1 | 4/2007 |
| EP | 1499366 B1 | 7/2007 |
| EP | 1600121 B1 | 7/2007 |
| EP | 1835948 A1 | 9/2007 |
| EP | 1112042 B1 | 11/2007 |
| EP | 1251797 B1 | 11/2007 |
| EP | 1616531 B1 | 12/2007 |
| EP | 1863545 A2 | 12/2007 |
| EP | 1878407 A1 | 1/2008 |
| EP | 1886649 A2 | 2/2008 |
| EP | 1406561 A4 | 3/2008 |
| EP | 1893132 A2 | 3/2008 |
| EP | 1900343 A2 | 3/2008 |
| EP | 1901681 A1 | 3/2008 |
| EP | 1435878 B1 | 4/2008 |
| EP | 1886649 A3 | 4/2008 |
| EP | 1251804 B1 | 7/2008 |
| EP | 1605871 B1 | 7/2008 |
| EP | 1968491 A2 | 9/2008 |
| EP | 1259195 B1 | 10/2008 |
| EP | 1980220 A1 | 10/2008 |
| EP | 1994913 A2 | 11/2008 |
| EP | 1994913 A3 | 12/2008 |
| EP | 2000115 A2 | 12/2008 |
| EP | 1560542 A4 | 1/2009 |
| EP | 1408882 B1 | 2/2009 |
| EP | 1255510 B3 | 3/2009 |
| EP | 1330213 B1 | 3/2009 |
| EP | 2033593 A1 | 3/2009 |
| EP | 2047824 A1 | 4/2009 |
| EP | 2059192 A1 | 5/2009 |
| EP | 2074964 A1 | 7/2009 |
| EP | 1401359 B1 | 8/2009 |
| EP | 1968491 B1 | 7/2010 |
| EP | 1259193 B1 | 11/2010 |
| EP | 2257242 A1 | 12/2010 |
| EP | 2266503 A2 | 12/2010 |
| EP | 2266504 A2 | 12/2010 |
| EP | 1893132 B1 | 3/2011 |
| EP | 2266503 A3 | 4/2011 |
| EP | 2266504 A3 | 4/2011 |
| EP | 2059192 B1 | 7/2011 |
| EP | 1441672 B1 | 9/2011 |
| EP | 2364669 A2 | 9/2011 |
| EP | 2366363 A1 | 9/2011 |
| EP | 2387977 A1 | 11/2011 |
| EP | 1603493 B1 | 12/2011 |
| EP | 1281375 B1 | 2/2012 |
| EP | 2364669 A3 | 3/2012 |
| EP | 2047824 B1 | 5/2012 |
| EP | 2474287 A1 | 7/2012 |
| EP | 2340075 B1 | 3/2013 |
| EP | 2387977 B1 | 11/2013 |
| EP | 1551274 B1 | 12/2014 |
| EP | 2874812 A1 | 5/2015 |
| EP | 2749254 B1 | 6/2015 |
| EP | 1702247 B1 | 8/2015 |
| EP | 2926766 A1 | 10/2015 |
| EP | 1519697 B1 | 11/2015 |
| EP | 1863545 B1 | 11/2015 |
| EP | 1835948 B1 | 2/2016 |
| EP | 1734902 B1 | 6/2016 |
| EP | 3028668 A1 | 6/2016 |
| EP | 1539047 B1 | 11/2016 |
| EP | 1667614 B1 | 12/2016 |
| EP | 3181096 A1 | 6/2017 |
| EP | 2659861 B1 | 3/2019 |
| EP | 1667614 B2 | 4/2020 |
| ES | 2293734 T3 | 3/2008 |
| ES | 2313954 T3 | 3/2009 |
| ES | 2353733 T3 | 3/2011 |
| ES | 2381337 T3 | 5/2012 |
| ES | 2421438 T3 | 9/2013 |
| FI | 8311 U1 | 5/2009 |
| FR | 2432305 A1 | 2/1980 |
| FR | 2788217 A1 | 7/2000 |
| FR | 2815844 A1 | 5/2002 |
| FR | 2826863 A1 | 1/2003 |
| FR | 2828263 A1 | 2/2003 |
| FR | 2874812 A1 | 3/2006 |
| FR | 2828263 B1 | 5/2007 |
| GB | 2018950 A | 10/1979 |
| GB | 2056023 A | 3/1981 |
| GB | 2316322 A | 2/1998 |
| GB | 2316322 B | 10/1998 |
| GB | 2398214 A | 8/2004 |
| GB | 2398245 A | 8/2004 |
| GB | 2398245 B | 3/2007 |
| GB | 2433700 A | 7/2007 |
| GB | 2433700 B | 12/2007 |
| GB | 2440809 A | 2/2008 |
| GB | 2440809 B | 8/2011 |
| HK | 1053600 A1 | 7/2012 |
| JP | S5286296 A | 7/1977 |
| JP | S54137896 A | 9/1979 |
| JP | S62227352 A | 10/1987 |
| JP | S6449571 A | 2/1989 |
| JP | H0447576 B2 | 8/1992 |
| JP | H04505866 A | 10/1992 |
| JP | H06505187 A | 6/1994 |
| JP | H06343703 A | 12/1994 |
| JP | H07504091 A | 5/1995 |
| JP | H07505803 A | 6/1995 |
| JP | H07265339 A | 10/1995 |
| JP | H0833715 A | 2/1996 |
| JP | H1049571 A | 2/1998 |
| JP | H10507673 A | 7/1998 |
| JP | H11503056 A | 3/1999 |
| JP | 2001000460 A | 1/2001 |
| JP | 2001504016 A | 3/2001 |
| JP | 2001526574 A | 12/2001 |
| JP | 2002525168 A | 8/2002 |
| JP | 2002525169 A | 8/2002 |
| JP | 2002536115 A | 10/2002 |
| JP | 2003515386 A | 5/2003 |
| JP | 2003518984 A | 6/2003 |
| JP | 2003523262 A | 8/2003 |
| JP | 2003524504 A | 8/2003 |
| JP | 2004504111 A | 2/2004 |
| JP | 2004130068 A | 4/2004 |
| JP | 2004514467 A | 5/2004 |
| JP | 2004255186 A | 9/2004 |
| JP | 2004267750 A | 9/2004 |
| JP | 2004283461 A | 10/2004 |
| JP | 2005505343 A | 2/2005 |
| JP | 2005103321 A | 4/2005 |

(56) References Cited

FOREIGN PATENT DOCUMENTS

| | | |
|---|---|---|
| JP | 2005118585 A | 5/2005 |
| JP | 2007521125 A | 8/2007 |
| JP | 2007296375 A | 11/2007 |
| JP | 2007298375 A | 11/2007 |
| JP | 2007534381 A | 11/2007 |
| JP | 2007536003 A | 12/2007 |
| JP | 2008506497 A | 3/2008 |
| JP | 2008514345 A | 5/2008 |
| JP | 2008535572 A | 9/2008 |
| JP | 2008539985 A | 11/2008 |
| JP | 2008541865 A | 11/2008 |
| JP | 2009034529 A | 2/2009 |
| JP | 2009061293 A | 3/2009 |
| JP | 2009509635 A | 3/2009 |
| JP | 4246433 B2 | 4/2009 |
| JP | 2009520535 A | 5/2009 |
| JP | 2009131397 A | 6/2009 |
| JP | 4295460 B2 | 7/2009 |
| JP | 2009528905 A | 8/2009 |
| JP | 2009534157 A | 9/2009 |
| JP | 2010525896 A | 7/2010 |
| JP | 2010526609 A | 8/2010 |
| JP | 4636794 B2 | 2/2011 |
| JP | 2011509805 A | 3/2011 |
| JP | 4739223 B2 | 8/2011 |
| JP | 2012500665 A | 1/2012 |
| JP | 4904362 B2 | 3/2012 |
| JP | 4912395 B2 | 4/2012 |
| JP | 2012518446 A | 8/2012 |
| JP | 2013520260 A | 6/2013 |
| JP | 2013521884 A | 6/2013 |
| JP | 2013526388 A | 6/2013 |
| JP | 5341455 B2 | 11/2013 |
| JP | 2013540495 A | 11/2013 |
| JP | 6144009 B2 | 6/2017 |
| JP | 6449571 B2 | 1/2019 |
| PT | 1112042 E | 1/2008 |
| PT | 1259195 E | 12/2008 |
| PT | 1259193 E | 1/2011 |
| PT | 1281375 E | 3/2012 |
| PT | 1994913 E | 8/2013 |
| RU | 2149037 C1 | 5/2000 |
| SE | 7901667 L | 10/1979 |
| SU | 1271508 A1 | 11/1986 |
| SU | 1371700 A1 | 2/1988 |
| WO | WO-8402266 A1 | 6/1984 |
| WO | WO-9009102 A1 | 8/1990 |
| WO | WO-9014804 A1 | 12/1990 |
| WO | WO-9117720 A1 | 11/1991 |
| WO | WO-9203990 A1 | 3/1992 |
| WO | WO-9212690 A1 | 8/1992 |
| WO | WO-9214419 A1 | 9/1992 |
| WO | WO-9217118 A1 | 10/1992 |
| WO | WO-9301768 A1 | 2/1993 |
| WO | WO-9315693 A1 | 8/1993 |
| WO | WO-9320757 A2 | 10/1993 |
| WO | WO-9504556 A2 | 2/1995 |
| WO | WO-9504556 A3 | 4/1995 |
| WO | WO-9511055 A1 | 4/1995 |
| WO | WO-9524873 A1 | 9/1995 |
| WO | WO-9528183 A1 | 10/1995 |
| WO | WO-9528899 A1 | 11/1995 |
| WO | WO-9529640 A1 | 11/1995 |
| WO | WO-9529713 A1 | 11/1995 |
| WO | WO-9613227 A1 | 5/1996 |
| WO | WO-9614032 A1 | 5/1996 |
| WO | WO-9624306 A1 | 8/1996 |
| WO | WO-9630072 A1 | 10/1996 |
| WO | WO-9632972 A1 | 10/1996 |
| WO | WO-9635469 A1 | 11/1996 |
| WO | WO-9639962 A1 | 12/1996 |
| WO | WO-9639964 A1 | 12/1996 |
| WO | WO-9639965 A1 | 12/1996 |
| WO | WO-9640012 A1 | 12/1996 |
| WO | WO-9713463 A1 | 4/1997 |
| WO | WO-9713471 A1 | 4/1997 |
| WO | WO-9724082 A1 | 7/1997 |
| WO | WO-9727893 A1 | 8/1997 |
| WO | WO-9727897 A1 | 8/1997 |
| WO | WO-9727898 A1 | 8/1997 |
| WO | WO-9728839 A1 | 8/1997 |
| WO | WO-9732551 A1 | 9/1997 |
| WO | WO-9732615 A1 | 9/1997 |
| WO | WO-9743961 A1 | 11/1997 |
| WO | WO-9748350 A1 | 12/1997 |
| WO | WO-9803118 A1 | 1/1998 |
| WO | WO-9806356 A1 | 2/1998 |
| WO | WO-9808456 A1 | 3/1998 |
| WO | WO-9810714 A1 | 3/1998 |
| WO | WO-9811846 A1 | 3/1998 |
| WO | WO-9814137 A1 | 4/1998 |
| WO | WO-9816161 A1 | 4/1998 |
| WO | WO-9819633 A1 | 5/1998 |
| WO | WO-9824373 A1 | 6/1998 |
| WO | WO-9825533 A1 | 6/1998 |
| WO | WO-9825549 A1 | 6/1998 |
| WO | WO-9829057 A1 | 7/1998 |
| WO | WO-9836790 A1 | 8/1998 |
| WO | WO-9838916 A1 | 9/1998 |
| WO | WO-9838925 A1 | 9/1998 |
| WO | WO-9838939 A1 | 9/1998 |
| WO | WO-9838941 A1 | 9/1998 |
| WO | WO-9839038 A1 | 9/1998 |
| WO | WO-9843556 A1 | 10/1998 |
| WO | WO-9844869 A1 | 10/1998 |
| WO | WO-9846115 A2 | 10/1998 |
| WO | WO-9846119 A1 | 10/1998 |
| WO | WO-9846165 A1 | 10/1998 |
| WO | WO-9849964 A1 | 11/1998 |
| WO | WO-9850103 A1 | 11/1998 |
| WO | WO-9853759 A2 | 12/1998 |
| WO | WO-9853761 A1 | 12/1998 |
| WO | WO-9855027 A2 | 12/1998 |
| WO | WO-9855047 A1 | 12/1998 |
| WO | WO-9857590 A1 | 12/1998 |
| WO | WO-9857591 A1 | 12/1998 |
| WO | WO-9857592 A1 | 12/1998 |
| WO | WO-9857599 A2 | 12/1998 |
| WO | WO-9907296 A1 | 2/1999 |
| WO | WO-9908624 A1 | 2/1999 |
| WO | WO-9915112 A1 | 4/1999 |
| WO | WO-9915220 A1 | 4/1999 |
| WO | WO-9917671 A1 | 4/1999 |
| WO | WO-9917683 A1 | 4/1999 |
| WO | WO-9921490 A1 | 5/1999 |
| WO | WO-9921510 A1 | 5/1999 |
| WO | WO-9922655 A1 | 5/1999 |
| WO | WO-9922656 A1 | 5/1999 |
| WO | WO-9922658 A1 | 5/1999 |
| WO | WO-9925273 A1 | 5/1999 |
| WO | WO-9927985 A1 | 6/1999 |
| WO | WO-9933414 A1 | 7/1999 |
| WO | WO-9935977 A1 | 7/1999 |
| WO | WO-9935979 A1 | 7/1999 |
| WO | WO-9935980 A1 | 7/1999 |
| WO | WO-9936000 A1 | 7/1999 |
| WO | WO-9936001 A1 | 7/1999 |
| WO | WO-9937337 A2 | 7/1999 |
| WO | WO-9938459 A2 | 8/1999 |
| WO | WO-9940853 A1 | 8/1999 |
| WO | WO-9940868 A1 | 8/1999 |
| WO | WO-9940963 A1 | 8/1999 |
| WO | WO-9940964 A1 | 8/1999 |
| WO | WO-9942058 A1 | 8/1999 |
| WO | WO-9944524 A2 | 9/1999 |
| WO | WO-9944540 A2 | 9/1999 |
| WO | WO-9944542 A2 | 9/1999 |
| WO | WO-9947071 A1 | 9/1999 |
| WO | WO-9947075 A1 | 9/1999 |
| WO | WO-9948545 A1 | 9/1999 |
| WO | WO-9948549 A2 | 9/1999 |
| WO | WO-9949793 A1 | 10/1999 |
| WO | WO-9949910 A2 | 10/1999 |
| WO | WO-9951162 A1 | 10/1999 |

(56) References Cited

FOREIGN PATENT DOCUMENTS

| | | |
|---|---|---|
| WO | WO-9951165 A1 | 10/1999 |
| WO | WO-9953863 A1 | 10/1999 |
| WO | WO-9953987 A1 | 10/1999 |
| WO | WO-9955406 A1 | 11/1999 |
| WO | WO-9960941 A1 | 12/1999 |
| WO | WO-9962430 A1 | 12/1999 |
| WO | WO-9966863 A2 | 12/1999 |
| WO | WO-0002503 A1 | 1/2000 |
| WO | WO-0009059 A2 | 2/2000 |
| WO | WO-0009195 A1 | 2/2000 |
| WO | WO-0010623 A1 | 3/2000 |
| WO | WO-0012029 A1 | 3/2000 |
| WO | WO-0013722 A1 | 3/2000 |
| WO | WO-0015146 A1 | 3/2000 |
| WO | WO-0015147 A1 | 3/2000 |
| WO | WO-0015148 A1 | 3/2000 |
| WO | WO-0015149 A1 | 3/2000 |
| WO | WO-0015275 A2 | 3/2000 |
| WO | WO-0016848 A1 | 3/2000 |
| WO | WO-0018302 A2 | 4/2000 |
| WO | WO-0018323 A2 | 4/2000 |
| WO | WO-0018325 A1 | 4/2000 |
| WO | WO-0018326 A1 | 4/2000 |
| WO | WO-0018330 A1 | 4/2000 |
| WO | WO-0018331 A2 | 4/2000 |
| WO | WO-0018333 A1 | 4/2000 |
| WO | WO-0018445 A1 | 4/2000 |
| WO | WO-0018462 A2 | 4/2000 |
| WO | WO-0021436 A1 | 4/2000 |
| WO | WO-0021461 A2 | 4/2000 |
| WO | WO-0021463 A1 | 4/2000 |
| WO | WO-0021464 A1 | 4/2000 |
| WO | WO-0024449 A1 | 5/2000 |
| WO | WO-0025702 A1 | 5/2000 |
| WO | WO-0028922 A1 | 5/2000 |
| WO | WO-0028924 A2 | 5/2000 |
| WO | WO-0033725 A2 | 6/2000 |
| WO | WO-0035376 A1 | 6/2000 |
| WO | WO-0036997 A1 | 6/2000 |
| WO | WO-0041632 A1 | 7/2000 |
| WO | WO-0041633 A1 | 7/2000 |
| WO | WO-0041652 A1 | 7/2000 |
| WO | WO-0043051 A1 | 7/2000 |
| WO | WO-0044211 A1 | 7/2000 |
| WO | WO-0044308 A2 | 8/2000 |
| WO | WO-0044311 A2 | 8/2000 |
| WO | WO-0044313 A1 | 8/2000 |
| WO | WO-0044331 A1 | 8/2000 |
| WO | WO-0045711 A1 | 8/2000 |
| WO | WO-0045874 A1 | 8/2000 |
| WO | WO-0045886 A2 | 8/2000 |
| WO | WO-0047136 A1 | 8/2000 |
| WO | WO-0047139 A1 | 8/2000 |
| WO | WO-0048531 A1 | 8/2000 |
| WO | WO-0049952 A1 | 8/2000 |
| WO | WO-0049954 A2 | 8/2000 |
| WO | WO-0049956 A1 | 8/2000 |
| WO | WO-0049970 A1 | 8/2000 |
| WO | WO-0053122 A1 | 9/2000 |
| WO | WO-0053125 A1 | 9/2000 |
| WO | WO-0054660 A1 | 9/2000 |
| WO | WO-0054661 A1 | 9/2000 |
| WO | WO-0056224 A1 | 9/2000 |
| WO | WO-0056225 A1 | 9/2000 |
| WO | WO-0056387 A1 | 9/2000 |
| WO | WO-0060995 A2 | 10/2000 |
| WO | WO-0062714 A1 | 10/2000 |
| WO | WO-0066007 A1 | 11/2000 |
| WO | WO-0066009 A1 | 11/2000 |
| WO | WO-0066035 A1 | 11/2000 |
| WO | WO-0067661 A2 | 11/2000 |
| WO | WO-0069345 A1 | 11/2000 |
| WO | WO-0069367 A1 | 11/2000 |
| WO | WO-0069504 A1 | 11/2000 |
| WO | WO-0071195 A1 | 11/2000 |
| WO | WO-0078226 A1 | 12/2000 |
| WO | WO-0105331 A1 | 1/2001 |
| WO | WO-0106959 A1 | 2/2001 |
| WO | WO-0108566 A1 | 2/2001 |
| WO | WO-0108596 A1 | 2/2001 |
| WO | WO-0108602 A1 | 2/2001 |
| WO | WO-0110209 A1 | 2/2001 |
| WO | WO-0110320 A1 | 2/2001 |
| WO | WO-0110340 A1 | 2/2001 |
| WO | WO-0110341 A2 | 2/2001 |
| WO | WO-0110343 A1 | 2/2001 |
| WO | WO-0110347 A1 | 2/2001 |
| WO | WO-0110348 A1 | 2/2001 |
| WO | WO-0110349 A1 | 2/2001 |
| WO | WO-0110350 A1 | 2/2001 |
| WO | WO-0117440 A1 | 3/2001 |
| WO | WO-0117456 A1 | 3/2001 |
| WO | WO-0135864 A1 | 5/2001 |
| WO | WO-0135870 A1 | 5/2001 |
| WO | WO-0136870 A1 | 5/2001 |
| WO | WO-0139700 A1 | 6/2001 |
| WO | WO-0141679 A1 | 6/2001 |
| WO | WO-0149185 A1 | 7/2001 |
| WO | WO-0149187 A1 | 7/2001 |
| WO | WO-0149213 A2 | 7/2001 |
| WO | WO-0151104 A1 | 7/2001 |
| WO | WO-0154625 A1 | 8/2001 |
| WO | WO-0158503 A1 | 8/2001 |
| WO | WO-0162189 A1 | 8/2001 |
| WO | WO-0047139 A9 | 9/2001 |
| WO | WO-0164137 A1 | 9/2001 |
| WO | WO-0176510 A2 | 10/2001 |
| WO | WO-0182837 A2 | 11/2001 |
| WO | WO-0197715 A1 | 12/2001 |
| WO | WO-0211647 A2 | 2/2002 |
| WO | WO-0219926 A1 | 3/2002 |
| WO | WO-0222054 A1 | 3/2002 |
| WO | WO-0224118 A1 | 3/2002 |
| WO | WO-0236048 A1 | 5/2002 |
| WO | WO-0241789 A2 | 5/2002 |
| WO | WO-0243620 A1 | 6/2002 |
| WO | WO-0247575 A2 | 6/2002 |
| WO | WO-0249540 A2 | 6/2002 |
| WO | WO-02051489 A2 | 7/2002 |
| WO | WO-02056798 A2 | 7/2002 |
| WO | WO-02056955 A1 | 7/2002 |
| WO | WO-02058745 A1 | 8/2002 |
| WO | WO-02060509 A1 | 8/2002 |
| WO | WO-02067782 A2 | 9/2002 |
| WO | WO-02069842 A2 | 9/2002 |
| WO | WO-02076349 A1 | 10/2002 |
| WO | WO-02100297 A2 | 12/2002 |
| WO | WO-02100301 A1 | 12/2002 |
| WO | WO-02102286 A1 | 12/2002 |
| WO | WO-03003943 A2 | 1/2003 |
| WO | WO-03003949 A2 | 1/2003 |
| WO | WO-03007795 A2 | 1/2003 |
| WO | WO-03009785 A1 | 2/2003 |
| WO | WO-03011195 A2 | 2/2003 |
| WO | WO-03013239 A2 | 2/2003 |
| WO | WO-03015851 A1 | 2/2003 |
| WO | WO-03022183 A1 | 3/2003 |
| WO | WO-03028592 A1 | 4/2003 |
| WO | WO-03030776 A2 | 4/2003 |
| WO | WO-03032869 A1 | 4/2003 |
| WO | WO-03032870 A1 | 4/2003 |
| WO | WO-03037222 A2 | 5/2003 |
| WO | WO-03037227 A2 | 5/2003 |
| WO | WO-03047460 A2 | 6/2003 |
| WO | WO-03047468 A1 | 6/2003 |
| WO | WO-03047648 A2 | 6/2003 |
| WO | WO-03051231 A2 | 6/2003 |
| WO | WO-03063729 A2 | 8/2003 |
| WO | WO-03079928 A2 | 10/2003 |
| WO | WO-03079932 A2 | 10/2003 |
| WO | WO-03079933 A1 | 10/2003 |
| WO | WO-03088873 A1 | 10/2003 |
| WO | WO-03015851 B1 | 11/2003 |
| WO | WO-03063729 A3 | 11/2003 |

(56) References Cited

FOREIGN PATENT DOCUMENTS

| | | |
|---|---|---|
| WO | WO-03092554 A1 | 11/2003 |
| WO | WO-03094793 A1 | 11/2003 |
| WO | WO-03094797 A1 | 11/2003 |
| WO | WO-03096932 A1 | 11/2003 |
| WO | WO-03096935 A1 | 11/2003 |
| WO | WO-03101195 A1 | 12/2003 |
| WO | WO-03103949 A1 | 12/2003 |
| WO | WO-03003949 A3 | 1/2004 |
| WO | WO-2004004597 A2 | 1/2004 |
| WO | WO-2004006803 A1 | 1/2004 |
| WO | WO-2004006804 A1 | 1/2004 |
| WO | WO-2004014256 A1 | 2/2004 |
| WO | WO-2004016200 A1 | 2/2004 |
| WO | WO-2004016201 A2 | 2/2004 |
| WO | WO-2004019811 A2 | 3/2004 |
| WO | WO-2004019817 A1 | 3/2004 |
| WO | WO-2004019825 A1 | 3/2004 |
| WO | WO-2004021922 A2 | 3/2004 |
| WO | WO-2004023980 A2 | 3/2004 |
| WO | WO-2004019811 A9 | 4/2004 |
| WO | WO-2004026117 A2 | 4/2004 |
| WO | WO-2004026173 A2 | 4/2004 |
| WO | WO-2004028399 A2 | 4/2004 |
| WO | WO-2004030515 A2 | 4/2004 |
| WO | WO-2004041126 A1 | 5/2004 |
| WO | WO-2004043293 A2 | 5/2004 |
| WO | WO-2004043301 A1 | 5/2004 |
| WO | WO-2004047681 A1 | 6/2004 |
| WO | WO-2004058106 A2 | 7/2004 |
| WO | WO-2004062980 A1 | 7/2004 |
| WO | WO-2004058106 A3 | 8/2004 |
| WO | WO-2004064671 A2 | 8/2004 |
| WO | WO-2004066876 A1 | 8/2004 |
| WO | WO-2004071352 A1 | 8/2004 |
| WO | WO-2004082527 A2 | 9/2004 |
| WO | WO-2004082528 A2 | 9/2004 |
| WO | WO-2004082536 A1 | 9/2004 |
| WO | WO-2004089250 A1 | 10/2004 |
| WO | WO-2004089253 A1 | 10/2004 |
| WO | WO-2004093728 A2 | 11/2004 |
| WO | WO-2004096100 A1 | 11/2004 |
| WO | WO-2004103162 A2 | 12/2004 |
| WO | WO-2004105651 A1 | 12/2004 |
| WO | WO-2005002466 A2 | 1/2005 |
| WO | WO-2005004753 A1 | 1/2005 |
| WO | WO-2005007343 A1 | 1/2005 |
| WO | WO-2005009285 A2 | 2/2005 |
| WO | WO-2005011534 A1 | 2/2005 |
| WO | WO-2005011535 A2 | 2/2005 |
| WO | WO-2005021063 A2 | 3/2005 |
| WO | WO-2005023155 A1 | 3/2005 |
| WO | WO-2005027790 A1 | 3/2005 |
| WO | WO-2005027797 A1 | 3/2005 |
| WO | WO-2005032622 A2 | 4/2005 |
| WO | WO-2005034812 A1 | 4/2005 |
| WO | WO-2005010215 A3 | 5/2005 |
| WO | WO-2005046528 A1 | 5/2005 |
| WO | WO-2005046529 A1 | 5/2005 |
| WO | WO-2005048883 A1 | 6/2005 |
| WO | WO-2005062980 A2 | 7/2005 |
| WO | WO-2005063980 A1 | 7/2005 |
| WO | WO-2005065585 A1 | 7/2005 |
| WO | WO-2005065594 A1 | 7/2005 |
| WO | WO-2005070343 A1 | 8/2005 |
| WO | WO-2005072654 A1 | 8/2005 |
| WO | WO-2005076890 A2 | 8/2005 |
| WO | WO-2005084595 A1 | 9/2005 |
| WO | WO-2005087140 A1 | 9/2005 |
| WO | WO-2005096993 A1 | 10/2005 |
| WO | WO-2005102015 A2 | 11/2005 |
| WO | WO-2005110240 A1 | 11/2005 |
| WO | WO-2005112779 A1 | 12/2005 |
| WO | WO-2006005015 A2 | 1/2006 |
| WO | WO-2006005082 A2 | 1/2006 |
| WO | WO-2006009690 A1 | 1/2006 |
| WO | WO-2006026371 A1 | 3/2006 |
| WO | WO-2006027499 A2 | 3/2006 |
| WO | WO-2005062980 A3 | 5/2006 |
| WO | WO-2006058163 A2 | 6/2006 |
| WO | WO-2006065949 A2 | 6/2006 |
| WO | WO-2006066327 A1 | 6/2006 |
| WO | WO-2006068944 A2 | 6/2006 |
| WO | WO-2006070372 A2 | 7/2006 |
| WO | WO-2006076890 A1 | 7/2006 |
| WO | WO-2006083763 A1 | 8/2006 |
| WO | WO-2006086135 A2 | 8/2006 |
| WO | WO-2006086736 A2 | 8/2006 |
| WO | WO-2006089517 A1 | 8/2006 |
| WO | WO-2006093795 A1 | 9/2006 |
| WO | WO-2006102063 A2 | 9/2006 |
| WO | WO-2006108090 A2 | 10/2006 |
| WO | WO-2006118766 A1 | 11/2006 |
| WO | WO-2006124649 A2 | 11/2006 |
| WO | WO-2006127756 A2 | 11/2006 |
| WO | WO-2006127765 A1 | 11/2006 |
| WO | WO-2006129441 A1 | 12/2006 |
| WO | WO-2006132948 A1 | 12/2006 |
| WO | WO-2006133959 A1 | 12/2006 |
| WO | WO-2006138173 A2 | 12/2006 |
| WO | WO-2006138391 A2 | 12/2006 |
| WO | WO-2007009117 A1 | 1/2007 |
| WO | WO-2007009609 A1 | 1/2007 |
| WO | WO-2007013999 A2 | 2/2007 |
| WO | WO-2007033093 A2 | 3/2007 |
| WO | WO-2007035471 A2 | 3/2007 |
| WO | WO-2005102015 A3 | 4/2007 |
| WO | WO-2006138391 A9 | 4/2007 |
| WO | WO-2007044285 A2 | 4/2007 |
| WO | WO-2007047488 A2 | 4/2007 |
| WO | WO-2007047945 A2 | 4/2007 |
| WO | WO-2007048529 A1 | 5/2007 |
| WO | WO-2007051620 A1 | 5/2007 |
| WO | WO-2007053243 A2 | 5/2007 |
| WO | WO-2007058847 A2 | 5/2007 |
| WO | WO-2007059252 A1 | 5/2007 |
| WO | WO-2006086736 A3 | 6/2007 |
| WO | WO-2007071436 A2 | 6/2007 |
| WO | WO-2007092354 A2 | 8/2007 |
| WO | WO-2007097983 A2 | 8/2007 |
| WO | WO-2007098232 A2 | 8/2007 |
| WO | WO-2007053243 A3 | 9/2007 |
| WO | WO-2007120543 A1 | 10/2007 |
| WO | WO-2007071436 A3 | 11/2007 |
| WO | WO-2007123658 A1 | 11/2007 |
| WO | WO-2007123956 A2 | 11/2007 |
| WO | WO-2007127351 A1 | 11/2007 |
| WO | WO-2007127352 A1 | 11/2007 |
| WO | WO-2007033093 A3 | 1/2008 |
| WO | WO-2007071436 B1 | 1/2008 |
| WO | WO-2008028569 A1 | 3/2008 |
| WO | WO-2008031103 A2 | 3/2008 |
| WO | WO-2008035337 A2 | 3/2008 |
| WO | WO-2008040555 A2 | 4/2008 |
| WO | WO-2008045949 A2 | 4/2008 |
| WO | WO-2008047354 A2 | 4/2008 |
| WO | WO-2008051554 A2 | 5/2008 |
| WO | WO-2008070442 A1 | 6/2008 |
| WO | WO-2008070797 A2 | 6/2008 |
| WO | WO-2008079962 A1 | 7/2008 |
| WO | WO-2008098191 A2 | 8/2008 |
| WO | WO-2008100599 A1 | 8/2008 |
| WO | WO-2008101083 A2 | 8/2008 |
| WO | WO-2008125153 A1 | 10/2008 |
| WO | WO-2008137603 A2 | 11/2008 |
| WO | WO-2008138584 A1 | 11/2008 |
| WO | WO-2008150529 A1 | 12/2008 |
| WO | WO-2009002548 A1 | 12/2008 |
| WO | WO-2009024859 A2 | 2/2009 |
| WO | WO-2009029199 A1 | 3/2009 |
| WO | WO-2009042196 A2 | 4/2009 |
| WO | WO-2009045334 A1 | 4/2009 |
| WO | WO-2009045338 A1 | 4/2009 |
| WO | WO-2009053497 A1 | 4/2009 |
| WO | WO-2009054397 A1 | 4/2009 |

(56) References Cited

FOREIGN PATENT DOCUMENTS

| WO | WO-2007044285 A3 | 5/2009 |
|---|---|---|
| WO | WO-2009061389 A2 | 5/2009 |
| WO | WO-2009085206 A2 | 7/2009 |
| WO | WO-2009091509 A1 | 7/2009 |
| WO | WO-2009094188 A2 | 7/2009 |
| WO | WO-2009094501 A1 | 7/2009 |
| WO | WO-2009100198 A2 | 8/2009 |
| WO | WO-2009106545 A1 | 9/2009 |
| WO | WO-2009108615 A1 | 9/2009 |
| WO | WO-2009111241 A2 | 9/2009 |
| WO | WO-2009149462 A2 | 12/2009 |
| WO | WO-2009155561 A2 | 12/2009 |
| WO | WO-2010022138 A2 | 2/2010 |
| WO | WO-2010042950 A2 | 4/2010 |
| WO | WO-2010043950 A2 | 4/2010 |
| WO | WO-2010044851 A1 | 4/2010 |
| WO | WO-2010045238 A2 | 4/2010 |
| WO | WO-2010045297 A2 | 4/2010 |
| WO | WO-2010049160 A1 | 5/2010 |
| WO | WO-2010083558 A1 | 7/2010 |
| WO | WO-2010086460 A1 | 8/2010 |
| WO | WO-2010098857 A1 | 9/2010 |
| WO | WO-2010104638 A2 | 9/2010 |
| WO | WO-2010045238 A3 | 10/2010 |
| WO | WO-2010141626 A2 | 12/2010 |
| WO | WO-2011008812 A2 | 1/2011 |
| WO | WO-2011008853 A2 | 1/2011 |
| WO | WO-2011035327 A1 | 3/2011 |
| WO | WO-2011051043 A1 | 5/2011 |
| WO | WO-2011057087 A1 | 5/2011 |
| WO | WO-2011060386 A2 | 5/2011 |
| WO | WO-2011102968 A1 | 8/2011 |
| WO | WO-2011104269 A1 | 9/2011 |
| WO | WO-2011120050 A1 | 9/2011 |
| WO | WO-2011133368 A1 | 10/2011 |
| WO | WO-2011144351 A2 | 11/2011 |
| WO | WO-2011147849 A1 | 12/2011 |
| WO | WO-2012002228 A1 | 1/2012 |
| WO | WO-2012023980 A1 | 2/2012 |
| WO | WO-2012036742 A2 | 3/2012 |
| WO | WO-2012038550 A1 | 3/2012 |
| WO | WO-2012039748 A2 | 3/2012 |
| WO | WO-2012082952 A2 | 6/2012 |
| WO | WO-2012106491 A1 | 8/2012 |
| WO | WO-2012116368 A2 | 8/2012 |
| WO | WO-2012142189 A1 | 10/2012 |
| WO | WO-2012145546 A1 | 10/2012 |
| WO | WO-2012162228 A1 | 11/2012 |
| WO | WO-2013009975 A1 | 1/2013 |
| WO | WO-2013028387 A2 | 2/2013 |
| WO | WO-2013033791 A1 | 3/2013 |
| WO | WO-2013074671 A1 | 5/2013 |
| WO | WO-2013096545 A1 | 6/2013 |
| WO | WO-2013134214 A1 | 9/2013 |
| WO | WO-2014056644 A1 | 4/2014 |
| WO | WO-2014072439 A1 | 5/2014 |
| WO | WO-2014072439 A9 | 7/2014 |
| WO | WO-2015028209 A1 | 3/2015 |
| WO | WO-2016093877 A1 | 6/2016 |
| WO | WO-2016126511 A2 | 8/2016 |
| WO | WO-2016177562 A1 | 11/2016 |
| WO | WO-2021242607 A1 | 12/2021 |
| WO | WO-2023156879 A1 | 8/2023 |

OTHER PUBLICATIONS

US 8,062,356 B2, 11/2011, Salahieh et al. (withdrawn)
US 8,062,357 B2, 11/2011, Salahieh et al. (withdrawn)
US 8,075,614 B2, 12/2011, Salahieh et al. (withdrawn)
US 8,133,271 B2, 03/2012, Salahieh et al. (withdrawn)
US 8,211,170 B2, 07/2012, Paul et al. (withdrawn)
Akins C.W., et al., "Risk of Reoperative Valve Replacement for Failed Mitral and Aortic Bioprostheses," The Annals of Thoracic Surgery, 65:545-1552 (Jan. 1998). Retrieved from the Internet: URL: http://ats.ctsnetjournals.org/cgi/contenUfull/65/6/1545 (Jan. 1998).
Allen et al., "What are the characteristics of the ideal endovascular graft for abdominal aortic aneurysm exclusion?", J. Endovasc. Surg., vol. 4(2), May 1997, pp. 195-202.
Anabtawi I.N., et al., "Experimental evaluation of myocardial tunnelization as a method of myocardial revascularization," Journal of Thoracic and Cardiovascular Surgery, 58(5):638-646 (Nov. 1969).
Andersen H.R., et al., "Transluminal Implantation of Artificial Heart Valves. Description of a New Expandable Aortic Valve and Initial Results with Implantation by Catheter Technique in Closed Chest Pigs," European Heart Journal, May 1992, vol. 13, pp. 704-708.
"Aortenklappenbioprothese erfolgreich in der Entwicklung," May 16, 2003, 1 page (with English Translation).
Archie J.P., et al., "Intramyocardial Pressure: Effect of Preload on Transmural Distribution of Systolic Coronary Blood Flow," The American Journal of Cardiology, 35(6):904-911 (Jun. 1975).
Baba H., et al., "Hemodynamic effects of venous valves in aorta-coronary bypass grafts," The Journal of Thoracic and Cardiovascular Surgery, 71(5):774-778 (May 1976).
Babaliaros V., et al., "State of the Art Percutaneous Intervention for the Treatment of Valvular Heart Disease: A Review of the Current Technologies and Ongoing Research in the Field of Percutaneous Valve Replacement and Repair," Cardiology, 2007, vol. 107, pp. 87-96.
Bailey S.R., "Percutaneous Expandable Prosthetic Valves," Textbook of Interventional Cardiology, Second Edition, W.B. Saunders Company, 1994, vol. 2, pp. 1268-1276.
Block P. C., et al., "Percutaneous Approaches to Valvular Heart Disease," Current Cardiology Reports, Mar. 2005, vol. 7(2), pp. 108-113.
Blum et al., "Endoluminal Stent—Grafts for Intrarenal Abdominal Aortic Aneurysms." New Engl. J. Med., 336:13-20 (Jan. 1997).
Bonhoeffer et al., "Percutaneous Mitral Valve Dilatation with the Multi-Track System," Catheterization and Cardiovascular Interventions—Official Journal of the Society for Cardiac Angiograhy & Interventions, United States (Oct. 1999), pp. 178-183.
Bonhoeffer P., et al., "Percutaneous Insertion of the Pulmonary Valve," Journal of the American College of Cardiology, May 15, 2002, vol. 39, pp. 1664-1669.
Bonhoeffer P., et al., "Percutaneous Replacement of Pulmonary Valve in a Right-Ventricle to Pulmonary-Artery Prosthetic Conduit with Valve Dysfunction," Lancet, Oct. 2000, vol. 356, pp. 1403-1405.
Bonhoeffer P., et al., "Technique and Results of Percutaneous Mitral Valvuloplasty With the Multi-Track System," Journal of Interventional Cadiology, 13(4):263-268 (Aug. 2000).
Bonhoeffer P., et al., "Transcatheter Implantation of a Bovine Valve in Pulmonary Position: A Lamb Study," Circulation, Aug. 15, 2000, vol. 102, pp. 813-816.
Boudjemline et al., "Percutaneous Implantation of a Biological Valve in Aortic Position: Preliminary Results in a Sheep Study," European Heart Journal, vol. 22, p. 630, Abstract Only (Sep. 2001).
Boudjemline Y., et al., "Images in Cardiovascular Medicine: Percutaneous Aortic Valve Replacement in Animals," Circulation, United States, Mar. 16, 2004, vol. 109, p. e161.
Boudjemline Y., et al., "Is Percutaneous Implantation of a Bovine Venous Valve in the Inferior Vena Cava a Reliable Technique to Treat Chronic Venous Insufficiency Syndrome?," Medical Science Monitor, Poland, Mar. 2004, vol. 10(3), pp. BR61-BR66.
Boudjemline Y., et al., "Off-Pump Replacement of the Pulmonary Valve in Large Right Ventricular Outflow Tracts: A Hybrid Approach," Journal of Thoracic and Cardiovascular Surgery, United States, Apr. 2005, vol. 129(4), pp. 831-837.
Boudjemline Y., et al., "Percutaneous Aortic Valve Replacement: Will We Get There?," Heart, British Cardiac Society, England, Dec. 2001, vol. 86, pp. 705-706.
Boudjemline Y., et al., "Percutaneous Implantation of a Biological Valve in the Aorta to Treat Aortic Valve Insufficiency—A Sheep Study," Medical Science Monitor, Apr. 12, 2002, vol. 8(4), pp. BR113-BR116.

(56) References Cited

OTHER PUBLICATIONS

Boudjemline Y., et al., "Percutaneous Implantation of a Valve in the Descending Aorta in Lambs," European Heart Journal, Jul. 2002, vol. 23, pp. 1045-1049.
Boudjemline Y., et al., "Percutaneous Pulmonary Valve Replacement in a Large Right Ventricular Outflow Tract: An Experimental Study," Journal of the American College of Cardiology, Mar. 17, 2004, vol. 43(6), pp. 1082-1087.
Boudjemline Y., et al., "Percutaneous Valve Insertion: A New Approach?," Journal of Thoracic and Cardiovascular Surgery, United States, Mar. 2003, vol. 125(3), pp. 741-742.
Boudjemline Y., et al., "Stent Implantation Combined with a Valve Replacement to Treat Degenerated Right Ventricle to Pulmonary Artery Prosthetic Conduits," European Heart Journal, Sep. 2001, vol. 22, p. 355.
Boudjemline Y., et al., "Steps Toward Percutaneous Aortic Valve Replacement," Circulation, Feb. 12, 2002, vol. 105, pp. 775-778.
Boudjemline Y., et al., "The Percutaneous Implantable Heart Valve," Progress in Pediatric Cardiology, Ireland, 2001, vol. 14, pp. 89-93.
Boudjemline Y., et al., "Transcatheter Reconstruction of the Right Heart," Cardiology in the Young, England, 2003, vol. 13, pp. 308-311.
Bruce C.J., et al., "Right-sided Valve Disease Deserves Little More Respect," Circulation, 119(2):2726-2734 (May 2009).
Coats L., et al., "The Potential Impact of Percutaneous Pulmonary Valve Stent Implantation on Right Ventricular Outflow Tract Re-Intervention," European Journal of Cardio-Thoracic Surgery, England, Apr. 2005, vol. 27, pp. 536-543.
Commeau P et al., "Percutaneous Balloon Dilatation of calcific aortic Valve Stenosis: Anatomical and Haemodynamic Evaluation," British Heart Journal, 59:227-238 (Feb. 1988).
Cribier A., et al., "Percutaneous Transcatheter Implantation of an Aortic Valve Prosthesis for Calcific Aortic Stenosis: First Human Case Description," Circulation, 2002, vol. 106, pp. 3006-3008.
Cribier et al., "Early Experience with Percutaneous Transcatheter Implantation of Heart Valve Prosthesis for the Treatment of End-Stage Inoperable Patients with Calcific Aortic Stenosis", J. of Am. Coll. of Cardio, Feb. 18, 2004, 43(4), pp. 698-703.
Cribier et al., "Percutaneous Transluminal Valvuloplasty of Acquired Aortic Stenosis in Elderly Patients: An Alternative to Valve Replacement?", The Lancet, Jan. 11, 1986, pp. 63-67.
Cunanan et al., "Tissue Characterization and Calcification Potential of Commercial Bioprosthetic Heart Valves." Ann. Thorac. Surg., May 15, 2001, pp. S417-421.
Cunliffe et al., "Glutaraldehyde Inactivation of Exotic Animal Viruses in Swine Heart Tissue," Applied and Environmental Microbiology, Greenport, New York, vol. 37, No. 5, May 1979, pp. 1044-1046.
Dake et al., "Transluminal Placement of Endovascular Stent-Grafts for the Treatment of Descending Thoracic Aortic Aneurysms." New Engl. J. of Med., 331(26):1729-34 (Dec. 1994).
Dalby et al., "Non-Surgical Aortic Valve Replacement" Br. J. Cardiol., 10(6):450-452 (Nov. 2003).
Davidson M.J., et al., "Percutaneous Therapies for Valvular Heart Disease," Cardiovascular Pathology, Jan. 2006, vol. 15, pp. 123-129.
Dewey et al., "Transapical aortic valve implantation: An Animal Feasibility Study", The annals of thoracic surgery, 82:110-116 (Feb. 2006).
Dhasmana et al., "Factors Associated With Periprosthetic Leakage Following Primary Mitral Valve Replacement: With Special Consideration of Suture Technique." Annals of Thorac. Surg., (Feb. 1983), 35(2), pp. 170-178.
Dotter, "Transluminally-Placed Coilspring Endarterial Tube Grafts," Investigative Radiology, pp. 329-332 (Oct. 1969).
Emery et al., "Replacement of the Aortic Valve in Patients Under 50 Years of Age: Long-Term Follow-Up of the St. Jude Medical Prosthesis." Ann. Thorac. Surg., 75:1815-1819 (Jun. 2003).
European Search Report dated Aug. 10, 2011 for EP Application No. 06824992.9.

European Search Report for EP Patent Appl. Serial No. 12179049.7 (1257), dated Oct. 30, 2012, 4 pages.
European Search Report for EP Patent Appl. Serial No. 12179075.2 (1257), dated Oct. 29, 2012, 3 pages.
European Search Report for EP Patent Appl. Serial No. 12179141.2 (1257), dated Nov. 2, 2012, 3 pages.
European Search Report for EP Patent Appl. Serial No. 12179146.1 (1257), dated Nov. 7, 2012, 8 pages.
European Search Report for EP Patent Appl. Serial No. 12179330.1 (1257), dated Nov. 22, 2012, 3 pages.
European Search Report for EP Patent Appl. Serial No. 12179338.4 (1257), dated Nov. 2, 2012, 3 pages.
European Search Report for EP Patent Appl. Serial No. 12179339.2 (1257), dated Oct. 29, 2012, 4 pages.
European Search Report for EP Patent Appl. Serial No. 12179914.2 (1257), dated Nov. 7, 2012, 6 pages.
European Search Report for EP Patent Appl. Serial No. 13150337.7 (1257), dated Jul. 9, 2013, 3 pages.
European Search Report for EP Patent Appl. Serial No. 13183134.9 (1651), dated Nov. 19, 2013, 3 pages.
European Search Report for EP Patent Appl. Serial No. 14159630.4 (1651), dated May 22, 2014, 3 pages.
European Search Report for EP Patent Appl. Serial No. 14161991.6 (1651), dated Jun. 3, 2014, 3 pages.
European Search Report for EP Patent Appl. Serial No. 15167832.3 (1651), dated Jul. 23, 2015, 3 pages.
European Search Report for EP Patent Appl. Serial No. 15167847.1 (1651), dated Jul. 23, 2015, 3 pages.
European Search Report for EP Patent Appl. Serial No. 17196833.2, dated Mar. 6, 2018, 4 pages.
European Search Report for EP Patent Appl. Serial No. 18164490.7, dated Sep. 17, 2018 5 pages.
European Search Report from EP Patent Office for EP Application No. 15177718.2, dated Jan. 18, 2016, 4 pages.
European Search Report from EP Patent Office for EP Application No. 15177731.5, dated Apr. 14, 2016, 4 pages.
European Search Report from EP Patent Office for EP Application No. 16151726.3, dated Feb. 25, 2016, 4 pages.
Examination Report dated Mar. 3, 2014 for corresponding Australian Patent Application No. 2011253586, 3 pages.
Examination Report dated Mar. 28, 2014, for European Patent Application No. 08806901.8, 5 pages.
Examination Report for Australian Application No. 2009200985, dated Mar. 4, 2010, 3 pages.
Examination Report for European Application No. 06841127.1, mailed Feb. 6, 2009, 4 pages.
Examination Report for European Application No. 07818037.9, dated Aug. 11, 2009, 4 pages.
Examiner's First Report on AU Patent Application No. 2011202667, dated May 17, 2012, 3 pages.
Extended European Search Report dated Apr. 11, 2008 in EP Patent Appl. Serial No. 081630410, 5 pages.
Extended EP Search Report dated Sep. 24, 2020 in EP Patent Appl. Serial No. 20165841.6 (JVT-0280).
Extended European Search Report for Application No. 10183946. 2.4-2320 dated Feb. 14, 2012, 7 pages.
Extended European Search Report dated Aug. 9, 2018 in EP Patent Appl. Serial No. 18158901.1 (1113).
Extended European Search Report dated Jun. 12, 2018 in EP Patent Appl. Serial No. 17209326.2 (1113).
Extended European Search Report dated May 16, 2012 in EP Patent Appl. Serial No. 11178135.7 (1257).
Extended European Search Report for Application No. 11178076. 3-1257 dated Feb. 29, 2012, 5 pages.
Extended European Search Report from EP Patent Office for EP Application No. 17162616.1, dated Jul. 27, 2017, 7 pages.
Extended European Search Report dated Apr. 9, 2014 in EP Patent Appl. Serial No. 14164683.6.
Extended European Search Report dated May 9, 2013 in EP Patent Appl. Serial No. 130178309.4,4 pages.
Extended European Search Report dated Aug. 19, 2011 in EP Patent Appl. Serial No. 07827132.7.

(56) References Cited

OTHER PUBLICATIONS

Extended European Search Report dated Feb. 27, 2017 in EP Patent Appl. Serial No. 16186773,6 pages.
Extended European Search Report dated Sep. 29, 2014 in EP Patent Appl. Serical No. 14164680, 5 pages.
Extended European Search Report for Application No. 07116242.4-2310 dated Mar. 31, 2008, 10 pages.
Extended European Search Report for Application No. 09154935.2, dated May 29, 2009, 7 pages.
Extended European Search Report for Application No. 10012198.7 dated Mar. 23, 2011, 7 pages.
Extended European Search Report for Application No. 10168525.3-1257 dated Feb. 3, 2011, 13 pages.
Extended European Search Report for Application No. 11153142.2-1257 dated Aug. 3, 2011, 10 pages.
Extended European Search Report for Application No. 11165093.3-1257 dated Aug. 30, 2011, 6 pages.
Extended European Search Report for Application No. 11178073.0-1257 dated Oct. 14, 2011, 5 pages.
Extended European Search Report for Application No. 11178145.6-1257 dated Feb. 29, 2012, 5 pages.
Extended European Search Report for Application No. 13188858.8-1651 dated Jan. 13, 2014, 6 pages.
Extended European Search Report for Application No. 19195062 dated Jan. 2, 2020, 7 pages.
Extended European Search Report for EP Patent Appl. Serial No. 06827630.2 dated Jun. 7, 2010, 5 pages.
Extended European Search Report for EP Patent Appl. Serial No. 07110318.8, dated May 29, 2008, 10 pages.
Extended European Search Report for EP Patent Appl. Serial No. 10163478.0, dated Mar. 22, 2011, 9 pages.
Extended European Search Report for EP Patent Appl. Serial No. 10184842.2, dated Mar. 23, 2011, 7 pages.
Extended European Search Report for EP Patent Appl. Serial No. 11162971.3, dated Jun. 30, 2011, 5 pages.
Extended European Search Report for EP Patent Appl. Serial No. 13163918.9, dated Jul. 24, 2013, 8 pages.
Extended European Search Report for EP Patent Appl. Serial No. 14179639.1, dated Mar. 9, 2015, 7 pages.
Extended European Search Report for EP Patent Appl. Serial No. 16201320.5, dated May 19, 2017, 6 pages.
Extended European Search Report for EP Patent Appl. Serial No. 18200191.7, dated May 6, 2019, 8 pages.
Ferrari, "Entwicklung eines Verfahrens zum transvaskularen Aortenklappenersatz," Habilitationsschrift, Medizinische Fakultat der Friedrich-Schiller-Universitat Jena, Sep. 2003, pp. 1-159. (With English Translation).
Ferrari, "Entwicklung eines Verfahrens zum transvaskularen Aortenklappenersatz," Habilitationsschrift, Medizinische Fakultät der Friedrich-Schiller-Universität Jena, Sep. 2003, pp. 49-52. (With English Translation).
Ferrari M.W., "Transarterial Aortic Valve Replacement with a Self Expanding Stent in Pigs," Heart, vol. 90, No. 11, doi:10.1136/hrt.2003.028951, ISSN 1355-6037, XP055137208, Nov. 2004, pp. 1326-1331.
Filsoufi F., et al., "Long-term Outcomes of Tricuspid Valve Replacement in the Current Era," Ann. Thorac. Surg., 8(3):845-850 (Sep. 2005).
Fluency Vascular Stent Graft Instructions for Use, May 2014, 20 pages.
Greeenberg, "Abdominal Aortic Endografting: Fixation and Sealing." J. Am. Coll. Surg., 194(1):S79-S87 (Jan. 2002).
Grossi A.E. et al., "Impact of Minimally Invasive Valvular Heart Surgery: A Case-Control Study", Ann. Thorac. Surg., 71:807-810 (Mar. 2001).
Gummert J.F. et al., Cardiac Surgery in Germany During 2006: A Report on Behalf of the German Society for Thoracic and Cardio-vascular Surgery, Thorac. Cardiov. Surg., vol. 55, (Sep. 2007), pp. 343-350.
Gummert J.F. et al., "Cardiac Surgery in Germany During 2007: A Report on Behalf of the German Society for Thoracic and Cardio-vascular Surgery," Thorac. Cardiov. Surg., vol. 56, (Sep. 2008), pp. 328-336.
Hanzel G.S., et al., "Complications of Percutaneous Aortic Valve Replacement: Experience with the Cribier-Edwards TM Percutaneous Heart Valve," EuroIntervention Supplements, 2006, vol. 1(A), pp. A3-A8.
Heinrich R.S., et al., "Experimental analysis of fluid mechanical energy losses in aortic valve stenosis: importance of pressure recovery", Ann Biomed Eng., Nov.-Dec. 1996, vol. 24(6), pp. 685-694.
Hijazi Z.M., "Transcatheter Valve Replacement: A New Era of Percutaneous Cardiac Intervention Begins", J. of Am. College of Cardio., Nov. 6, 2004, vol. 43, No. 6, pp. 1088-1089.
Hourihan M., et al., "Transcatheter Umbrella Closure of Valvular and Paravalvular Leaks", JACC, Boston, Massachusetts, 20(6):1371-1377 (Nov. 1992).
Huber C.H., et al., "Direct Access Valve Replacement (DAVR)—are we entering a new era in cardiac surgery?" European Journal of Cardio-thoracic Surgery, vol. 29, Jan. 19, 2006, pp. 380-385.
Huber C.H., et al., "Direct-Access Valve Replacement: A Novel Approach for Off-Pump Valve Implantation Using Valved Stents," Journal of the American College of Cardiology, Jul. 19, 2005, vol. 46(2), pp. 366-370.
Huber C.H., et al., "Do Valved Stents Compromise Coronary Flow?," European Journal of Cardio-thoracic Surgery, Jan. 23, 2004, vol. 25, pp. 754-759.
Ing F., "Stents: What's Available to the Pediatric Interventional Cardiologist?" Catheterization and Cardiovascular Interventions, 57:374-386 (Jun. 2002).
International Search Report dated Dec. 29, 2003 in Intl PCT Patent Appl. U.S. Appl. No. PCT/DE2003/002669.
International Search Report and Written Opinion for PCT Application No. PCT/EP2009/052230 dated Jun. 29, 2009, 12 pages.
International Search Report and Written Opinion for PCT Application No. PCT/EP2010/052429 dated Jun. 14, 2010, 12 pages.
International Search Report and Written Opinion for PCT Application No. PCT/EP2011/002524 dated Apr. 23, 2012, 15 pages.
International Search Report and Written Opinion for PCT Application No. PCT/EP2011/052674 dated Jul. 5, 2011, 12 pages.
International Search Report for PCT Application No. PCT/US1999/020736 dated Jan. 28, 2000, 3 pages.
International Search Report and Written Opinion for PCT Application No. PCT/EP2009/050762 dated Jun. 23, 2009, 12 pages.
International Search Report & Written Opinion mailed Jul. 18, 2016 for PCT Patent Appl No. PCT/EP2016/059839, 10 pages.
International Search Report and Written Opinion for Appl. No. PCT/EP2016/055783, mailed on May 30, 2016, 15 pages.
International Search Report and Written Opinion for Application No. PCT/EP2013/057431 dated Jul. 26, 2013, 9 pages.
International Search Report and Written Opinion for Application No. PCT/IB2018/050438 mailed Apr. 12, 2018, 11 pages.
International Search Report and Written Opinion for International Application No. PCT/EP2010/063306, dated Nov. 17, 2010, 9 pages.
International Search Report and Written Opinion for PCT Application No. PCT/EP2006/010519 dated Mar. 1, 2007, 13 pages.
International Search Report and Written Opinion for PCT Application No. PCT/US06/36286 dated Jul. 9, 2007, 4 pages.
International Search Report and Written Opinion for PCT Application No. PCT/US2004/041513 dated Jun. 10, 2005, 4 pages.
International Search Report and Written Opinion for PCT Application No. PCT/US2004/043607 dated Mar. 20, 2006, 4 pages.
International Search Report and Written Opinion for PCT Application No. PCT/US2005/020947 dated Oct. 6, 2005, 5 pages.
International Search Report and Written Opinion for PCT Application No. PCT/US2006/038352 dated May 19, 2008, 4 pages.
International Search Report and Written Opinion for PCT Application No. PCT/US2006/043484 dated Jun. 25, 2008, 4 pages.
International Search Report and Written Opinion for PCT Application No. PCT/US2007/003992 dated Jan. 10, 2008, 5 pages.

(56) References Cited

OTHER PUBLICATIONS

International Search Report and Written Opinion for PCT Application No. PCT/US2007/02970 dated Oct. 19, 2007, 7 pages.
International Search Report and Written Opinion for PCT Application No. PCT/US2009/060531 dated May 13, 2010, 6 pages.
International Search Report and Written Opinion for PCT/DE2006/000056 dated Jun. 7, 2006, 11 pages.
International Search Report and Written Opinion for PCT/EP2007/061117 dated May 20, 2008, 16 pages.
International Search Report and Written Opinion for PCT/EP2008/003803 dated Aug. 20, 2008, 10 pages.
International Search Report and Written Opinion for PCT/EP2009/055958 dated Oct. 21, 2009, 8 pages.
International Search Report and Written Opinion for PCT/EP2010/056558 dated Oct. 7, 2010, 14 pages.
International Search Report and Written Opinion for PCT/EP2012/067617 dated Dec. 19, 2012, 10 pages.
International Search Report and Written Opinion for PCT/IL2007/001149 dated May 1, 2008, 4 pages.
International Search Report and Written Opinion for PCT/US2011/027730 dated May 25, 2011, 9 pages.
International Search Report and Written Opinion of the International Search Authority for International Application No. PCT/EP2008/064558, date of completion of report is Mar. 18, 2009, 14 pages.
International Search Report dated Jan. 28, 2008 in Int'l PCT Application Serial No. PCT/EP2007/007413, 4 pages.
International Search Report dated Jul. 7, 2015 in Int'l PCT Application Serial No. PCT/EP2014/065817, 6 pages.
International Search Report dated Nov. 3, 2011 in Int'l PCT Application Serial No. PCT/EP2011/058506, 4 pages.
International Search Report dated Dec. 18, 2012 in Int'l PCT Patent Application Serial No. PCT/EP2012/067714, 3 pages.
International Search Report for Application No. PCT/DE2001/000837, dated Aug. 7, 2001, 4 pages.
International Search Report for Application No. PCT/EP2006/012455, mailed Sep. 27, 2007, 5 pages.
International Search Report for Application No. PCT/EP2010/057798, dated Sep. 12, 2010, 6 pages.
International Search Report for Application No. PCT/EP2011/066677, dated Feb. 17, 2012, 7 pages.
International Search Report for Application No. PCT/EP2012/067617 mailed Dec. 19, 2012, 3 pages.
International Search Report for Application No. PCT/EP2013/073318, dated Apr. 17, 2014, 5 pages.
International Search Report for Application No. PCT/EP2016/055783, mailed on May 30, 2016, 5 pages.
International Search Report for Application No. PCT/EP2016/058532, dated Jul. 11, 2016, 4 pages.
International Search Report for Application No. PCT/IB2008/002180, dated Apr. 15, 2009, 7 pages.
International Search Report for Application No. PCT/IB2018/050438 mailed Apr. 12, 2018, 3 pages.
International Search Report for PCT/DE2001/000836 dated Jun. 13, 2001, 6 pages.
International Search Report for PCT/EP2006/010023 dated Mar. 30, 2007, 6 pages.
International Search Report for PCT/IB2017/052718, dated Sep. 5, 2017, 4 pages.
Kato et al., "Traumatic Thoracic Aortic Aneurysm: Treatment with Endovascular Stent-Grafts." Radiol., 205:657-662 (Dec. 1997).
Khambadkone S., et al., "Nonsurgical Pulmonary Valve Replacement: Why, When, and How?," Catheterization and Cardiovascular Interventions, United States, Jul. 2004, vol. 62, pp. 401-408.
Khambadkone S., et al., "Percutaneous Implantation of Pulmonary Valves," Expert Review of Cardiovascular Therapy (England), Nov. 2003, vol. 1(4), pp. 541-548.
Khambadkone S., et al., "Percutaneous Pulmonary Valve Implantation: Early and Medium Term Results," Circulation, Oct. 28, 2003, vol. 108(17), page IV-375.
Klein A.L., et al., "Age-related Prevalence of Valvular Regurgitation in Normal Subjects: A Comprehensive Color Flow Examination of 118 Volunteers," Journal of the American Society of Echocardiography, vol. 3, No. 1, (Jan. 1990), pp. 54-63.
Knudsen et al., "Catheter-implanted prosthetic heart valves", Intl J. of Art. Organs, 16(5): 253-262, May 1993.
Kort et al., "Minimally Invasive Aortic Valve Replacement: Echocardiographic and Clinical Results." Am. Heart J., Sep. 2001, vol. 142(3), pp. 476-481.
Kuzela L., et al., "Experimental evaluation of direct transventricular revascularization," Journal of Thoracic and Cardiovascular Surgery, 57(6):770-773 (Jun. 1969).
Laborde et al., "Percutaneous Implantation of the Corevalve Aortic Valve Prosthesis for Patients Presenting High Risk for Surgical Valve Replacement," EuroIntervention, 1(4):472-474 (Feb. 2006).
Lawrence et al., "Percutaneous Endovascular Graft: Experimental Evaluation", Radiology, May 1987, vol. 163(2), pp. 357-360.
Levi et al., "Future of Interventional Cardiology in Pediactrics." Current Opinion in Cardiol., 18:79-90 (Mar. 2003).
Levy, "Mycobacterium chelonei Infection of Porcine Heart Valves." The New England Journal of Medicine, Washington DC, 297(12), Sep. 22, 1977, pp. 667-668.
Lichtenstein et al., "Transapical Transcatheter Aortic Valve Implantation in Humans: Initial Clinical Experience", circulation, American Heart Association vol. 114, Jul. 31, 2006, pp. 591-596.
Lichtenstein, S.V., "Closed heart surgery: Back to the future" The Journal of Thoracic and Cardiovascular Surgery, vol. 131(5), May 2006, pp. 941-943.
Liu et al., "Effect of Fiber Orientation on the Stress Distribution within a Leaflet of a Polymer Composite Heart Valve in be Closed Position", Journal of Biomechanics, 4:1099-1106 (Jan. 2007).
Lonescu et al., "Prevalence and Clinical Significance of Incidental Paraprosthetic Valvar Regurgitation: A prospective study using transesophageal echocardiography." Heart, 89:1316-21 (Oct. 2003).
Love S.C. et al., The Autogenous Tissue Heart Valve: Current Status, Journal of Cardiac Surgery, , Mar. 1991, vol. 6(4), pp. 499-507.
Lutter G., et al., "Percutaneous Aortic Valve Replacement: An Experimental Study. I. Studies on Implantation," Journal of Thoracic and Cardiovascular Surgery, Apr. 2002, vol. 123(4), pp. 768-776.
Lutter G., et al., "Percutaneous Valve Replacement: Current State and Future Prospects," Annals of Thoracic Surgery, Netherlands, Dec. 2004, vol. 78, pp. 2199-2206.
Ma L., et al., "Double-Crowned Valved Stents for Off-Pump Mitral Valve Replacement," European Journal of Cardio-Thoracic Surgery, Jun. 13, 2005, vol. 28(2), pp. 194-199.
Mack, M.J., "Minimally invasive cardiac surgery", Surg Endosc, 20:S488-S492 (Mar. 2006).
Magovern et al., "Twenty-five-Year Review of the Magovern-Cromie Sutureless Aortic Valve", Ann. Thorac. Surg., 48:S33-S334 (Jan. 1989).
Maraj et al., Evaluation of Hemolysis in Patients with Prosthetic Heart Valves, Clin. Cardiol. 21:387-392 (Jun. 1998).
Marcus Rh et al., "Assessment of small-diameter aortic mechanical prostheses: physiological relevance of the Doppler gradient, utility of flow augmentation, and limitations of orifice area estimation," Circulation, 98(9):866-872 (Sep. 1998).
McKay G. R. et al., "The Mansfield Scientific Aortic Valvuloplasty Registry: Overview of Acute Hemodynamic Results and Procedural Complications." J. Am. Coll. Cardiol., 17(2):485-491 (Feb. 1991).
Mills N.L., et al., "Valvulotomy of valves in the saphenous vein graft before coronary artery bypass," The Journal of Thoracic and Cardiovascular Surgery, 71(6):878-879 (Jun. 1976).
Mirich et al., "Percutaneously Placed Endovascular Grafts for Aortic Aneurysms: Feasibility Study", Radiology, 170:1033-1037 (Mar. 1989).
Moazami N et al. "Transluminal Aortic Valve Placement: a Fesibility Study with a Newly Designed Collapsible Aortic Valve", ASAIO Journal, vol. 42, No. 2, Mar.-Apr. 1996.
Moulopoulos et al., "Catheter-Mounted Aortic Valves," Annals of Thoracic Surg., vol. 11, No. 5, May 1971, pp. 423-430.

(56) References Cited

OTHER PUBLICATIONS

Munro I., et al., "The possibility of myocardial revascularization by creation of a left ventriculocoronary artery fistula," The Journal of Thoracic and Cardiovascular Surgery, 58(1):25-32 (Jul. 1969).
Nath J., et al., Impact of Tricuspid Regurgitation on Long-term Survival, Journal of the American College of Cardiology, 43(3):405-406 (Feb. 2004).
Nietlispach F., et al., "Current Balloon-Expandable Transcatheter Heart Valve and Delivery Systems", Catheterization and Cardiovascular Interventions, 75:295-300 (Sep. 2009).
Palacios I.F., "Percutaneous Valve Replacement and Repair: Fiction or Reality?," Journal of American College of Cardiology, Oct. 2004, vol. 44(8), pp. 1662-1663.
Palmaz J.C., et al., "Expandable Intrahepatic Portacaval Shunt Stents: Early Experience in the Dog," American Journal of Roentgenology, 145 (4):821-825 (Oct. 1985).
Palmaz J.C., et al., "Expandable Intrahepatic Portacaval Shunt Stents in Dogs with Chronic Portal Hypertension," American Journal of Roentgenology, 147(6):1251-1254 (Dec. 1986).
Paniagua et al., "Percutaneous Heart Valve in the Chronic in Vitro Testing Model." Circulation, Sep. 17, 2002, vol. 106: e51-e52.
Parodi J.C., et al., "Transfemoral Intraluminal Graft Implantation for Abdominal Aortic Aneurysms", Ann. Vasc. Surg., 5(6):491-499 (Nov. 1991).
Partial European Search Report dated Feb. 28, 2012 in EP Patent Appl. Serial No. 11178135.7 (1257).
Partial European Search Report for Application No. 10168525.3-1269 dated Sep. 20, 2010, 5 pages.
Partial European Search Report for Application No. 07116242.4-2310 dated Jan. 14, 2008, 5 pages.
Partial European Search Report for Application No. 11153142.2-1257 dated Apr. 4, 2011, 5 pages.
Partial European Search Report for EP Patent Appl. Serial No. 07110318.8, dated Mar. 10, 2008, 6 pages.
Partial European Search Report for EP Patent Appl. Serial No. 10163478.0, dated Nov. 2, 2010, 6 pages.
Partial International Search Report for International Application No. PCT/EP2014/055044, filed Mar. 13, 2014, 7 pages.
Paul et al., U.S. Appl. No. 12/578,463 entitled "Medical Devices and Delivery Systems for Delivering Medical Devices," filed Oct. 13, 2009, 79 pages.
Pavcnik D., et al., "Aortic and Venous Valve for Percutaneous Insertion," Minimally Invasive Therapy & Allied Technologies, Jan. 2000, vol. 9(3/4), pp. 287-292.
Pavcnik D., et al., "Development and Initial Experimental Evaluation of a Prosthetic Aortic Valve for Transcatheter Placement." Radiology, 183:151-154 (Apr. 1992).
Pavcnik et al., "Percutaneous Bioprosthetic Venous Valve: A Long-term Study in Sheep," Jounal of Vascular Surg., vol. 35, No. 3, Mar. 2002, pp. 598-603.
Pawelec-Wojtalk M., "Closure of left ventricle perforation with the use of muscular VSD occluder," European Journal of Cardia-Thoracic Surgery, 27(4):714-716 (Apr. 2005).
Pelton A.R., et al., "Medical Uses of Nitinol," Materials Science Forum, Jan. 2000, vol. 327-328, pp. 63-70.
Phillips et al., "A Temporary Catheter-Tip Aortic Valve: Hemodynamic Effects on Experimental Acute Aortic Insufficiency", Annals of Thoracic Surg., Feb. 1976, 21(2), pp. 134-136.
Phillips S.J., et al., "Improvement in Forward Coronary Blood Flow by Using a Reversed Saphenous Vein with a Competent Valve," The Annals of Thoracic Surgery, vol. 21 (1), Jan. 1976, pp. 12-15.
Preliminary Search Report (Rapport De Recherche Preliminaire) dated Jul. 8, 2002 in French Patent Application No. 0110444 (2 pages).
Raillat et al., "Treatment of Iliac Artery Stenosis with the Wallstent Endoprosthesis." AJR, Mar. 1990, vol. 154(3), pp. 613-616.
Remadi et al., "Preliminary results of 130 aortic valve replacements with a new mechanical bileaflet prosthesis: The Edwards MIRA valve," Interactive Cardiovasc. and Thorac. Surg., 2:80-83 (Mar. 2003).
Rogers J.H., et al., "The Tricuspid Valve: Current Perspective and Evolving Management of Tricuspid Regurgitation," Circulation, 119(20):2718-2725 (May 2009).
Ruiz C.E., "Transcatheter Aortic Valve Implantation and Mitral Valve Repair: State of the Art," Pediatric Cardiology, Jun. 2005, vol. 26(3), pp. 289-294.
Saliba Z., et al., "Treatment of Obstructions of Prosthetic Conduits by Percutaneous Implantation of Stents," Archives Des Maladies Du Coeur Et Des Vaisseaux, May 1999, pp. 591-596.
Schurink et al., "Stent Attachment Site—related Endoleakage after Stent Graft Treatment: An in vitro study of the effects of graft size, stent type, and atherosclerotic wall changes", J. Vasc. Surg., vol. 30(4), Oct. 1999, pp. 658-667.
Search Report dated Oct. 15, 2003 from the European Patent Office for European Patent Application No. EP 02291953.4, 2 pages.
Search Report from the European Patent Office for European Patent Application No. EP 02291954.4, 4 pages.
Sochman et al., "Percutaneous Transcatheter Aortic Disc Valve Prosthesis Implantation: A Feasibility Study." Cardiovasc. Intervent. Radiol., Sep. 2000, 23: 384-388.
Stanley et al., "Evaluation of Patient Selection Guidelines for Endoluminal AAA Repair With the Zenith Stent Graft: The Australasian Experience." J. Endovasc. Ther., 8:457-464 (Oct. 2001).
Stassano P., et al., "Mid-term Results of the Valve-on-Valve Technique for Bioprosthetic Failure," European Journal of Cardiothoracic Surgery, Oct. 2000, vol. 18, pp. 453-457.
Stein D.P., et al., "Turbulent blood flow in the ascending aorta of humans with normal and diseased aortic valves", Circulation Research by American Heart Association, 39:58-65 (Jul. 1976).
Steinhoff et al., "Tissue Engineering of Pulmonary Heart Valves on Allogenic Acellular Matrix Conduits." Circulation102 [suppl. III], pp. III-50-III-55 (Nov. 2000).
Supplemental Search Report from EP Patent Office for EP Application No. 04813777.2, dated Aug. 19, 2011.
Supplemental Search Report from EP Patent Office for EP Application No. 04815634.3, dated Aug. 19, 2011.
Supplemental Search Report from EP Patent Office for EP Application No. 05758878.2, dated Oct. 24, 2011.
Supplementary European Search Report dated Jan. 2, 2012 in EP Patent Appl. Serial No. 09820051.2.
Thompson et al., "Endoluminal stent grafting of the thoracic aorta: Initial experience with the Gore Excluder," Journal of Vascular Surgery, Jun. 2002, pp. 1163-1170.
Topol, Eric., Textbook of Interventional Cardiology, 4th Ed; Chapter 24: "Endovascular Options for Peripheral Arterial Occlusive and Aneurysmal Disease," Saunders, pp. 499-503, 949-953 (Dec. 2003).
Triennial Review of the National Nanotechnology Initiative: "A Matter of Size", The National Academies Press, Washington DC, V-13, Retrieved from the Internet: URL: http://www.nap.edu/catalog/11752/a-matter-of-size-triennial-review-of-the-national-nanotechnology, 200 pages (Mar. 2006) (Parts 1-5).
Vahanian et al., "Percutaneous Approaches to Valvular Disease", Circulation, Apr. 6, 2004, 109: 1572-1579.
Van Herwerden et al., "Percutaneous Valve Implantation: Back to the Future?", Euro. Heart J., Sep. 2002, 23(18): 1415-1416.
Walther et al., "Transapical approach for sutureless stent-fixed aortic valve implantation: experimental results", European Journal of Cardio-thoracic Surgery 29, 703-708 (May 2006).
Webb J.G., et al., "Percutaneous Aortic Valve Implantation Retrograde from the Femoral Artery," Circulation, American Heart Association, Feb. 14, 2006, vol. 113, pp. 842-850.
Weerasinghe A., et al., "First Redo Heart Valve Replacement: A 10-Year Analysis," Circulation, 99(5):655-658 (Feb. 1999).
Weyman Ab et al., "Aortic Stenosis: Physics and Physiology—What Do the Numbers Really Mean?", Rev Cardiovasc Med., 6(1):23-32 (Jan. 2005).
White et al., "Endoleak as a Complication of Endoluminal Grafting of Abdominal Aortic Aneurysms: Classification, Incidence, Diagnosis, and Management," J. Endovasc. Surg., 4:152-168 (May 1997).
Written Opinion dated Mar. 30, 2007 in Int'l PCT Application Serial No. PCT/EP2006/010023, 10 Pages.

(56) References Cited

OTHER PUBLICATIONS

Written Opinion dated Sep. 27, 2007 in Int'l Application No. PCT/EP2006/012455, 11 pages.
Written Opinion for Application No. PCT/EP2007/007413, mailed Jan. 28, 2008, 5 pages.
Written Opinion for Application No. PCT/EP2011/058506, mailed Nov. 3, 2011, 5 pages.
Written Opinion for Application No. PCT/EP2014/065817, mailed Jan. 7, 2015, 7 pages.
Written Opinion for PCT/EP2012/067714 dated Dec. 18, 2012, 5 Pages.
Yonga G.O., et al., "Percutaneous Transvenous Mitral Commissurotomy in Juvenile Mitral Stenosis", East African Medical Journal, 80(4):172-174 (Apr. 2003).
Yoshioka et al., "Self-Expanding Endovascular Graft: An Experimental Study in Dogs." AJR 151, Oct. 1988, pp. 673-676.
Zhou et al., "Self-expandable Valved Stent of Large Size: Off-Bypass Implantation in Pulmonary Position", Eur. J. Cardiothorac, Aug. 2003, 24: 212-216.
International Search Report & Written Opinion dated Feb. 20, 2024 in Int'l PCT Patent Appl. Serial No. PCT/IB2023/037029 (401001).
International Search Report & Written Report Opinion dated Apr. 17, 2024 in Int'l PCT Patent Appl. Serial No. PCT/US2023/080979 (411001).

STENT FOR THE POSITIONING AND ANCHORING OF A VALVULAR PROSTHESIS IN AN IMPLANTATION SITE IN THE HEART OF A PATIENT

CROSS-REFERENCE TO RELATED APPLICATIONS

This application is a continuation of U.S. patent application Ser. No. 16/741,956, filed Jan. 14, 2020, now U.S. Pat. No. 11,564,794, which is a continuation of U.S. patent application Ser. No. 15/850,165, filed Dec. 21, 2017, now U.S. Pat. No. 10,575,947, which is a continuation of U.S. patent application Ser. No. 14/790,909, filed on May 12, 2015, now U.S. Pat. No. 9,877,828, which is a continuation of U.S. patent application Ser. No. 12/071,814, filed Feb. 26, 2008, now U.S. Pat. No. 9,044,318, the entire contents of each of which are incorporated herein by reference.

The present invention relates to a stent for the positioning and anchoring of a valvular prosthesis in an implantation site in the heart of a patient. Specifically, the present invention relates to an expandable stent for an endoprosthesis used in the treatment of a stenosis (narrowing) of a cardiac valve and/or a cardiac valve insufficiency.

The expression "narrowing (stenosis) of a cardiac valve and/or cardiac valve insufficiency" is intended to include a functional defect of one or more cardiac valves, which is either genetic or has developed. A cardiac defect of this type might affect each of the four heart valves, although the valves in the left ventricle (aortal and mitral valves) are affected much more often than the right-sided part of the heart (pulmonary and tricuspid valves). The functional defect can result in narrowing (stenosis), inability to close (insufficiency) or a combination of the two (combined vitium). This invention relates to an expandable stent for inserting a heart valve stent in a patient's body for treating such a heart valve defect.

In the current treatment of severe narrowing of a cardiac valve and/or cardiac valve insufficiency, the narrowed or diseased cardiac valve is replaced with a valvular prosthesis. Biological or mechanical valves models, which are typically surgically sewn into the cardiac valve bed through an opening in the chest after removal of the diseased cardiac valve, are used for this purpose. This operation necessitates the use of a heart-lung machine to maintain the patient's circulation during the procedure and cardiac arrest is induced during implantation of the prosthesis. This is a risky surgical procedure with associated dangers for the patient, as well as a long post-operative treatment and recovery phase. Such an operation can often not be considered with justifiable risk in the case of polypathic patients.

Minimally-invasive forms of treatment have been developed recently which are characterized by allowing the procedure to be performed under local anesthesia. One approach provides for the use of a catheter system to implant a self-expandable stent to which is connected a collapsible valvular prosthesis. Such a self-expandable endoprosthesis can be guided via a catheter system to the implantation site within the heart through an inguinal artery or vein. After reaching the implantation site, the stent can then be unfolded.

To this end, it is known that a stent may be comprised of, for example, a plurality of self-expanding longitudinal stent segments, the segments being articulated relative one another. In order to anchor the stent securely in position the an appropriate blood vessel close to the heart, anchoring barbs are frequently used to engage with the vascular wall.

An expandable stent for the fastening and anchoring of a valvular prosthesis is known from printed publication DE 10 010 074 A1, whereby the stent is essentially formed of wire-shaped, interconnected segments. DE 10 010 074 A1 proposes a stent for fastening and anchoring a valvular prosthesis, the stent having different arched elements which assume the function of fastening and supporting the valvular prosthesis at the site of implantation. Specifically, three identically-configured positioning arches spaced 120° from one another respectively are used. These positioning arches are connected to one another by means of solid body articulations. Addition to the positioning arches, complementary curved retaining arches serve to anchor the endoprosthesis by pressing radially against the vascular wall following the unfolding of the stent.

However, there is a risk of inexact or incorrect implantation of a valvular prosthesis using the solutions described above. Expressed in another way. There is a need for exact positioning and longitudinal alignment of an implanted valvular prosthesis. In particular, it is only possible using great skill on the part of the attending surgeon or cardiologist—if at all—to position a stent sufficiently precisely, in both a lateral and longitudinal direction, to ensure that the associated valvular prosthesis is located in the correct area of the patient's diseased heart valve.

Among other things, inexact implantation of a sub-optimally positioned valvular prosthesis can lead to leakage or valvular insufficiency which results in considerable ventricular stress. For example, if a valvular prosthesis is implanted too far above the plane of the native heart valve, this can lead to closure or blocking of the coronary artery ostia (inlet orifice of coronaries) and thus to fatal coronary ischemia and myocardial infarction.

Therefore, for the optimal treatment of a narrowed cardiac valve or a cardiac valve insufficiency, it is necessary to position a stent, to which a valvular prosthesis is affixed, as precisely as possible at the site of implantation of the cardiac valve to be treated.

An endoprosthesis for treating aortic valve insufficiency is known from printed publication DE 20 2007 005 491 U1. The endoprosthesis comprises a valvular prosthesis and a stent to position and anchor the valvular prosthesis at the implantation site in the patient's heart. A stent having several (multiple, normally three, but two in case of bicuspid valve) positioning arches is employed in this endoprosthesis. In the implanted state of the stent, these positioning arches extend radially and serve to engage in the pockets of the native (diseased) cardiac valve to be treated. The valvular prosthesis affixed to the stent can then self-position into the plane of the cardiac valve. Retaining arches abut against the vascular wall of the aorta in the implanted state of the endoprosthesis, form a force-fit connection and are used to anchor the endoprosthesis.

While the positioning arches enable optimal positioning of the stent of this endoprosthesis at the site of implantation in the patient's heart, what cannot be ensured is that the valvular prosthesis attached to the proximal end of the stent is actually also positioned in the plane of the cardiac valve. In particular, substantial forces act on the valvular prosthesis during the filling phase of the heart cycle (diastole), which can lead to the valvular prosthesis displacing longitudinally relative the stent. Due to this longitudinal displacement of the implanted valvular prosthesis, which occurs in the heart and blood vessels especially because of the peristaltic motion of the heart, the implanted valvular prosthesis may no longer be able to provide a secure seal.

Moreover, there is the danger that, because of the longitudinal displacement of the valvular prosthesis relative the stent occurring with the peristaltic motion, the threads or sutures used to fasten the valvular prosthesis to the stent may chafe against the stent. It can therefore not be excluded that the fastening threads may fray over the course of time and thus lose their fastening function. This would result in at least a partial separation of the valvular prosthesis from the stent, which in turn can lead to leakages, an inappropriate positioning or even complete detachment of the valvular prosthesis.

On the basis of the problems outlined above, the present invention addresses the issue of providing a self-expandable endoprosthesis for treating a narrowed cardiac valve or a cardiac valve insufficiency which realizes optimum positioning accuracy and anchoring of a valvular prosthesis to be implanted. In addition, the treatment of the narrowed cardiac valve or cardiac valve insufficiency should be by way of a simple procedure to enable routine treatment of narrowed cardiac valve or cardiac valve insufficiency without major stress to the patient.

A further task of the present invention lies in specifying an endoprosthesis for the treatment of a stenosed cardiac valve or a cardiac valve insufficiency, whereby the endoprosthesis can be anchored securely at the site of implantation in the patient's heart. In addition, the present invention also addresses the issue of substantially preventing displacement of an implanted valvular prosthesis from its ideal site of implantation in spite of the forces acting on the endoprosthesis during the filling phase of the heart cycle.

From one aspect, an expandable stent is proposed in accordance with the present invention, the stent comprising at least one fastening portion by means of which a valvular prosthesis is connected to the stent. In particular, the stent comprises both positioning arches and retaining arches. At least one positioning arch of the stent is connected with at least one retaining arch of the stent by a first connecting web. Additionally, the stent further comprises at least one auxiliary arch which interconnects the arms of respective retaining arches.

The at least one fastening portion extends along the longitudinal axis of the stent and comprises a plurality of fastening holes distributed in a longitudinal direction at discrete positions along the length of the at least one fastening portion. Thread or thin wire may be guided through each fastening hole to secure the valvular prosthesis to the stent. The advantage of this feature is that longitudinal displacement of the valvular prosthesis relative to the stent is substantially minimized once implanted and so the prosthesis is not unduly disturbed or weakened as a result of the heart's peristaltic motion.

Depending from and between a pair of fastening portions is a fastening arch, over which valve tissue is laid. The fastening arch is located inside the circumference of the stent. In this way, the prosthesis tissue is separated and held away from positioning and retaining arches, thereby reducing the likelihood of these arches chaffing the tissue which, in turn may result in damage and weakening of the prosthesis. The fastening arch serves to anchor the lower edge of the valvular prosthesis and to tension the material so the prosthesis is effective as a valve. By having a fastening portion and fastening arches, the prosthesis is fully supported and anchored within the boundary of the stent. The combination of the two fastening mechanisms also provides a failsafe should one fastening mechanism fail. This is of particular relevance with suturing since a poorly sutured prosthesis will not be as effective as it should due to additional stresses and strains imparted to the prosthesis by the sutures. Thus, the arches allow fastening of the prosthesis in a manner that does not rely solely on suturing.

In an implanted configuration, the at least one positioning arches of the stent extends from the circumference of the stent in a generally radial direction. These positioning arches are designed to engage in the pockets of the native (diseased) cardiac valve that is being replaced which, in turn allows accurate positioning of the stent. Furthermore, on implantation, a positioning arch sits between the vascular wall and a leaflet of the native heart valve. The positioning arch then co-operates with a corresponding retaining arch resulting in clipping of the native leaflet between the two arches. In this way, the positioning and retaining arches together hold the stent in position and substantially eliminate axial rotation of the stent.

The at least one retaining arch is connected to a positioning arch by a connecting web. The retaining arch extends radially in the implanted state of the stent such that the at least one retaining arch presses against the wall of the blood vessel in which the stent is deployed with a radially-acting tensioning force. In addition to the at least one retaining arch, the invention provides for the stent to further comprise at least one auxiliary arch which interconnects the respective arms of the at least one retaining arch connected to the at least one positioning arch. As with the at least one retaining arch, the at least one auxiliary arch also protrudes radially in the expanded state of the stent when implanted such that the at least one auxiliary arch also presses against the wall of the blood vessel in which the stent is deployed with a radially-acting tensioning force.

In the at least one fastening portion of the stent, by means of which the valvular prosthesis can be fastened to the stent, a plurality of fastening holes is provided. These fastening holes are longitudinally distributed at given positions on the fastening portion and guide at least one thread or thin wire to fasten the valvular prosthesis to the stent, thereby enabling a precise positioning of the valvular prosthesis on the stent. Each individual fastening hole provided in the at least one fastening portion thereby serves to guide a thread or thin wire with which the valvular prosthesis is affixed or sewn to the fastening portion of the stent.

The means provided for fastening the valvular prosthesis to the fastening portion of the stent (thread or thin wire) is guided by way of the fastening holes so that a longitudinal displacement of the valvular prosthesis relative the stent is substantially minimized. This also allows exact positioning of the valvular prosthesis relative the stent.

The secure and defined fixing of the valvular prosthesis to the at least one fastening portion of the stent moreover effectively prevents the means used to fasten the valvular prosthesis to the stent (threads or thin wires) from rubbing against the stent and thus degrading after a longer period of use.

In order to configure the plurality fastening holes in the fastening portion, the at least one fastening portion is preferably configured as—in comparison to the respective arms of the positioning arch, retaining arch and auxiliary retaining arch—a widened segment. Thus, the fastening portion is a stent segment which comprises a relatively large amount of material, facilitating movement and position analysis when the stent is being implanted. For example, when fluoroscopy (cardiac catheterization=LHK) or ultrasound (trans-esophageal echocardiogram=TEE) is used to monitor the insertion procedure, the fastening portion of the stent is particularly distinguishable.

In manufacturing the stent used in the endoprosthesis according to the invention, it is conceivable for the stent to exhibit a structure integrally cut from a portion of tube, in particular from a small metal tube, which incorporates the positioning arches, retaining arches and auxiliary retaining arches as well as the at least one fastening portion with the defined fastening holes. Specifically, it is conceivable to use a laser to cut the stent structure from the small metal tube, whereby the structure is thereafter subject to an applicable shaping and thermal treatment process so that the stent can transform from a collapsed state during implantation into an expanded state at the site of implantation. This shaping and thermal treatment process is advantageously performed gradually in order to prevent damage to the stent structure.

Particularly preferred is for the stent to exhibit a structure integrally cut from a small metal tube in which each positioning arch is allocated one retaining arch, and in which each upper end portion of the positioning arch towards the upper end of the stent is connected with the upper end portion of the associated retaining arch via a first connecting web. The at least one fastening portion, in which the plurality of fastening holes is provided, is thereby preferably configured within an arm of the retaining arch.

It is to be understood that the term "upper" refers to the stein when viewed in its implanted state. In other words, the term "upper" refers to the distal end of the stent which, when implanted, is sited away from the heart. Similarly, use of the term "lower" refers to a proximal position on the stent which is located towards the heart when the stent is viewed in its implanted position.

A preferred realization of the stent according to invention provides for a fastening portion to be configured within each arm of the stent's retaining arch.

In order to be able to reinforce the respective retaining arches of the stent, the auxiliary arch as already mentioned above is provided and which extends from the lower ends of the fastening portion and connects the respective arms of two neighboring retaining arches.

The stent preferably exhibits an integrally-formed structure which can transform from a first predefinable shape into a second predefinable shape, whereby the stent exhibits a first predefinable shape (collapsed shape) during insertion into the patient's body and a second predefinable shape (expanded shape) once implanted. Because of the stent's design, during the transition of the stent from the first predefinable shape into the second predefinable shape, the positioning arches, retaining arches and auxiliary arches are radially expanded as a function of the cross-sectional expansion of the stent. The stent's second shape is thereby preferably selected such that when expanding, the retaining arch and the auxiliary arch abut against the wall of the blood vessel in which the stent is deployed.

To achieve a secure anchoring of the stent at the site of implantation, both the retaining and auxiliary arches should press against the wall of the vessel with a radial force, whereby this radial force can be set by subjecting the stent structure to a suitable shaping and thermal treatment process.

A preferred embodiment of the stent according to the invention provides for the positioning arches and the associated retaining arches as well as auxiliary arches each to exhibit an essentially U-shaped, T-shaped or V-shaped structure which is closed toward the lower end of the stent. It is particularly preferred for each positioning arch to be cut from the material portion of a small metal tube from which the essentially U-shaped, T-shaped or V-shaped structure of the associated retaining arch was taken. The respective auxiliary arches are preferably cut from a material portion of the small metal tube situated between the essentially U-shaped, T-shaped or V-shaped retaining arch structures.

This preferred embodiment of the stent structure thus provides for the respective retaining and auxiliary arches of the stent to form the lower region of the endoprosthesis, whereby the positioning arches are configured symmetrically to the retaining arches although preferably disposed somewhat farther toward the upper region of the endoprosthesis.

The respective upper ends of the positioning arches are connected to the respective upper ends of the associated retaining arches by means of a first connecting web in the upper region of the endoprosthesis. The fastening portions are configured in the respective arms of the retaining arch. In the expanded state of the stent, both the lower region with the fastening portions, as well as the connecting web disposed at the upper end of the stent between the respective positioning and retaining arches, spread out so that a radially-acting force is exerted on the blood vessel wall from both the lower region of the stent as well as the upper end of the stent, thereby enabling secure anchoring of the stent at the site of implantation.

In a preferred embodiment, the stent exhibits in its first shape (collapsed shape) an outer diameter of approximately 4 to 8 mm and a length of between 30 mm and 40 mm, preferably between 34.0 and 39.0 mm, and more preferably between 34.37 mm and 38.37 mm. This allows the stent to be inserted easily into the patient's body, for example with a 21F delivery system, and to be used with a valvular prosthesis having a diameter of between 19 mm and 28 mm. The afore-mentioned length specifications are the dimensions currently preferred, based on which the stent becomes suitable for the majority of patients to be treated.

In order to achieve a particularly secure anchoring of the implanted stent with the stretched valvular prosthesis affixed thereto, it is further conceivable for the stent to be subject to a shaping and thermal treatment process during its manufacture such that the finished stent exhibits a slightly concave configuration tapering toward its lower end in its second shape.

In other words, the lower end portion of the stent; i.e., that area in which the valvular prosthesis is fastened, exhibits a somewhat tapered diameter in comparison to the upper end portion. Specifically, it has been seen that, when the stent is in it second shape and the upper end of the stent exhibits a diameter approximately 10-25% larger than the diameter of its lower end, radial forces are generated particularly at the stent's upper end. This enables a secure hold of the stent in the blood vessel without damaging the arterial wall. This configuration also provides secure anchoring that is able to withstand the peristaltic motion of the heart and the arterial wall. The somewhat lesser radial force exerted by the lower end of the stent not only serves to anchor the stent in the blood vessel but also to stretch the valvular prosthesis attached at the lower end and reliably seal the prosthesis against the arterial wall. It is of course also conceivable to design the concave configuration of the stent in its second shape to be of greater or lesser concavity.

It is preferable for the lower end area of the stent, when in its second shape, to exhibit a diameter of between 22 mm and 33 mm, preferably between 25 mm and 31 mm. It is conceivable for the stent to exhibit two or more differently dimensioned sizes whereby the optimal stent size can be selected depending upon specific patient. In addition, exact and patient-specific dimensions of the stent—starting from a given stent size—can be realized by appropriately curing the stent, in particular by a thermal treatment process.

In a particularly preferred realization, the stent comprises a valvular prosthesis, preferably a biological valvular prosthesis, which is attached to the at least one fastening portion of the stent by means of a thread or the like.

A shape memory material is preferably used as the material for the stent, the material being designed such that the stent can transform from a temporary shape into a permanent shape under the influence of an external stimulus. The temporary shape is thereby the stent's first shape (i.e. the collapsed state of the stent), while the permanent shape is assumed in the stent's second shape (i.e. in the expanded state of the stent). In particular, use of a shape memory material such as nitinol, i.e. an equiatomic alloy of nickel and titanium, allows for a particularly gentle implantation procedure when implanting the stent.

When manufacturing the stent preferably made from a shape memory material, the stent structure is preferably shaped after it has been cut from a tube. Once the desired shape has been formed, this shape is "fixed", this process being known as "programming." Programming may be effected by heating the stent structure, forming the stent into the desired shape and then cooling the stent. Programming may also be effected by forming and shaping the stent structure at lower temperature, this being known as "cold stretching." The permanent shape is thus saved, enabling the stent to be stored and implanted in a temporary, non-formed shape. If an external stimulus then acts on the strait structure, the shape memory effect is activated and the saved, permanent shape restored.

A particularly preferred embodiment provides for the external stimulus to be a definable switching temperature. It is thus conceivable that the stent material needs to be heated to a higher temperature than the switching temperature in order to activate the shape memory effect and thus regenerate the saved permanent shape of the stent. A specific switching temperature can be preset by the relevant selection of the chemical composition of the shape memory material.

It is particularly preferred to set the switching temperature to be in the range between room temperature and the patient's body temperature. Doing so is of advantage, especially with regard to the medical device being used as an implant in a patient's body. Accordingly, all that needs to be ensured in this regard when implanting the stent is that the stent is warmed up to the patient's body temperature (36° C.) at the site of implantation to activate the shape memory effect of the stent material.

The following will make reference to the included drawings in describing preferred embodiments of the stent according to the present invention in greater detail.

Figure 1B:
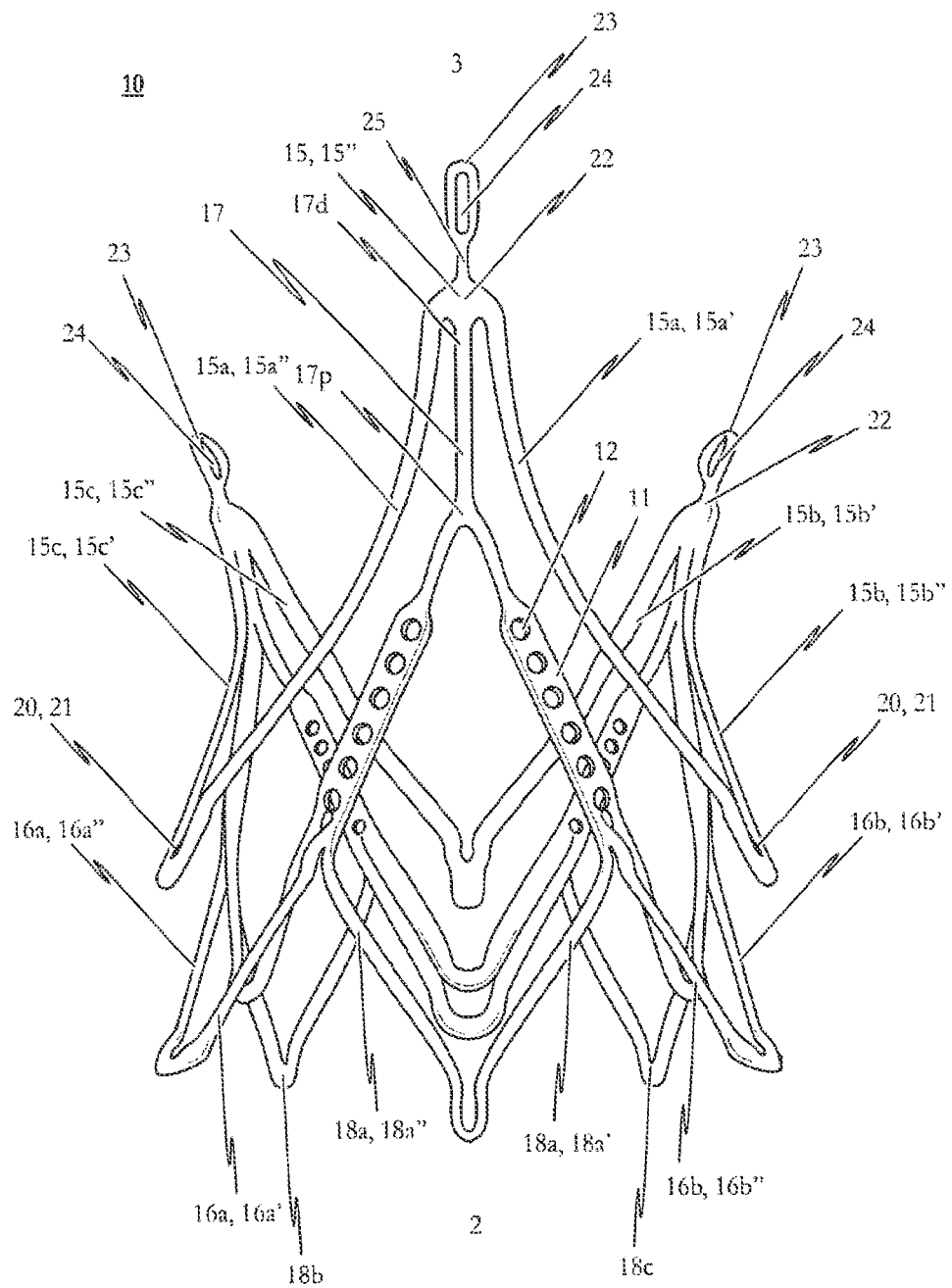
Figure 1E:
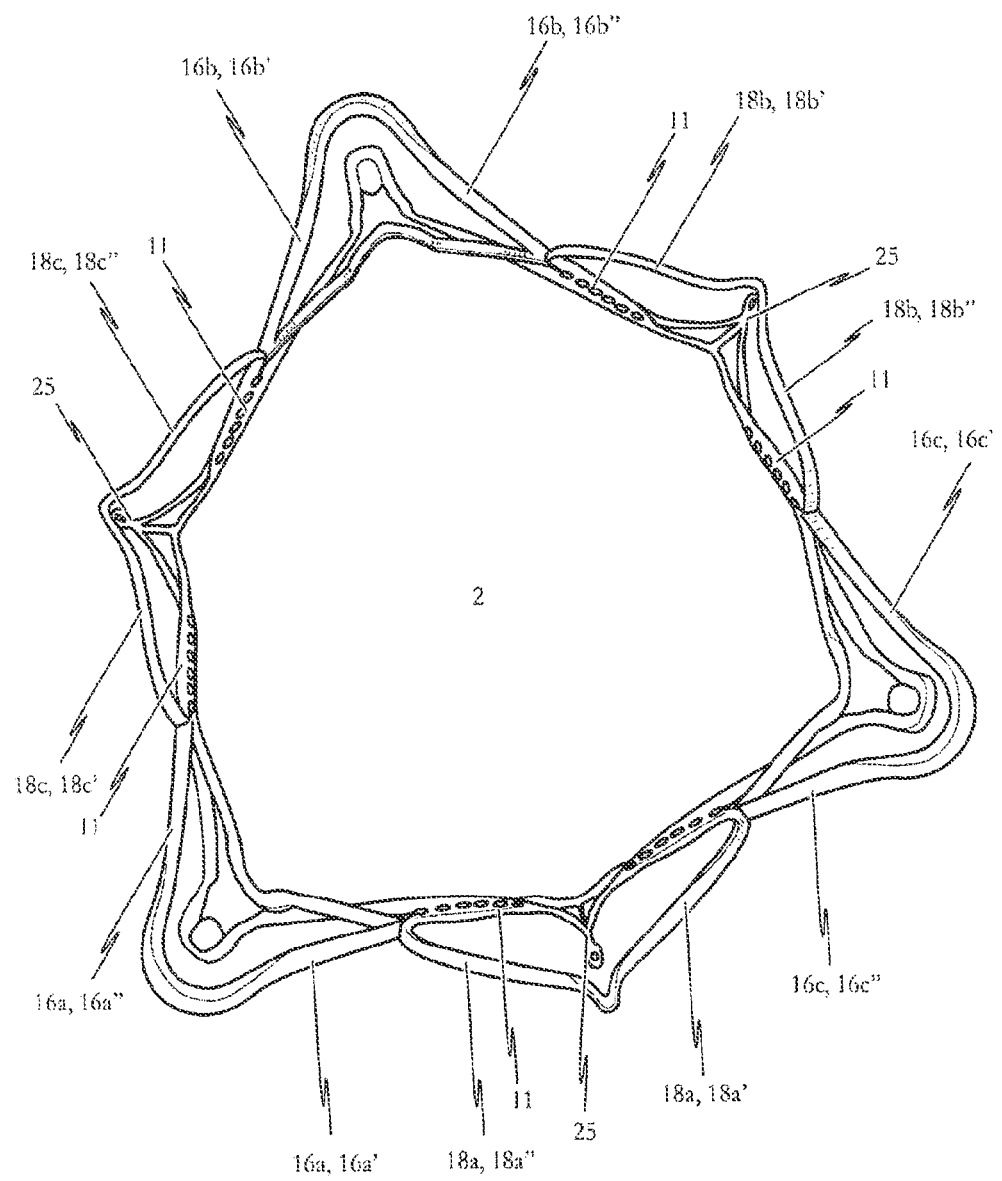
Figure 1D:
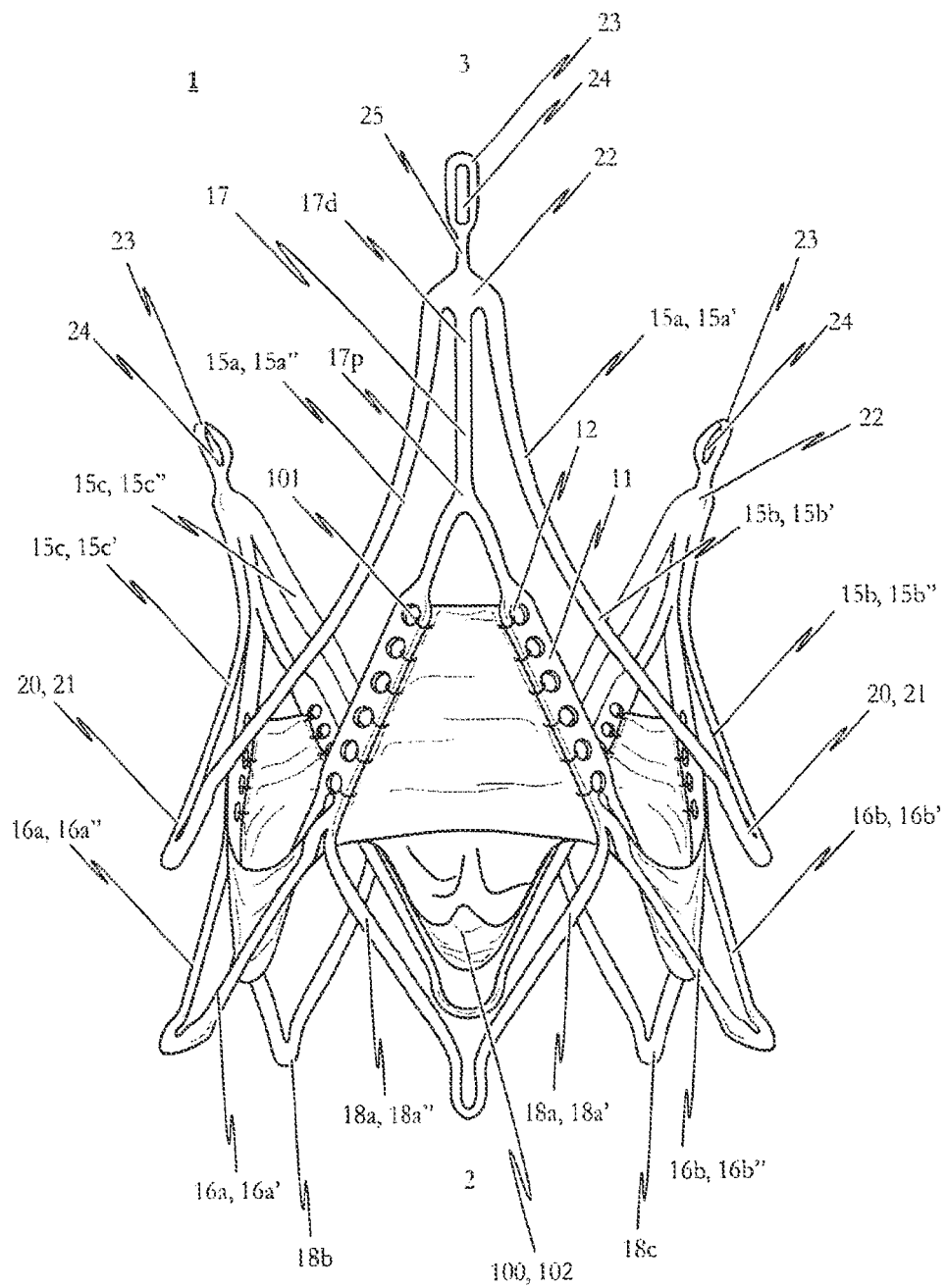
Figure 1E:
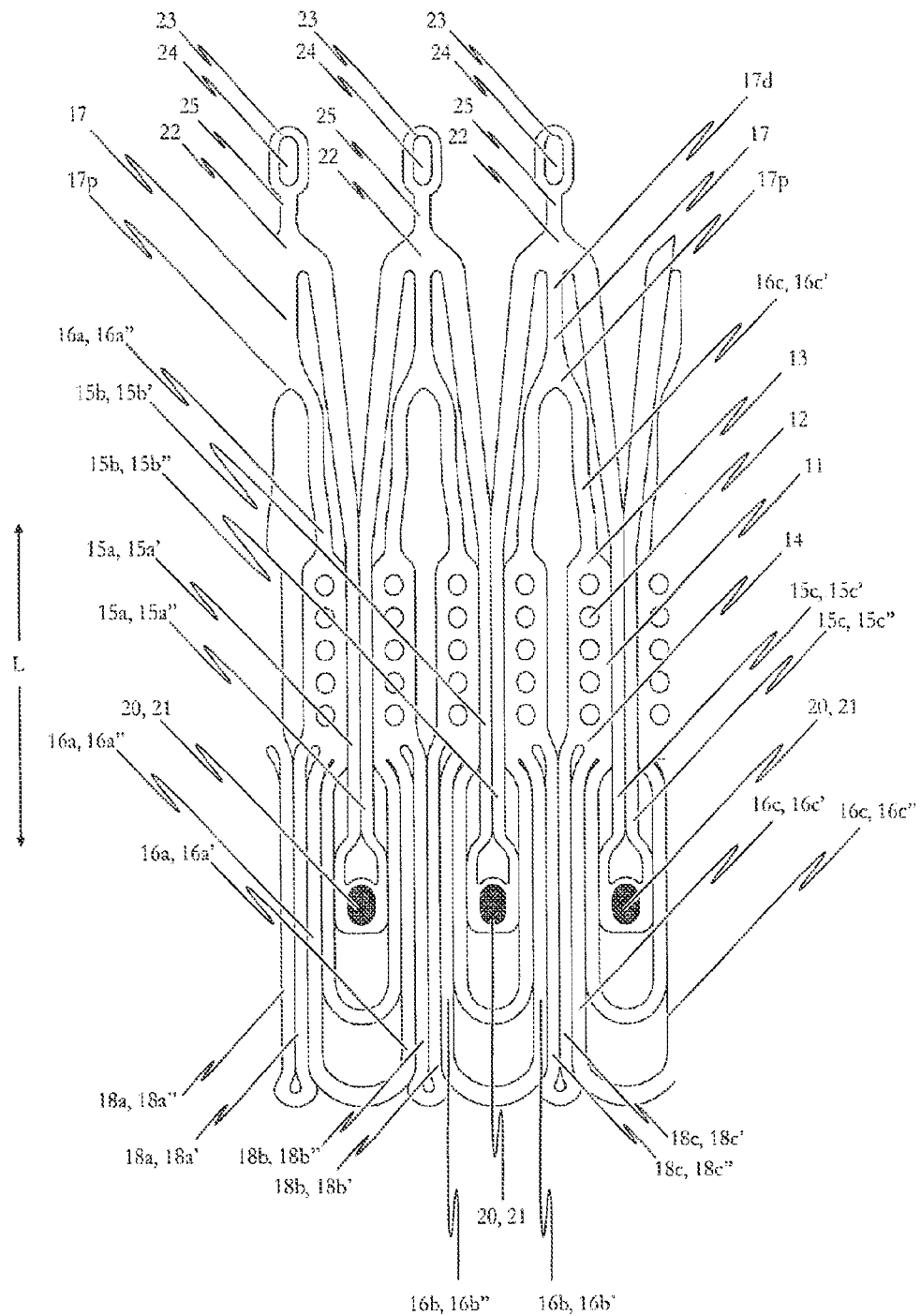
Figure 2A:
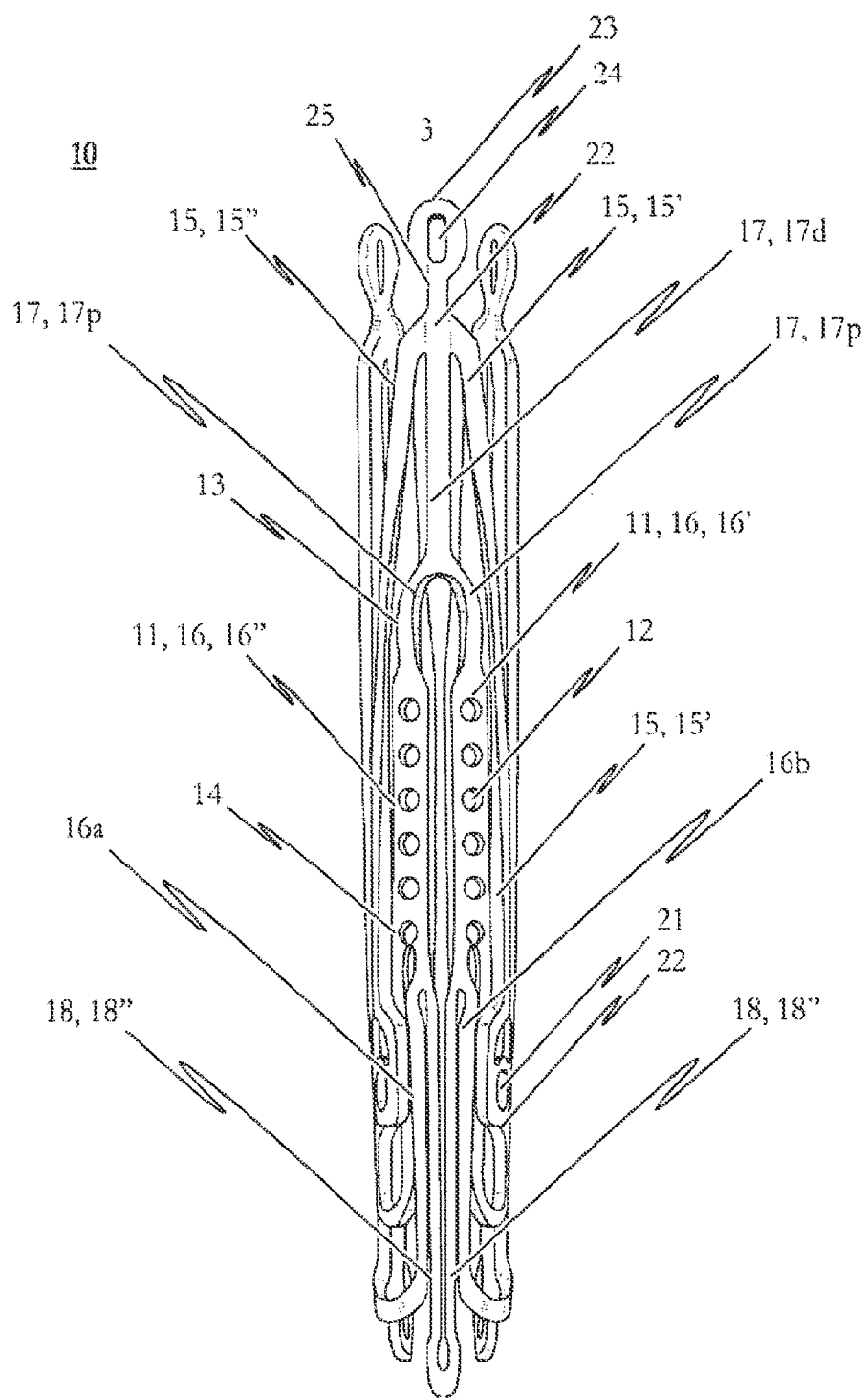
Figure 2B:
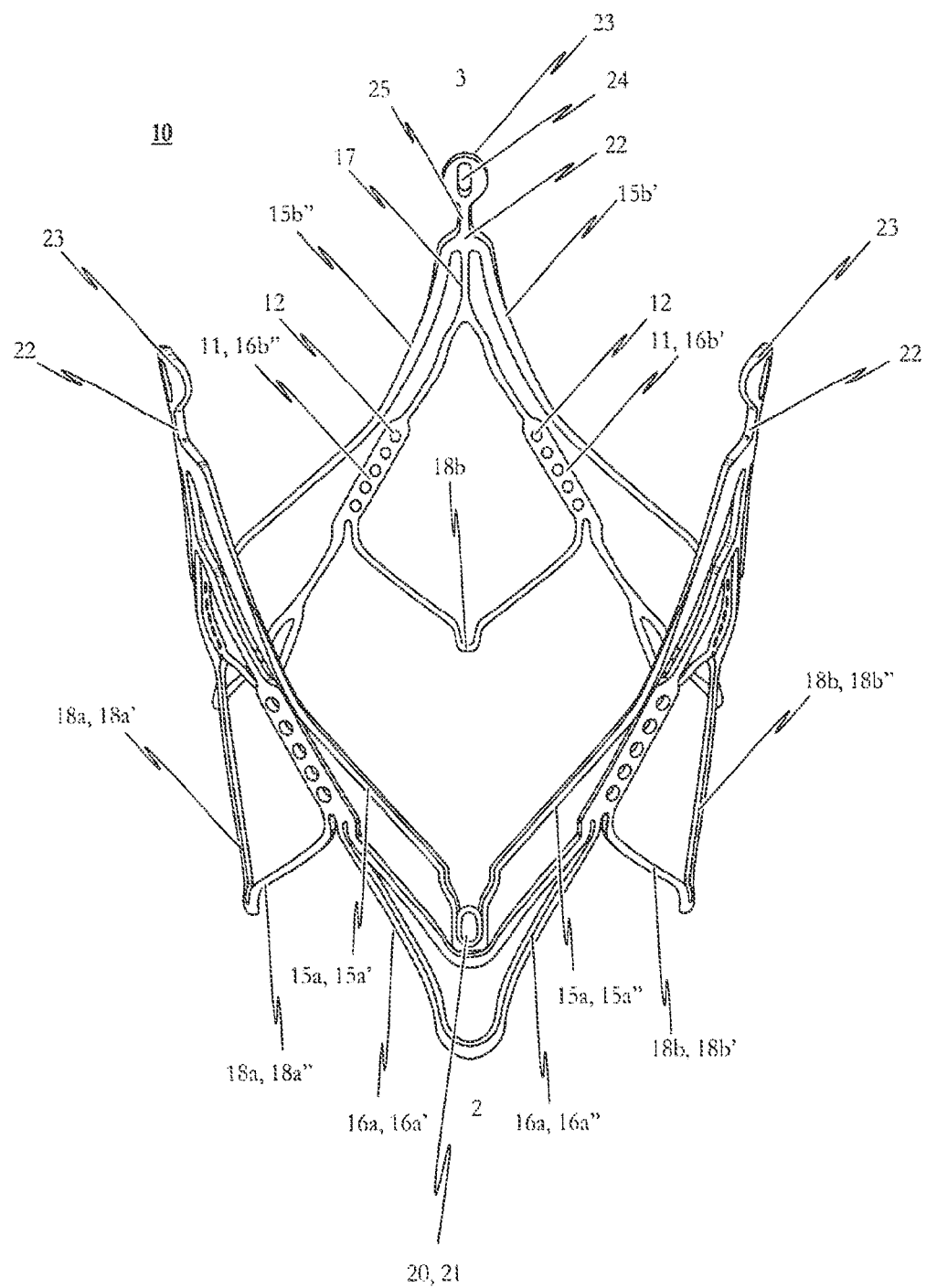
Figure 2C:
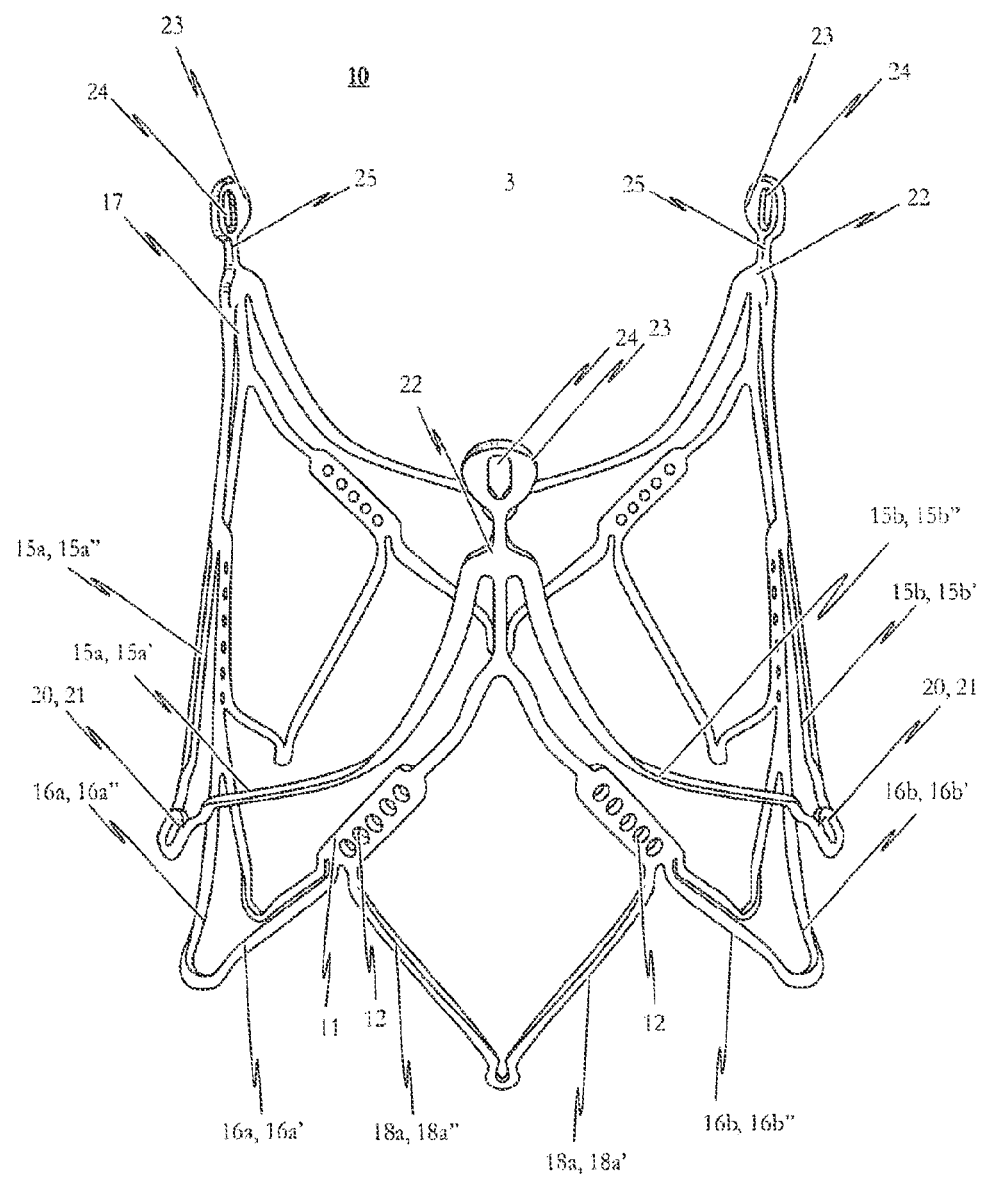
Figure 2D:
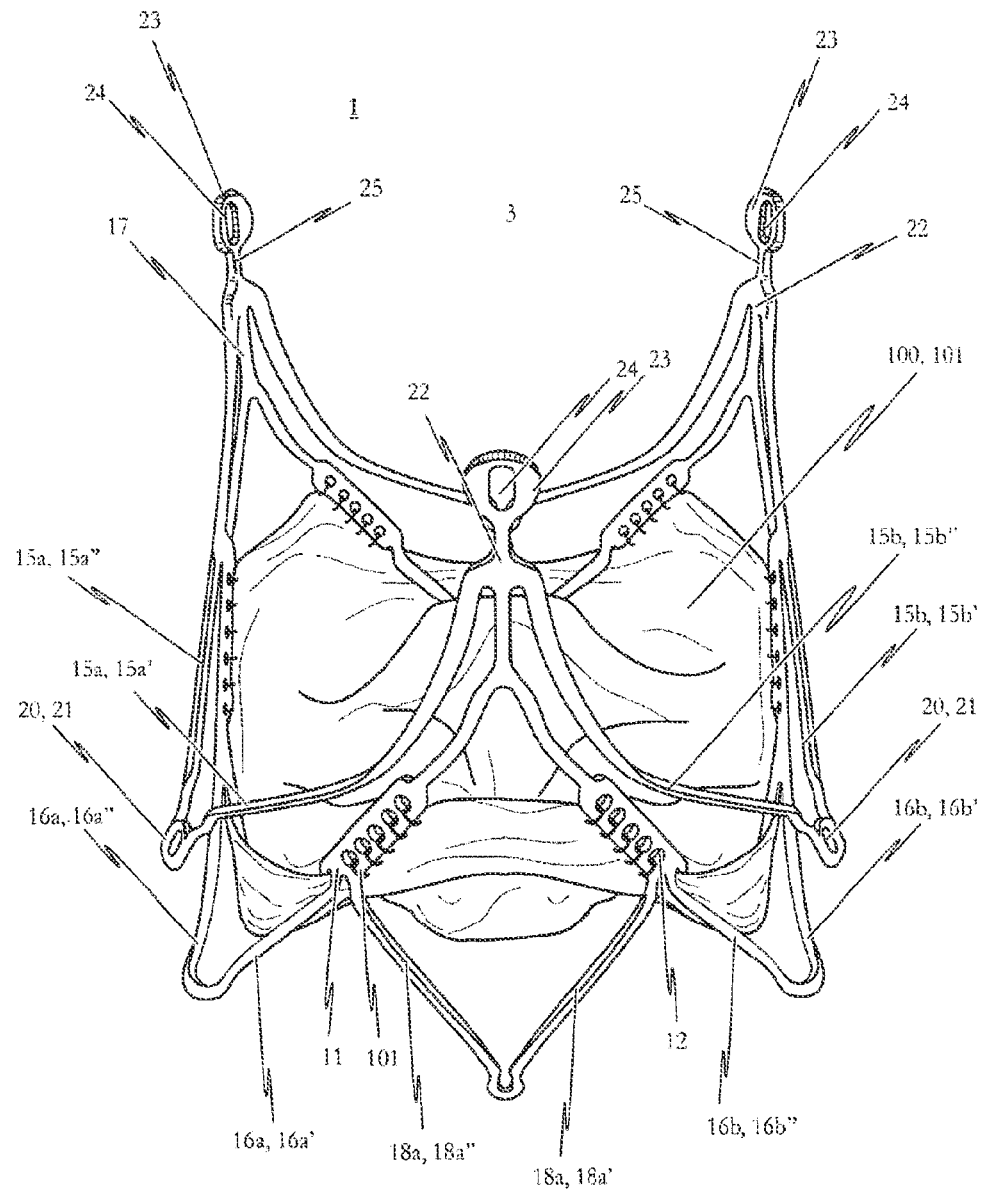
Figure 2E:
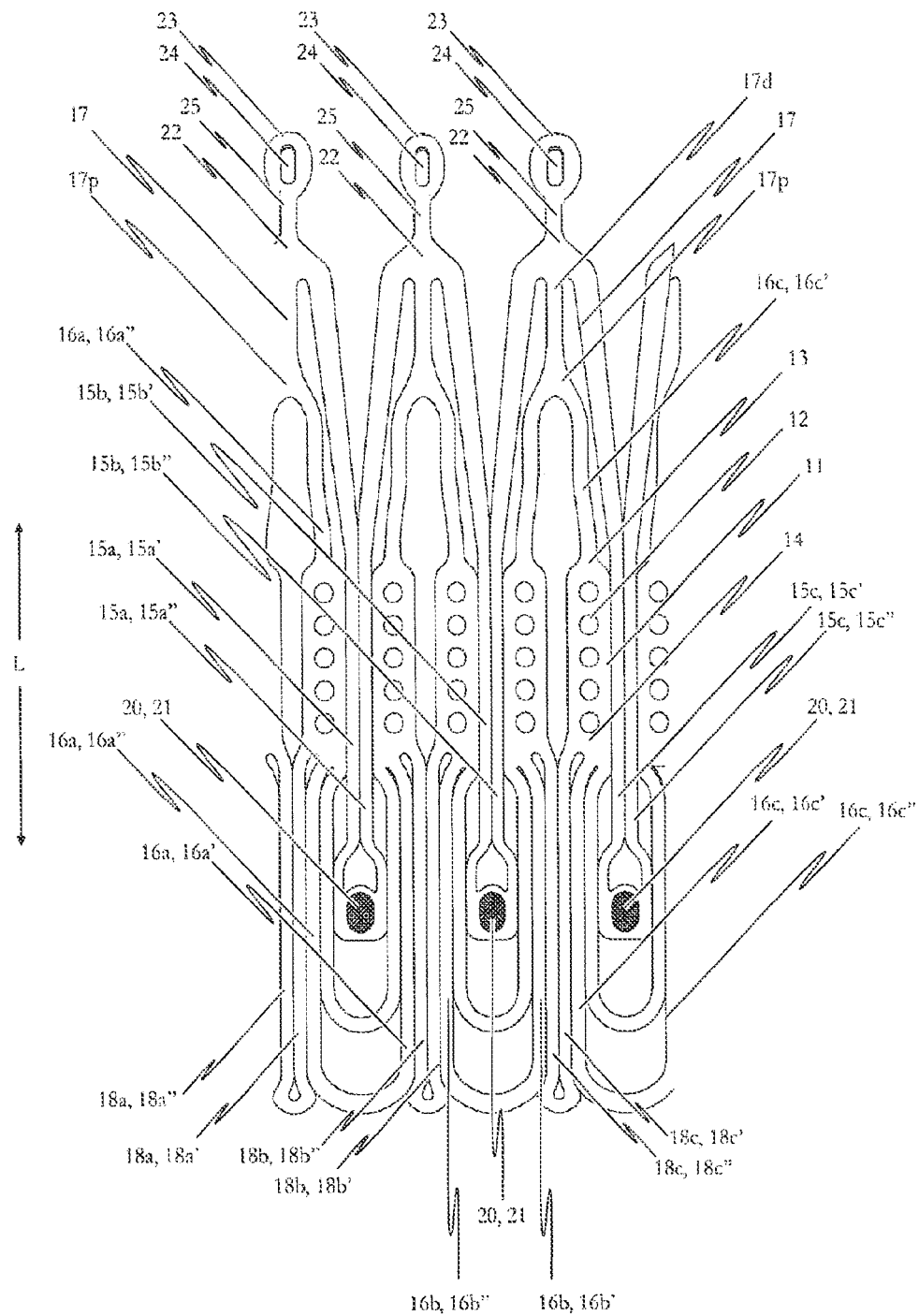
Figure 3C:
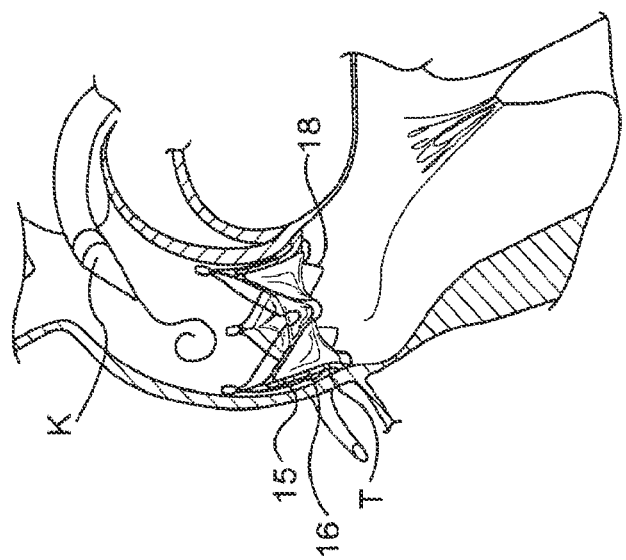
Figure 3B:
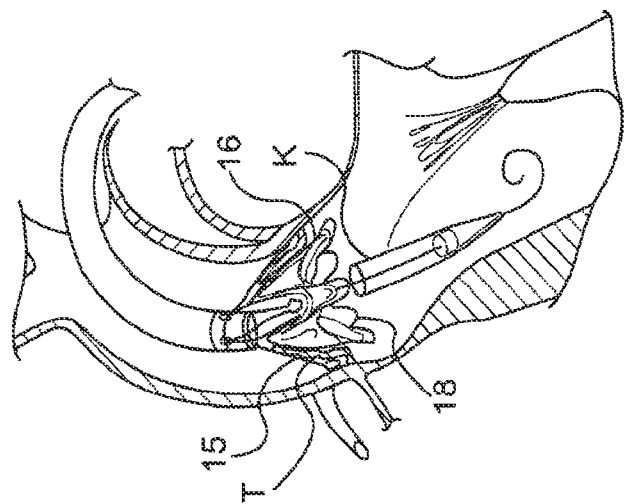
Figure 3A:
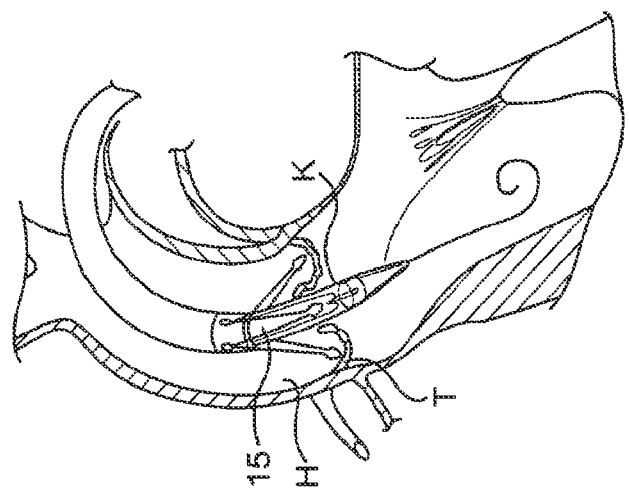

Shown are:

FIG. 1a a perspective side view of a cardiac valve stent in accordance with a first embodiment of the invention, where the cardiac valve stent is shown in its collapsed state;

FIG. 1b a perspective side view of the cardiac valve stent in accordance with the first embodiment of the invention, where the cardiac valve stent is shown in its expanded state;

FIG. 1c a perspective top plan view of the proximal end of the cardiac valve stent in accordance with the first embodiment of the invention, where the cardiac valve stent is shown in its expanded state;

FIG. 1d a perspective side view of an endoprosthesis for treating a narrowed cardiac valve or a cardiac valve insufficiency, where the endoprosthesis comprises the cardiac valve stent according to the first embodiment of the invention for holding a valvular prosthesis;

FIG. 1e a two-dimensional projection of a cutting pattern applicable to manufacturing the cardiac valve stent according to the first embodiment of the invention in order to cut a cardiac valve stent pursuant FIG. 1a integrally from a portion of tube, in particular a small metal tube;

FIG. 2a a perspective side view of a cardiac valve stent according to a second embodiment of the invention, where the cardiac valve stent is shown in its collapsed state;

FIG. 2b a first perspective side view of the cardiac valve stent according to the second embodiment of the invention, whereby the cardiac valve stent is shown in its expanded state;

FIG. 2c a second perspective side view of the cardiac valve stent according to the second embodiment of the invention, where the cardiac valve stent is shown in its expanded state;

FIG. 2d a perspective side view of an endoprosthesis for treating a narrowed cardiac valve or a cardiac valve insufficiency, where the endoprosthesis comprises the cardiac valve stent according to the second embodiment of the invention for holding a valvular prosthesis;

FIG. 2e a two-dimensional projection of a cutting pattern applicable to manufacturing the cardiac valve stent according to the second embodiment of the invention in order to cut a cardiac valve stent pursuant FIG. 2a integrally from a portion of tube, in particular a small metal tube; and FIG. 3a-c a process sequence illustrating a transarterial implantation of an endoprosthesis comprising a cardiac valve stent in accordance with the invention.

Both the right and left halves of the human heart consist of a ventricle and an atrium. These cavities are separated by the septum of the heart, divided into the atrial septum (septum interatriale) and the ventricular septum (septum interventriculare).

Blood can only flow in one direction through the chambers of the heart due to the cardiac valves situated between the atria and ventricles and in the arteries connected to the ventricles which function like mechanical valves. The superior and inferior vena cava (vena cava superior et inferior) flow into the right atrium. They supply the oxygen-depleted (venous) blood from the systemic circulation to the heart. The tricuspid valve which, like a mechanical valve, prevents a reverse flow of blood into the atrium upon ventricular contraction (systole) is situated between the right atrium and the right ventricle. It comprises three segments which are affixed like flaps to the ventricular musculature by ligaments (hence also called the "flap valve"). The two pulmonary arteries depart the tight ventricle of the heart via a common trunk (truncus pulmonalis). There is also a valve between the ventricle and the pulmonary trunk, the so-called pulmonary valve. This type of valve is also called a semilunar valve due to its shape. The pulmonary arteries supply the oxygen-depleted blood to the pulmonary circulation.

Oxygen-rich (arterial) blood then usually flows through four pulmonary veins from the pulmonary circulation to the left atrium. From there, it reaches the left ventricle through a further flap valve, the mitral valve. The outflow is carried by the aorta which, like the pulmonary artery, has a semilunar valve (aortic valve).

During a heart cycle, the atria fill first while the ventricles concurrently disgorge the blood into the arteries. When the ventricular musculature relaxes, the flap valves open due to the drop in pressure in the ventricle and the blood flows in from the atria (auricular systole). This is supported by a contraction of the atria. Ventricular contraction follows: the ventricular musculature contracts, the pressure rises, the flap valves close and the blood can now only flow into the arteries through the now-opened semilunar valves. A reverse blood flow from the arteries during the relaxation phase (diastole) is prevented by the closing of the semilunar valves such that the direction of flow is determined solely by the valves.

The four cardiac valves work like mechanical valves in the heart and prevent a reverse flow of blood in the wrong direction. Each half of the heart has a flap valve (atrioventricular valve) and a semilunar valve. The atrioventricular valves are situated between the atrium and the ventricle and are called the bicuspid/mitral valve and the tricuspid valve. The semilunar valves are situated between the ventricle and the vascular outflow and are called the pulmonary valve and the aortic valve respectively.

A valve defect; i.e. a dysfunctioning of a cardiac valve's function, can affect any of the four cardiac valves, although the valves on the left side of the heart (aortic and mitral valves) are affected considerably more frequently than those on the right side of the heart (pulmonary and tricuspid valves). Dysfunction can encompass constriction (stenosis), insufficiency or a combination of the two (combined vitium).

In medicine, the term "aortic valve insufficiency", or "aortic insufficiency" for short, refers to the defective closing of the heart's aortic valve and the diastolic reverse flow of blood from the aorta into the left ventricle as a result. Depending on the severity of the aortic insufficiency and the extent of resistance to aortic depletion, the volume of reverse flow can be up to two thirds of the left ventricle's ejection volume (normal cardiac output 40 to 70 ml). This results in characteristically high blood pressure amplitude. This regurgitant bloodflow increases the diastolic filling of the left chamber and leads to a volume overload of this section of the heart, a consequence of which is eccentric hypertrophy.

Aortic valve stenosis is a valvular heart disease caused by the incomplete opening of the aortic valve. When the aortic valve becomes stenotic, it causes a pressure gradient between the left ventricle and the aorta. The more constricted the valve, the higher the gradient between the left ventricle and the aorta. For instance, with a mild aortic valve stenosis, the gradient may be 20 mmHg. This means that, at peak systole, while the left ventricle may generate a pressure of 140 mmHg, the pressure that is transmitted to the aorta will only be 120 mmHg.

In individuals with Aortic valve stenosis, the left ventricle has to generate an increased pressure in order to overcome the increased afterload caused by the stenotic aortic valve and eject blood out of the left ventricle. The more severe the aortic stenosis, the higher the gradient is between the left ventricular systolic pressures and the aortic systolic pressures. Due to the increased pressures generated by the left ventricle, the myocardium (muscle) of the left ventricle undergoes hypertrophy (increase in muscle mass).

Angina in the setting of aortic valve stenosis is secondary to the left ventricular hypertrophy that is caused by the constant production of increased pressure required to overcome the pressure gradient caused by the aortic valve stenosis. While the myocardium (i.e. heart muscle) of the left ventricle gets thicker, the arteries that supply the muscle do not get significantly longer or bigger, so the muscle may become ischemic (i.e. doesn't receive an adequate blood supply). The ischemia may first be evident during exercise, when the heart muscle requires increased blood supply to compensate for the increased workload. The individual may complain of exertional angina. At this stage, a stress test with imaging may be suggestive of ischemia.

Mitral valve insufficiency (also called mitral insufficiency) is a frequent cardiac valve defect in human medicine and also in at least some animal species. It involves a closing defect or "leakage" of the heart's mitral valve which leads to reverse bloodflow from the left ventricle into the left atrium during the ejection phase (systole).

The mitral valve functions like a mechanical valve between the left atrium and the left ventricle of the heart. It opens during the filling phase of the ventricle (diastole) and thus enables the inflow of blood from the atrium. At the beginning of the ejection phase (systole), the sudden increase in pressure in the ventricle leads to the closing of the valve and thus to a "sealing" of the atrium. In so doing, a pressure of only about 8 mmHg prevails in the atrium, while at the same time the systolic pressure of about 120 mmHg in the ventricle forces the blood along its usual path into the main artery (aorta).

In cases of severe mitral insufficiency, however, the regurgitation opening is larger than 40 $mm^2$ and the regurgitation volume greater than 60 ml, which can lead to serious and at times life-threatening changes.

In the acute stage, with a normal size to the left ventricle and the left atrium, there is a considerable increase of the pressure in the atrium and thus also in the pulmonary veins. This can be up to 100 mmHg which, given a normal condition to the pulmonary vessels, leads to immediate pulmonary edema. The then predominantly reverse blood flow can moreover result in insufficient ejection outflow into the aorta and thus decreased blood flow to all the organs.

To treat a severe narrowed cardiac valve or cardiac valve insufficiency, it is necessary for a valvular prosthesis to perform the valve function of the narrowed, diseased or diseased cardiac valve. Essential in this respect is that the valvular prosthesis is securely positioned and anchored in the implantation site in the heart; i.e. in the plane of the (diseased) cardiac valve to be replaced, so that the valvular prosthesis is not displaced or shifted despite the, at times considerable, forces acting on it. An effective seal during systole is also important.

A cardiac valve stent 10, to which the valvular prosthesis 100 is appropriately affixed, is employed in accordance with the invention to position and anchor said valvular prosthesis. A medical device for the treating of a narrowed cardiac valve or a cardiac valve insufficiency consisting of a cardiac valve stent 10 and a valvular prosthesis 100 affixed to the stent 10 will be referred to herein simply as endoprosthesis 1.

FIG. 1d shows a perspective side view of such an endoprosthesis 1 for treating a narrowed cardiac valve or a cardiac valve insufficiency, whereby the endoprosthesis 1 comprises a cardiac valve stent 10 to hold a valvular prosthesis 100 in accordance with a first embodiment of the invention. FIG. 2d likewise shows a perspective side view of a further endoprosthesis 1 for treating a narrowed cardiac valve or a cardiac valve insufficiency, whereby here a cardiac valve stent 10 in accordance with a second embodiment of the invention is employed.

The following will make reference to the included drawings in describing the presently preferred embodiments of the present invention in detail. The cardiac valve stent 10 according to the invention (hereinafter referred to simply as "stent") exhibits an expandable structure which is able to transform from a first predefinable shape in which the stent 10 is in a collapsed state into a second predefinable shape in which the stent 10 is in an expanded state. FIG. 1a shows a perspective side view of the stent 10 according to the first embodiment of the invention, whereby the stent 10 is in its collapsed state. FIG. 2a shows the collapsed stent 10 according to the second embodiment of the invention.

In the two embodiments, the stent 10 can be introduced in minimally-invasive fashion into the body of a patient in its first shape (cf. FIG. 1a and FIG. 2a) using an insertion catheter system (not explicitly shown in the drawings). During insertion, the valvular prosthesis 100 affixed to the stent 10 is likewise in a collapsed state. For the sake of clarity, however, both FIGS. 1a and 2a dispense with a representation of the valvular prosthesis 100 affixed to the stent 10.

Upon reaching the site of implantation in the patient's heart, the stent 10 transforms, preferably incrementally, into its second (expanded) shape in which also the valvular prosthesis 100 affixed to the stent 10 unfolds and expands. The second, expanded shape is a permanent shape that has been set by programming. The completely expanded stent 10 according to the first/second embodiment of the invention with the likewise completely unfolded and expanded valvular prosthesis 100 affixed thereto is shown in FIG. 1d and FIG. 2d.

FIG. 1b and FIG. 1c show the completely expanded stent 10 according to the first embodiment of the invention without the valvular prosthesis 100 from respectively different perspectives. FIGS. 2b and 2c show the completely expanded stent 10 according to the second embodiment of the invention, likewise without the valvular prosthesis 100, from respectively different perspectives.

The following will initially make reference to FIGS. 1a to 1e in describing the first embodiment of the inventive cardiac valve stent 10.

The stent 10 according to the first embodiment exhibits a structure integrally cut from a portion of tube, in particular a small metal tube. The cutting pattern used to form the design of the stent is depicted in a two-dimensional projection in FIG. 1e.

In detail, the stent 10 of the depicted first embodiment comprises a total of three positioning arches 15a, 15b, 15c which assume the function of self-positioning the stent into the plane of the pulmonary valve (valva trunci pulmonalis) or aortic valve (vulva aortae). The positioning arches 15a, 15b, 15c exhibit a rounded head portion 20 which engages in the pockets T of the (diseased) cardiac valve to be treated during positioning of the stent 10 at the site of implantation in the heart (cf. FIG. 3a).

Providing a total of three positioning arches 15a, 15b, 15c allows for the required positioning accuracy of stent 10 in the direction of rotation. The invention is of course not limited to the use of a total of three positioning arches.

The head portions 20 of the positioning arches 15a, 15b, 15c, respectively pointing towards the lower end 2 of the stent 10, are correspondingly rounded so that the vascular wall will not be damaged when the positioning arches 15a, 15b, 15c, engage in the pockets T of the cardiac valve H to be replaced. It is moreover preferred with respect to improving movement and position analysis during the implanting of the stent 10 for reference markers 21 to be provided on or within the head portions 20 of the positioning arches 15a, 15b, 15c. Radio opaque markers or markers which can be activated by infrared or ultrasound lend themselves particularly well hereto.

Specifically, the positioning arches 15a, 15b, 15c respectively exhibit an essentially U-shaped or V-shaped structure which is closed to the lower end of stent 10. Accordingly, each positioning arch 15a, 15b, 15c has a total of two arms 15a', 15a", 15b', 15b", 15c', 15c" respectively extending from the head portion 20 of the associated positioning arch 15a, 15b, 15c toward the upper end 3 of stent 10. By doing so, each two adjoining arms of two neighboring positioning arches are connected to one another via a connecting portion 22.

For implanting and explanting the stent 10 with a suitable catheter system, the stent 10 comprises catheter retaining means 23 at its upper end 3. The respective connecting portions 22, via which two respectively adjoining arms of two neighboring positioning arches are connected together, are respectively connected to catheter retaining means 23 via a connecting web 25. The connecting webs 25, which connect the connecting portions 22 to the associated catheter retaining means 23, will herein be referred to as "second connecting web 25."

In the stent 10 according to the first embodiment of the invention, the catheter retaining means 23 comprise oval-shaped heads which each respectively comprise a likewise oval-shaped eyelet 24. Conceivable hereto would be providing a crown with a total of three protruding elements in the tip of a catheter of a catheter system used to implant/explant stent 10. The protruding elements of the crown are thereby to be configured complementary to the eyelets 24 which are disposed on the catheter retaining means 23 provided at the upper end 3 of stent 10 and configured as catheter retaining heads. This realization would enable the protruding elements of the crown to form a releasable engagement with the upper area 3 of stent 10 to releasably attach stent 10 to the tip of the catheter of the catheter system used to implant/explant stent 10.

The upper end portion 17d of a first connecting web 17 extending essentially in longitudinal direction L of stent 10 furthermore opens to each connecting portion 22 between the two arms 15a', 15a", 15b', 15b", 15c', 15c" of two neighboring positioning arches 15a, 15b, 15c in addition to the previously-mentioned second connecting web 25. As can be seen in FIG. 1b, the respective first connecting webs 17 are of essentially Y-shaped configuration and each exhibit a structure that is spread at its lower end 17p which gives way to the respective arms 16a', 16a", 16b', 16b", 16c', 16c" of two neighboring retaining arches 16a, 16b, 16c.

This stent design achieves an axially symmetrical structure, whereby each positioning arch 15a, 15b, 15c is allocated one retaining arch 16a, 16b, 16c. The stent 10 of the first embodiment depicted in FIGS. 1a to 1d thus comprises a total of three retaining arches 16a, 16b, 16c which constitutes a retaining segment of stent 10 for accommodating a valvular prosthesis 100 as depicted for example in FIG. 1d.

In the state of the stent 10 shown in FIG. 1a, in which stent 10 is in its first (collapsed) shape, the respective arms 15a', 15a", 15b', 15c', 15c" of the positioning arches 15a, 15b, 15c directly adjoin the respective arms 16a', 16a", 16b', 16b", 16c', 16c" of the associated retaining arches 16a, 16b, 16c.

Reference is made to FIG. 1b, in which the stent 10 pursuant the first embodiment is shown in its second shape. It can be particularly recognized from this representation that each positioning arch 15a, 15b, 15c and associated retaining arch 16a, 16b, 16c respectively exhibit an essentially U-shaped or V-shaped structure which is closed towards the lower end 2 of the stent 10. Specifically, each positioning arch 15a, 15b, 15c is cut from a material section of a portion of a tube from which the essentially U-shaped or V-shaped structure of the associated retaining arch 16a, 16b, 16c was taken, as can be seen from the cutting pattern depicted in FIG. 1e.

A comparison of FIG. 1a to FIG. 1b shows that, upon the stent 10 expanding; i.e. when the stent 10 transforms from its first shape into its second shape, the stent 10 shortens in the longitudinal direction L while simultaneously enlarging in cross-section. In the expanded state of stent 10, the respective positioning arches 15a, 15b, 15c are expanded more in the radial direction at the lower end 2 of the stent 10 compared to the upper end 3 of stent 10. Since they protrude more in the radial direction, the positioning arches 15a, 15b, 15c can be deployed into the cardiac valve pockets T of the cardiac valve H to be replaced in particularly easy manner.

Even when a certain anchoring of the stent 10 is achieved at the site of implantation in the heart due to the positioning arches 15a, 15b, 15c already protruding radially from stent 10 in the expanded state of the stent 10, it is noted that the contact force acting on the vascular wall from the positioning arches 15a, 15b, 15c is insufficient to securely anchor the stent 10 at the site of implantation. The previously-mentioned retaining arches 16a, 16b, 16c, which form the lower end 2 of stent 10, are provided for this reason. The retaining arches 16a, 16b, 16c protrude radially from the circumference of the stent 10 in its expanded state such that the retaining arches 16a, 16b, 16c press against the wall of the blood vessel in which the stent is deployed with a radially-acting contact force.

In addition to retaining arches 16a, 16b, 16c, the stent 10 further comprises auxiliary arches 18a, 18b, 18c, which likewise exert a radially-acting contact force against the wall of the blood vessel in the implanted state of stent 10, thereby improving anchoring of stent 10 at the site of implantation.

As can be seen from FIG. 1b, stent 10 pursuant the first embodiment comprises a total of three essentially U-shaped or V-shaped auxiliary arches 18a, 18b, 18c which are closed towards the lower end 2 of said stent 10. Each auxiliary arch 18a, 18b, 18c connects a first retaining arch 16a, 16b, 16c with a second retaining arch neighboring the first retaining arch.

In a top plan view of the lower end region 2 of the expanded stent 10 (cf. FIG. 1c), the lower end region 2 exhibits a dodecagonal polygonal structure formed from the individual arms 16a', 16a", 16b', 16b", 16c', 16c" of retaining arches 16a, 16b, 16c and the individual arms 18a', 18a", 18b', 18b", 18c', 18c" of the auxiliary arches 18a, 18b, 18c. This stent design particularly provides a total of six arches 16a, 16b, 16c, 18a, 18b, 18c uniformly distributed around the lower end region 2 of stent 10, each of which press against the vascular wall and effectively hold the stent 10 in position in the expanded and implanted state of stent 10.

To recapitulate, providing retaining arches 16a, 16b, 16c on the one hand and auxiliary arches 18a, 18b, 18c on the other results in a radial force being exerted on the vascular wall by the respective lower end portions of these arches. This ensures both a secure seal of a valvular prosthesis 100 affixed to stent 10 relative the vascular wall, as well as a secure anchoring of the stent 10, at the site of implantation in the heart.

In addition to the contact force exerted on the vascular wall by way of the retaining arches 16a, 16b, 16c and auxiliary arches 18a, 18b, 18c, it is conceivable for the upper end region 3 of stent 10 to expand radially 10-25% more—in the expanded state of stent 10—compared to the lower end region 2. This gives the stent 10 a slight concave structure which tapers towards the lower end region 2. This ensures secure anchoring of the stent 10 within the vessel by the upper end region 2 of the stent 10 pressing against the vascular wall.

Furthermore, to ensure that minimal longitudinal displacement of a valvular prosthesis affixed to stent 10 can occur relative stent 10, even during the peristaltic movement of the heart and the blood vessel in which stent 10 is deployed, the embodiment of the inventive stent 10 depicted in the drawings provides for the stent 10 to comprise a plurality of fastening portions 11a to 11f extending in the longitudinal direction L of stent 10, by means of which a valvular prosthesis 100 is affixed to the stent 10. Reference is made to FIG. 1d which shows a perspective side view of an endoprosthesis 1 for treating a narrowed cardiac valve or a cardiac valve insufficiency, whereby the endoprosthesis 1 comprises the stent 10 pursuant the first embodiment of the invention for holding a valvular prosthesis 100. The valvular prosthesis 100 comprises at least one valve flap 102 made from a biological or synthetic material.

It will be appreciated that the valvular prosthesis may be made from any suitable material, including biological valves removed from animals such as pigs and horses, man-made biological valves created from connective tissue such as pericardium, tissue grown from cell cultures, and man-made materials and fabrics such as nitinol.

In detail, the first connecting webs 17 of stent 10 connect with connecting portions 22 via their upper ends 17d and with the upper ends 13 of fastening portions 11 via their lower ends 17p. The respective lower ends 14 of the fastening portions which are connected to one and the same connecting web 17 are thereby connected together via an essentially U-shaped or V-shaped auxiliary arch 18a, 18b, 18c which is closed towards the lower end 2 of stent 10.

Specifically, the first embodiment of the inventive stent 10 is shown in FIG. 1d in its expanded state, whereby a valvular prosthesis 100 is fastened to said stent 10 by means of a thread 101 or a thin wire and stretched by the stent 10. It is easily recognized that the widening of the center area and the lower end region 2 of stent 10 at which the valvular prosthesis 100 is disposed achieves spreading of the valvular prosthesis. At the same time, the lower end portions of the retaining arches 16a, 16b, 16c and the auxiliary arches 18a, 18b, 18c exert a radial force on the (not shown in FIG. 1d) vascular wall.

As can be seen from FIG. 1d, a defined plurality of fastening holes 12 are configured in the respective fastening portions 11a to 11f of stent 10, the same being arranged to be distributed at predefined longitudinal positions along the fastening portions 11a to 11f. The thread 101 or thin wire with which the valvular prosthesis 100 is attached to stent 10 is guided through each respective fastening hole 12.

Both components constituting the endoprosthesis 1, namely the stent 10 and the valvular prosthesis 100, are preferably not connected together until directly prior to the surgical procedure. This is of advantage in terms of transport and storage since the stent 10 is a relatively sturdy component mechanically and can be stored for a long period of time without degradation. This is particularly true when the stent 10 is stored in its second shape; i.e. in the expanded state, and not brought it its first (collapsed) shape until directly prior the surgical procedure.

It can be noted from FIGS. 1b and 1d that the respective fastening portions 11a to 11f are configured in the respective arms 16a', 16a", 16b', 16b", 16c', 16c" of retaining arches 16a, 16b, 16c of stoat 10. The size of the fastening holes 12 configured in the fastening portions 11a to 11f should be adapted to the thickness of the thread 101 or wire used to fasten the valvular prosthesis 100 to the stent 10.

The cross-sectional shape to the fastening holes 12 may also be adapted to the cross-sectional shape of the thread 101 or wire used to fasten the valvular prosthesis 100. This allows fixing of the valvular prosthesis 100 to the stent 10 at a precise predefined position relative the stent 10. By providing of a plurality of fastening holes 12 to anchor the valvular prosthesis 100 to the stent 10, precise positioning of the valvular prosthesis on stent 10 is achieved.

Because the fastening holes 12 are adapted to the thickness and/or the cross-sectional shape of the thread 101 or wire used to affix the valvular prosthesis 100 to the stent 10, relative movement between the stent 10 and the valvular prosthesis 100 due to the peristaltic motion of the heart can be effectively prevented when the endoprosthesis 1 is implanted. The valvular prosthesis 100 is thus fastened to the stent 10 with minimal play, based on which friction-induced wear of the thread 101 or wire used to affix the valvular prosthesis is minimized. As shown in the figures the fastening holes 12 have a circular cross-sectional shape.

As already mentioned, the fastening holes 12 configured in the respective fastening portions 11a to 11f may be of different diameters, numbers or cross-sectional shapes (oval, square, etc) according to the diameter of a thread 101 used for affixing the valvular prosthesis 100 to the stent 10, and/or according to the sewing technique utilized for affixing the valvular prosthesis 100 to the stent 10. The diameter, number and/or cross-sectional shape of at least one of the fastening holes 12 may also serve as an indication of the type of the endoprosthesis 1, i.e. the medical device used in the treatment of a narrowing of a cardiac valve and/or a cardiac valve insufficiency. In this respect, the diameter, number and/or cross-sectional shape of the at least one fastening hole 12 may be used for identification to differentiate between different sizes or types of valvular prostheses 100 adapted to be fixed on the stent 10, or may be used for identification to differentiate between different sizes or types of endoprosthesis 1, if a valvular prosthesis 100 is already fixed to the stent 10. For example, a small-sized stent 10 having a small-sized valvular prosthesis 100 fixed thereto or a small-sized stent 10 adapted and configured for carrying a small-sized valvular prosthesis 100 could have circular fastening holes 12 whilst a large-sized stent 10 having a large-sized valvular prosthesis 100 fixed thereto or a large-sized stent 10 adapted and configured for carrying a large-sized valvular prosthesis 100 may have triangular fastening holes 12. This allows the surgeon/cardio staff to easily and visually tell different valve sizes, stent types and/or types of the endoprosthesis apart without the need to measure.

The fastening portions 11a to 11f of the stent 10 (onto which the valvular prosthesis 100 is sewn or sewable) do not change their shape when the stent 10 is compressed, e.g. when the stent 10 is in its first (collapsed) shape shown in FIG. 1a. This phenomenon occurs when standard tube stents are used. Thus the risk of thread wear is minimal.

The stent 10 in accordance with the second embodiment depicted in FIGS. 2a to 2c is fundamentally identical in structural and functional regard to the stent 10 according to the first embodiment depicted in FIGS. 1a to 1c. The same also holds true for the cutting pattern depicted in FIG. 2e which is, in principle, comparable to the cutting pattern according to FIG. 1e. A detailed description of the common features will therefore not be provided.

The only difference to be seen is in the configuration of the catheter retaining means 23 provided at the distal end 3 of stent 10. In contrast to the first embodiment of the inventive stent 10, heads of an essentially round configuration are used as catheter retaining means 23 in the second embodiment, in each case provided with essentially oval eyelets 24.

As already indicated, the stent 1 according to the present invention preferably exhibits a structure integrally cut from a portion of tube, and in particular from a small metal tube, in which a retaining arch 16a, 16b, 16c is allocated to each positioning arch 15a, 15b, 15c, and with which each retaining arch 16a, 16b, 16c is connected by means of an auxiliary arch 18a, 18b, 18c, whereby a fastening portion 11 with a specific number of fastening holes 12 is configured in each arm 16a', 16a", 16b', 16b", 16c', 16c" of retaining arch 16a, 16b, 16c.

FIGS. 1e and 2e each show a two-dimensional projection of a cutting pattern which can be used in the manufacture of the stent 10 pursuant the first or second embodiment of the invention in order to integrally cut a one-piece stent 10 from a portion of tube, in particular a small metal tube. It is evident that, on the one hand, the inventive stent 10 dispenses with fixed-body joints or other similar connective devices between the individual components of stent 10 (positioning arch, retaining arch, auxiliary arch). On the other hand, a stent 10 is provided which exhibits, with minimum longitudinal extension, the functionality of positionability as provided by the positioning arches 15a, 15b, 15c on the one hand and, on the other, the functionality of the defined fastening of a valvular prosthesis 100, as provided by the fastening portions 11 configured in the respective arms 16a', 16a", 16b', 16b", 16c', 16c" of the retaining arch 16a, 16b, 16c.

In addition to its retaining arches 16a, 16b, 16c, the stent 10 further comprises auxiliary arches 18a, 18b, 18c which enable a particularly secure anchoring of stent 10 in the site of implantation in the heart.

The stent 10 is preferably made from a shape memory material. The state of stent 10 shown in FIG. 1a or FIG. 2a, in which the stent 10 is in its first shape and thus in its collapsed state, is the so-called "temporary" shape of the stent structure made from a shape memory material. When an external stimulus acts on the stent structure according to FIG. 1a or FIG. 2a, the shape memory effect is activated and thus the predefined permanent shape saved during the manufacture of the stent 10 as pursuant, for example, FIG. 1b or FIG. 2b, is restored.

Said external stimulus is preferably a specifiable switching temperature whereby, to activate the shape memory effect and thus regenerate the saved permanent shape of the stent 10, the stent material is warmed to a higher temperature than the switching temperature. By selecting a suitable chemical composition of the material used for stent 10, a specific switching temperature can be predefined. In the preferred embodiment of the inventive solution, the switching temperature ranges from between about 20° C. and the body temperature of the patient.

When implanting the stent 10, it is conceivable for the stent 10 to be cooled during the insertion procedure. Once the stent 10 has been guided to its desired site of implantation, i.e. to the native cardiac valve H (cf. FIG. 3a), preferably using a suitable insertion catheter system, the cooling can be stopped. The stent 10 is then allowed to warm up to the patient's body temperature (36° C.) and the shape memory effect of the stent material is thus activated. Due to the self-expanding property of stent 10 having been triggered, radial forces are generated which act on the individual components of the stent, in particular on the positioning arches 15a, 15b, 15c, the retaining arches 16a, 16b, 16c and the auxiliary arches 18a, 18b, 18c of the stent 10.

The inventive stent 10, as well as the insertion catheter system used to implant the stent, are preferably configured so that the stent 10 with the valvular prosthesis 100 affixed thereto can be introduced transarterially into the body of the patient. In one example, the stent 10 is accommodated in the tip of the catheter of the insertion catheter system, the catheter tip being introduced into the body via, for example, puncture of the A. femoris communis (inguinal artery).

Alternatively, the stent 10 according to the invention is also suited for transapical implantation, in which—coming from the apex of the heart—the catheter tip of the insertion catheter system is advanced to the aortic valve through, for example, the left ventricle. With a catheter tip modified accordingly, an analogous implantation of the stent 10 with the valvular prosthesis 100 is thus possible.

Regardless of whether the stent 10 is delivered to the site of implantation via a transarterial or transapical approach, the tip of the catheter of the insertion catheter system is preferably advanced to the implantation site using angiographic (angiography) and echocardiographic (ultrasound) control. The actual implantation of stent 10 with the attached valvular prosthesis 100 then follows.

FIGS. 3a to 3c schematically show the process sequence to illustrate trans-arterial implantation of an endoprosthesis 1 comprising a stent 10 in accordance with the invention. As shown, the implantation of the stent 10 with the valvular prosthesis 100 attached thereto ensues such that the individual components of the stent 10 accommodated in the catheter tip K are successively released by appropriately manipulating the catheter tip K of an insertion catheter system.

The catheter system used to implant the inventive stent 10 is ideally configured such that a liquid cooling agent can be fed through a hollow interior of the catheter system to catheter tip K. The liquid cooling agent, for example in the form of a saline solution, maintains the stent 10 accommodated in the catheter tip K at a temperature below the switching temperature while the catheter tip K is being advanced to the site of implantation. This is of particular advantage when a shape memory material is provided as the material of the stent 10. This is because the stent 10 transforms from a temporary shape into a permanent shape upon the influence of an external stimulus. The temporary shape is the first shape of stent 10 (in collapsed state, when the stent 10 is accommodated in the catheter tip K of the insertion system) and the "permanent shape" is the second shape of stent 10 (the expanded state of the stent 10 after the stent 10 has been released from the catheter tip K).

It is to be noted that the "permanent shape" of the expanded stent 10 conforms to the native shape of its environment. This allows for variations in the shape of the environment at the site of implantation which will vary from patient to patient. This property of stent 10, related to the "permanent shape" of the expanded stent 10 automatically adapting completely to the native shape of its environment, will thus always ensure that the valvular prosthesis 100 is optimally implanted.

Because a shape memory material such as nitinol, i.e. equiatomic alloy of nickel and titanium, can be used for the inventive stent 10, a particularly gentle implantation procedure is achievable when implanting the stent 10 with the valvular prosthesis 100 affixed thereto.

The stent 10 accommodated in the catheter tip K can be cooled by flushing the insertion catheter system with a suitable cooling agent while the catheter tip K is being advanced to keep the temperature of the stent material below the critical transition temperature. Once the catheter tip K with the cooled stent 10 has been advanced to the site of implantation, cooling of the stent 10 should be stopped, as a consequence of which the stent 10 warms up to the body temperature (36° C.) of the patient and the shape memory effect of the stent material is thus activated.

Once the self-expanding property of the individual components of stent 10 have been activated, radial forces are generated which act on the individual components of stent 10, in particular on the positioning arches 15a, 15b, 15c, the retaining arches 16a, 16b, 16c and the auxiliary arches 18a, 18b, 18c of stent 10. Since the respective components of stent 10 are still situated in the catheter tip K, the radial forces developing upon the critical switching temperature being exceeded and acting on the individual components of the stent 10 are still compensated by the wall of the catheter tip K, so that—despite the activation of the shape memory effect—the stent 10 is forcibly kept in its first (collapsed) shape.

Upon the subsequent manipulation of catheter tip K—by the appropriate incremental release of the stent 10—the individual components of stent 10, are then discharged from the catheter tip K. As FIG. 3a shows, the positioning arches 15a, 15b, 15c of stent 10 spread out radially due to the acting radial forces. The expanded positioning arches 15a, 15b, 15c can then be positioned into the pockets T of the native cardiac valve H.

Thereafter—as depicted in FIG. 3b—the remaining components of stent 10 are sequentially released from the catheter tip K. The released remaining components of stent 10, in particular the auxiliary arches 18a, 18b, 18c and the retaining arches 16a, 16b, 16c with the valvular prosthesis 100, then spread out radially and the valvular prosthesis 100 attached to the fastening portions 11 unfolds like an umbrella.

The radial forces acting on both the retaining arches 16a, 16b, 16c and the auxiliary arches 18a, 18b, 18c of the stent 10 as well as the radial forces acting on the upper end region 3 of stent 10, result in the stent 10 being pressed radially against the vascular wall (cf. FIG. 3c). This effects a secure anchoring of stent 10 with the expanded valvular prosthesis 100 at the site of implantation on the one hand and, on the other, a reliable seal of the valvular prosthesis 100 at the lower end 2 of stent 10.

The catheter tip K of the insertion catheter system is then manipulated further to release the eyelets 24 of the stent 10, thereby allowing the upper end region 3 of the stent 10 to expand. In so doing, the valve leaflets of the native cardiac valve H are clamped between respective positioning and retaining arches and the valvular prosthesis 100 disposed on the lower end 2 of stent 10 can spread open.

After the successful implantation of the stent 10 and valvular prosthesis 100, the catheter is then removed from the body of the patient.

The invention is not limited to a stent 10 made from shape memory material which self-expands from its first (collapsed) shape into its second (expanded) shape in response to an external stimulus. Rather, it is also categorically conceivable for the stent 10 to be expanded using a conventional balloon system.

The inventive solution is also not limited to the embodiments as described with reference to the attached drawings. Rather, combinations of the specified individual features are also conceivable.

With respect to fixing the upper area 3 of stent 10 to the wall of the blood vessel into which the stent 10 is deployed, it would be conceivable for the stent 10 to comprise barb members arranged, for example, on the eyelets 24, the tips of the barbs pointing toward the lower end 2 of stent 10.

LIST OF REFERENCE NERALS 1 endoprosthesis
2 lower end of the stent/endoprosthesis 3 upper end of the stent/endoprosthesis
10 cardiac valve stent/stent
11 fastening portion of the stent
12 fastening holes
13 upper end of the fastening portion
14 lower end of the fastening portion
15a-15c positioning arches
15a', 15a" arms of the first positioning arch
15b', 15b" arms of the second positioning arch
15c', 15c" arms of the third positioning arch
16a-16c retaining arches
16a', 16a" arms of the first retaining arch
16b', 16b" arms of the second retaining arch
16c', 16c" arms of the third retaining arch
17 first connecting web
17d upper end of the first connecting web
17p lower end of the first connecting web
18a-18c auxiliary arches
18a', 18a" arms of the first auxiliary arch
18b', 18b" arms of the second auxiliary arch
18c', 18c" arms of the third auxiliary arch
20 head portion of the positioning arch
21 reference marker
22 connecting portion between the arms of neighboring positioning arches
23 catheter retaining means/catheter retaining head
24 eyelet
25 second connecting web
100 valvular prosthesis
101 thread
102 flap segment of the valvular prosthesis
H native cardiac valve
K catheter tip of an insertion catheter system
L longitudinal direction of the stent
T pocket of the native cardiac valve

What is claimed is:

1. An endoprosthesis for implantation at a native heart valve, the endoprosthesis comprising:
an expandable stent comprising:
a plurality of retaining arches, each retaining arch comprising a retaining apex and coupled to another retaining arch of the plurality of retaining arches;
a plurality of positioning arches, each positioning arch comprising a positioning apex aligned with a respective retaining apex of a retaining arch of the plurality of retaining arches, and each positioning arch coupled to another positioning arch of the plurality of positioning arches; and
a plurality of connecting struts, each connecting strut coupled at a first end of each connecting strut to at least one positioning arch of the plurality of positioning arches and coupled at a second end of each connecting strut to at least one retaining arch of the plurality of retaining arches, the plurality of connecting struts configured to offset the plurality of retaining arches from the plurality of positioning arches,
a plurality of auxiliary arches, each auxiliary arch coupled at a primary end of each auxiliary strut to a first retaining arch of the plurality of retaining arches and coupled at a secondary end of each auxiliary strut to a second retaining arch of the plurality of retaining arches, the plurality of auxiliary arches uniformly distributed around a lower end of the expandable stent and configured to press against a vascular wall, and the plurality of auxiliary arches and the plurality of retaining arches configured to form a seal with the vascular wall,
wherein the plurality of retaining arches and the plurality of positioning arches are configured to be sequentially expanded to cause the plurality of retaining arches and the plurality of positioning arches to clip at least one native leaflet of the native heart valve.

2. The endoprosthesis of claim 1, further comprising a valve prosthesis coupled to at least a portion of the plurality of retaining arches, the valve prosthesis comprising a plurality of prosthetic leaflets.

3. The endoprosthesis of claim 2, wherein each retaining arch of the plurality of retaining arches comprises a plurality of fastening holes and wherein the valve prosthesis is coupled to the at least a portion of the plurality of retaining arches via one or more sutures extending through the fastening holes.

4. The endoprosthesis of claim 1, wherein the plurality of the positioning arches are configured to at least partially expand while the plurality of retaining arches remain in the collapsed state.

5. The endoprosthesis of claim 4, wherein the plurality of the positioning arches are configured to be positioned into pockets of the native heart valve.

6. The endoprosthesis of claim 4, wherein the plurality of retaining arches are configured to expand after the plurality of positioning arches are at least partially expanded.

7. The endoprosthesis of claim 1, wherein the plurality of retaining arches includes exactly three retaining arches and the plurality of positioning arches includes exactly three positioning arches.

8. The endoprosthesis of claim 1, wherein each positioning arch of the plurality of positioning arches is coupled to another positioning arch at a junction and each connecting strut of the plurality of connecting struts is coupled to a respective junction.

9. The endoprosthesis of claim 1, wherein each retaining arch of the plurality of retaining arches is coupled to another retaining arch at a junction and each connecting strut of the plurality of connecting struts is coupled to a respective junction.

10. The endoprosthesis of claim 1, wherein the each auxiliary arch of the plurality of auxiliary arches is configured to anchor the expandable stent.

11. A method for implanting an endoprosthesis at a native heart valve, the method comprising:
delivering the endoprosthesis to the native heart valve in a compressed state, the endoprosthesis comprising an expandable stent comprising a plurality of retaining arches, a plurality of positioning arches, a plurality of connecting struts coupling the plurality of retaining arches to the plurality of positioning arches, and a plurality of auxiliary arches uniformly distributed around a lower end of the expandable stent and configured to press against a vascular wall, each auxiliary arch coupled at a primary end of each auxiliary arch to a first retaining arch of the plurality of retaining arches and coupled at a secondary end of each auxiliary arch to a second retaining arch of the plurality of retaining arches, the plurality of auxiliary arches and the plurality of retaining arches configured to form a seal with a vascular wall;
causing the plurality of positioning arches to at least partially expand;
positioning, after causing the plurality of positioning arches to at least partially expand, the plurality of positioning arches into pockets of the native heart valve; and causing, after positioning the positioning arches into pockets of the native heart valve, the plurality of retaining arches to at least partially expand, thereby clipping at least one native leaflet of the native heart valve between at least one of the plurality of retaining arches and at least one of the plurality of positioning arches, wherein the plurality of connecting struts offset the plurality of positioning arches form the plurality of the retaining arches.

12. The method of claim 11, wherein the endoprosthesis further comprises a valve prosthesis coupled to at least a portion of the plurality of retaining arches, the valve prosthesis comprising a plurality of prosthetic leaflets.

13. The method of claim 12, wherein each retaining arch of the plurality of retaining arches comprises a plurality of fastening holes, the method further comprising securing the valve prosthesis to plurality of fastening holes using a suture.

14. The method of claim 11, wherein the plurality of retaining arches includes exactly three retaining arches and the plurality of positioning arches includes exactly three positioning arches.

15. The method of claim 11, wherein each positioning arch of the plurality of positioning arches is coupled to another positioning arch at a junction and each connecting strut of the plurality of connecting struts is coupled to a respective junction.

16. The method of claim 11, wherein each retaining arch of the plurality of retaining arches is coupled to another retaining arch at a junction and each connecting strut of the plurality of connecting struts is coupled to a respective junction.

17. The method of claim 11, further comprising extracting the expandable stent from a metal tube via laser cutting.

18. The method of claim 11, wherein each retaining arch of the plurality of retaining arches is U-shaped or V-shaped.

19. The method of claim 11, wherein each positioning arch of the plurality of positioning arches is U-shaped or V-shaped.

20. The method of claim 11, wherein the each auxiliary arch of the plurality of auxiliary arches is configured to anchor the expandable stent.

* * * * *